United States Patent [19]

Kiyokawa et al.

[11] Patent Number: 5,409,928
[45] Date of Patent: Apr. 25, 1995

[54] CONDENSED PYRAZOLE DERIVATIVES, METHOD OF MANUFACTURING THE SAME, AND ANDROGEN INHIBITOR

[75] Inventors: Hiroshi Kiyokawa, Nara; Satoshi Yamada, Otsu; Keisuke Miyajima, Otsu; Koji Edamatsu, Otsu; Kunihiko Tatsumi, Otsu; Takeshi Yamauchi, Kyoto; Kazumasa Kishi, Shiga; Kunihiko Kiyono, Otsu, all of Japan

[73] Assignee: Otsuka Pharmaceutical Co., Ltd., Tokyo, Japan

[21] Appl. No.: 138,113

[22] Filed: Oct. 20, 1993

[30] Foreign Application Priority Data

Oct. 20, 1992 [JP] Japan .................................. 4-281446
Mar. 5, 1993 [JP] Japan .................................. 5-45424

[51] Int. Cl.$^6$ .................... C07D 487/04; A61K 31/53
[52] U.S. Cl. ........................................ 514/246; 544/219
[58] Field of Search ........................ 544/219; 514/246

[56] References Cited

FOREIGN PATENT DOCUMENTS 0503099 9/1992 European Pat. Off. .
1359563 7/1974 United Kingdom .

OTHER PUBLICATIONS

Fujii et al, Chemical Abstracts, vol. 109, entry 211092p (1988).

*Primary Examiner*—John M. Ford
*Attorney, Agent, or Firm*—Sughrue, Mion, Zinn, Macpeak & Seas

[57] ABSTRACT

This invention provides a condensed pyrazole derivative of the Formula (1):

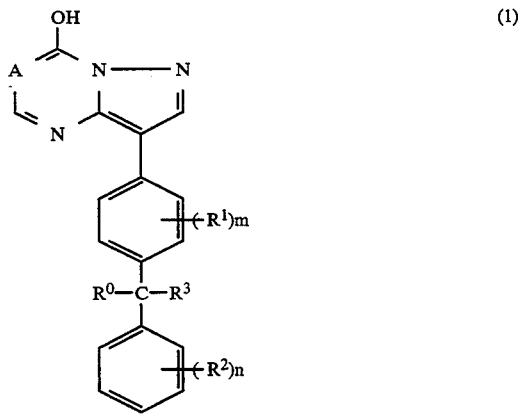

(where A denotes CH or N, $R^0$ and $R^3$ denote same or different, a hydrogen atom or a lower alkyl group, $R^1$ and $R^2$ denote same or different, a hydrogen atom, a lower alkyl group, a lower alkoxy group, a lower alkylthio group, a nitro group or a halogen atom, m denotes 1 or 2, and n denotes 1, 2 or 3, provided that, when n is 2, two $R^2$ may be connected to each other to form a lower alkylenedioxy group), or its pharmaceutically acceptable salt. This derivative or its salt is excellent in the effect of inhibiting the expression of action of androgen, thereby being excellent in therapeutical effect of benign prostatic hypertrophy, prostatic carcinoma, etc., and has a long lasting of efficacy and high oral absorption.

10 Claims, No Drawings

CONDENSED PYRAZOLE DERIVATIVES, METHOD OF MANUFACTURING THE SAME, AND ANDROGEN INHIBITOR

FIELD OF THE INVENTION

The present invention relates to novel condensed pyrazole derivatives which inhibit expression of action of androgen, method of manufacturing the same, and androgen inhibitor.

BACKGROUND OF THE INVENTION

Androgen (male hormone) is mainly synthesized in the testes of adult males, and possesses the actions for maintaining the functions of the reproductive organ and accessory reproductive organs (prostate, seminal gland), spermatogenesis and the like. If the balance of androgen and estrogen (female hormone) is broken and the action of androgen is encouraged, it is known to induce benign prostatic hypertrophy, prostatic carcinoma, female hairiness, male baldness or pimple. Hypertrophy of the prostate is observed in about 30% of male of 60 years or elder, and symptoms of benign prostatic hypertrophy (BPH) such as dysuria are noted in half of them.

As androgen, testosterone, androstenedione, dehydroepiandrosterone, and others are known. It is also known that 85% of androgens synthesized in the tests of the adult men is testosterone.

The testosterone is transformed, in the cells of the prostate, into 5 α-dihydrotestosterone (5 α-DHT) by 5α-reductase, and is bound with a receptor to get into the nucleus, and activates the genes, thereby expressing the actions as mentioned above.

As substances inhibiting expression of such actions of androgens, for example, chlormadinone acetate, flutamide, and hydroxyflutamide are known. However, the androgen activity inhibiting actions by these compounds were not sufficiently satisfactory, the therapeutic effects on benign prostatic hypertrophy, prostatic carcinoma, female hairiness, male baldness or pimple were not sufficient.

SUMMARY OF THE INVENTION

It is hence a primary object of the invention to provide novel compounds excellent in inhibitory action of expression of actions of androgens, and excellent in therapeutic effects of benign prostatic hypertrophy, prostatic carcinoma, female hairiness, male baldness or pimple.

It is the other object of the invention to provide novel compounds having long lasting of efficacy and excellent in oral-absorption property.

The present inventors, as a result of intensive research in order to achieve the above objects, obtained a new finding that the condensed pyrazole derivatives expressed in Formula (1) and their pharmaceutically available salts are excellent in the effect of inhibiting the expression of action of androgens, and completed the invention.

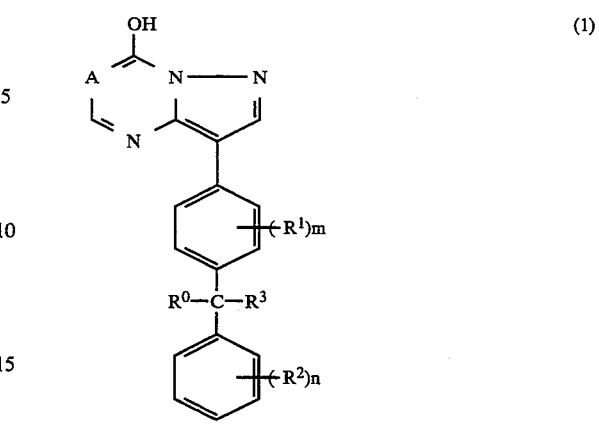

[where A denotes CH or N, $R^0$ and $R^3$ denote same and different, a hydrogen atom or a lower alkyl group, $R^1$ and $R^2$ denote same and different, a hydrogen atom, a lower alkyl group, a lower alkoxy group, a lower alkylthio group, a nitro group or a halogen atom, m denotes 1 or 2, n denotes 1, 2 or 3, provided that, when n is 2, two $R^2$ may be connected to each other to form a lower alkylenedioxy group.]

The condensed pyrazole derivatives (1) and the pharmaceutically available salts of the invention are novel compounds not found in literature, and possess a strong inhibitory action on binding of between receptor in cell and 5 α-DHT, binding of between receptor in cell and mibolerone, etc.

Therefore, the condensed pyrazole derivatives (1) and their pharmaceutically available salts of the invention are capable of inhibiting the expression of actions of androgen, and present excellent pharmaceutical effects in benign prostatic hypertrophy, prostatic carcinoma, female hairiness, male baldness, pimple or others induced by promotion of actions of androgens. Especially, the derivatives (1) of the invention and their pharmaceutically available salts possess advantages of a long lasting of efficacy and being excellent in oral absorption.

DETAILED DESCRIPTION OF THE INVENTION

Examples of the lower alkyl group include alkyl groups having 1 to 6 carbon atoms such as methyl, ethyl, butyl, propyl, isopropyl, t-butyl, pentyl, hexyl and the like.

Examples of the lower alkoxy group include alkoxy groups having 1 to 6 carbon atoms, such as methoxy, ethoxy, propoxy, isopropoxy, butoxy, t-butoxy, pentyloxy, hexyloxy and the like.

Examples of lower alkylthio group include alkylthio groups having 1 to 6 carbon atoms, such as methylthio, ethylthio, butylthio, propylthio, isopropylthio, t-butylthio, pentylthio, hexylthio and the like.

Halogen atoms include chlorine, bromine, iodine, and fluorine.

Examples of the lower alkylenedioxy group which may be formed by connecting two $R^2$, include alkylenedioxy groups having 1 to 4 carbon atoms, such as methylenedioxy, methylmethylenedioxy, ethylenedioxy, dimethylmethylenedioxy, trimethylenedioxy, 1,1-dimethylethylenedioxy, 1-methyltrimethylenedioxy, tetramethylenedioxy.

The compounds of the invention expressed in Formula (1) may be manufactured in various methods, for example, in the method illustrated in the following reaction schemes.

Reaction scheme-1

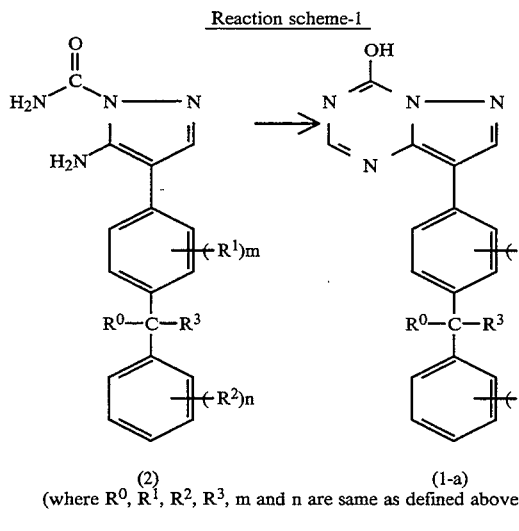

(where $R^0$, $R^1$, $R^2$, $R^3$, m and n are same as defined above.)

The compound of the invention expressed in Formula (1-a) can be obtained by reacting the compound expressed in Formula (2) with an alkyl orthoformate such as methyl orthoformate, ethyl orthoformate and the like. The reaction may be accomplished in a suitable solvent which does not adversely affect on the reaction, but does not always need solvent, since the alkyl orthoformate also functions as a solvent.

The molar ratio of the alkyl orthoformate to the compound of Formula (2) may be 1:1 to 15:1. The reaction is usually performed at 80° C. to 120° C., and is terminated in about 1 to 15 hours.

Reaction scheme-2

(1) First step

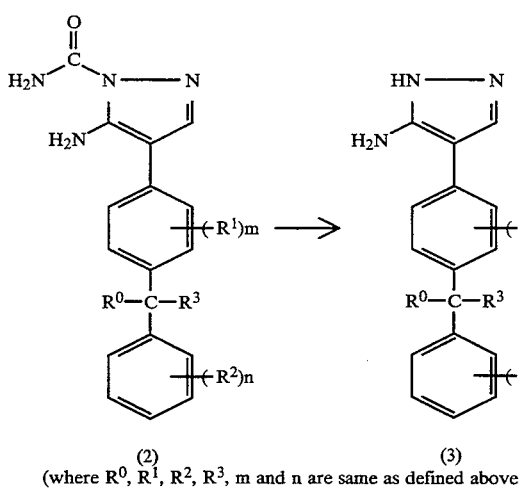

(where $R^0$, $R^1$, $R^2$, $R^3$, m and n are same as defined above.)

This reaction is to obtain the compound expressed in Formula (3) by reaction of the compound expressed in Formula (2) in the presence of a base without solvent or in a proper solvent.

Examples of the base may include alkali metal hydroxides such as sodium hydroxide and potassium hydroxide, alkali metal carbonates such as sodium carbonate and potassium carbonate, alkali metal hydrogencarbonates such as sodium hydrogencarbonate and potassium hydrogencarbonate, and other inorganic bases.

As the solvent, any solvents may be used so far as not to affect the reaction, including, for example, lower alcohols such as methanol and ethanol, and mixed solvent of lower alcohol and water. When such mixed solvent is used, the mixing ratio of the lower alcohol to water may be in a range of about 1:1 to 10:1.

The molar ratio of the basic compound to the compound (2) is 1:1 to 50:1, preferably 1:1 to 20:1. The reaction temperature is room temperature to 100° C., preferably 30° C. to 100° C. The reaction time is about 10 minutes to 4 hours.

(2) Second step

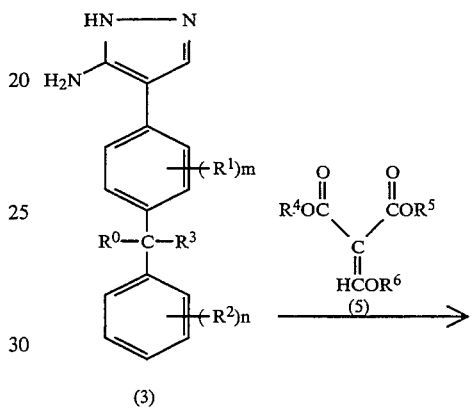

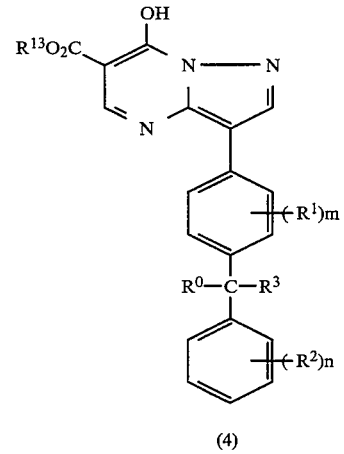

(where $R^0$, $R^1$, $R^2$, $R^3$, m and n are same as defined above, and $R^4$, $R^5$ $R^6$ and $R^{13}$ are same or different, a lower alkyl group.)

This reaction is to obtain the compound expressed in Formula (4) by reaction of the compound expressed in Formula (3) with the compound expressed in Formula (5) in the presence or absence of an acid without solvent or in a suitable solvent.

Examples of the solvent may include ethanol, methanol or other alcohols; pyridine, chloroform, dichloromethane or other halogenated hydrocarbons; dioxane, tetrahydrofuran (THF) or other ethers; benzene, toluene or other aromatic hydrocarbons; N,N-dimethylformamide (DMF), dimethylsulfoxide (DMSO), acetonitrile or other non-protic polar solvents. Examples of acids may include Lewis acids such as anhydrous aluminium chloride, stannic chloride, titanium tetrachloride, boron trichloride, boron trifluoride-ethylether complex and zinc chloride; inorganic acids such as phosphoric acid, hydrochloric acid, nitric acid and sulfuric acid; and organic acids such as trichloroacetic acid, trifluoroacetic acid, methansulfonic acid and acetic acid.

The molar ratio of the compound (5) to the compound (3) is at least 1:1, preferably 1:1 to 2:1. The molar ratio of the acid to the compound (3) is 1:1 to 50:1, preferably 1:1 to 20:1. The reaction temperature is usually 50° C. to 150° C., preferably 80° C. to 120° C. The reaction time is terminated in about 1 hour to 60 hours.

(3) Third step

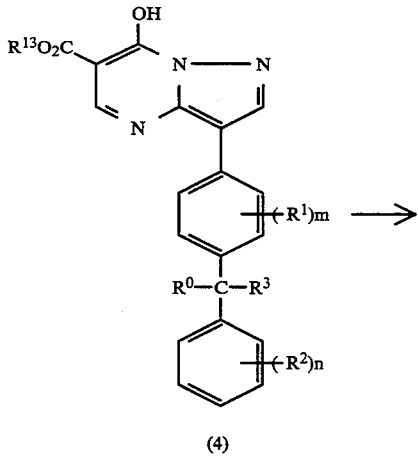

(4)

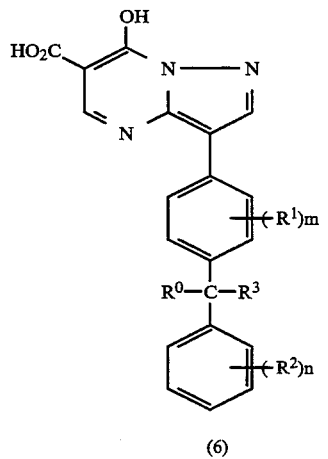

(6)

(where $R^0$, $R^1$, $R^2$, $R^3$, m, n and $R^{13}$ are same as defined above.)

This reaction is to obtain the compound expressed in Formula (6) by hydrolyzing the compound expressed in Formula (4). The reaction is carried out in an inert solvent in the presence of a basic compound or an acidic compound. Examples of inert solvent include alcohols such as methanol and ethanol, and ethers such as dimethylether, diethylether, tetrahydrofurane, dioxane and anisol. Examples of basic compound include trialkylamines such as triethylamine and tributylamine, organic bases such as pyridine, picoline, 1,5-diazabicyclo[4,3,0]-non-5-ene, 1,4-diazabicyclo[2,2,2]octane and 1,8-diazabicyclo[5,4,0]undec-7-ene, alkali metal hydroxides such as sodium hydroxide and potassium hydroxide, alkali metal carbonates such as sodium carbonate and potassium carbonate, alkali metal hydrogencarbonates such as sodium hydrogencarbonate and potassium hydrogencarbonate. Examples of acidic compound include Lewis acids such as anhydrous aluminium chloride, stannic chloride, titanium tetrachloride and boron trichloride, inorganic acids such as hydrochloric acid, hydrobromic acid, nitric acid and sulfuric acid, and organic acids such as trichloroacetic acid, trifluoroacetic acid, methansulfonic acid, acetic acid, and formic acid, acid-type ion-exchange resin, and the like.

The molar ratio of these basic or acidic compound to the compound (4) is 1:1 to 100:1, preferably 1:1 to 20:1. The reaction is carried out at a temperature from −20° C. to 100° C., preferably −10° C. to 80° C., for about 30 minutes to 48 hours, preferably 1 hour to 24 hours.

Besides, deesterification reaction using a catalytic reduction method may be employed.

(4) Fourth step

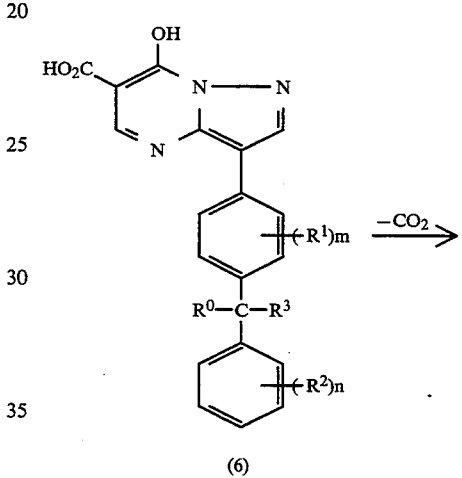

(6)

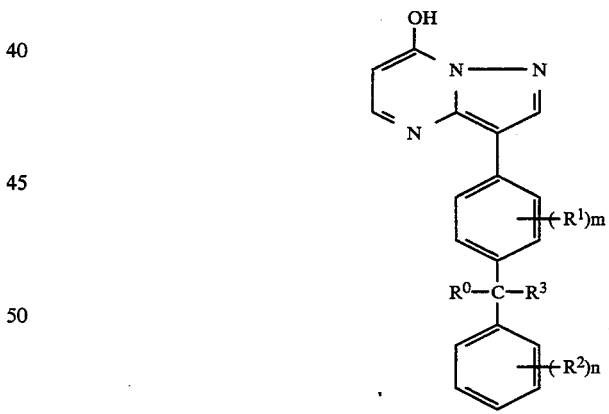

(1-b)

(where $R^0$, $R^1$, $R^2$, $R^3$, m and n are same as defined above.)

This reaction is to obtain the compound of this invention expressed in Formula (1-b) by decarboxylation from the compound of Formula (6). The reaction is performed in the presence of a basic compound without solvent or in a proper solvent. As occasion demands, the reaction may be performed in a sealed tube if necessary. Examples of basic compound may include aniline, N,N-dimethylaniline, N,N-diethylaniline, N-methylaniline, N-ethylaniline, pyridine,α-picoline,β-picoline,γ-picoline, 2,3-lutidine, 2,4-lutidine, 2,5-lutidine, 2,6-lutidine, 3,4-lutidine, 3,5-lutidine, triethylamine, diethylamine, ethylamine, methylamine, ammonia, and the like.

The reaction is carried out at 0° C. to 150° C., preferably 30° C. to 100° C., for about 10 minutes to 12 hours, or preferably about 30 minutes to 6 hours.

Reaction sceme-3

This reaction scheme is to obtain the compound of Formula (2) which is the starting material of the reaction schemes-1 and 2.

(1) First step $$\underset{(12)}{\text{COOH}\text{-Ar}(R^1)_m\text{-C}R^0R^3\text{-Ar}(R^2)_n} \longrightarrow \underset{(11)}{\text{COOR}^9\text{-Ar}(R^1)_m\text{-C}R^0R^3\text{-Ar}(R^2)_n}$$

(where $R^0$, $R^1$, $R^2$, $R^3$, m and n are same as defined above, and $R^9$ denotes a lower alkyl group.)

This reaction is to obtain the compound expressed in Formula (11) by ordinary esterification of the compound expressed in Formula (12).

The esterification is carried out, for example, by reacting the compound (12) with an alcohol expressed in a formula:

$$R^9\text{—OH}$$

(where $R^9$ is same as defined above) in the presence of a catalyst. As the catalyst, a general catalyst for esterification is used, for example, inorganic acids such as hydrogen chloride, concentrated sulfuric acid, phosphoric acid, polyphosphoric acid, boron trifluoride and perchloric acid; organic acids such as trifluoroacetic acid, trichloromethanesulfonic acid, naphthalenesulfonic acid, p-toluenesulfonic acid, benzenesulfonic acid and ethanesulfonic acid; acid anhydrides such as trichloromethanesulfonic acid anhydride and trifluoromethanesulfonic acid anhydride, thionyl chloride, and the like.

Besides, a cationic exchange resin (acid type) may be also used. The esterification is performed without solvent or in the presence of a suitable solvent. The available solvents are any of ordinary solvent generally used in esterification, aromatic hydrocarbons such as benzene, toluene and xylene, halogenated hydrocarbons such as dichloromethane, dichloroethane and chloroform, and ethers such as diethylether, tetrahydrofuran and dioxane. The molar ratio of the acid to the compound (12) is from equimolar amounts to 100:1, preferably 10:1 to 30:1. The reaction temperature is —20° C. to 200° C., preferably 0° C. to 150° C.

Incidentally, the compound (11) may be also obtained by reacting the alkali metal salt of compound (12) (for example, sodium salt, potassium salt) with a halide compound expressed in a formula:

$$R^9\text{—X}$$

(where $R^9$ is same as defined above), reacting the compound (12) with a diazoalkane, e.g. diazomethane, diazoethane or diazopropane, or reacting an alcohol expressed in a formula:

$$R^9\text{—OH}$$

(where $R^9$ is same as defined above) with the compound obtained by converting the carboxyl group of compound (12) into a reactive group (acid chloride, amide or acid anhydride). These esterifications may be performed according to the conventional method.

(2) Second step $$\underset{(11)}{\text{CO}_2R^9\cdots} \longrightarrow \underset{(10)}{\text{CH}_2\text{OH}\cdots} \longrightarrow$$

$$\underset{(9)}{\text{CH}_2X\cdots} \longrightarrow \underset{(8)}{\text{NC-CH}_2\cdots}$$

(where $R^0$, $R^1$, $R^2$, $R^3$, m, and $R^9$ are same as defined above, and X denotes a halogen atom.)

This reaction is composed of steps of obtaining the compound expressed in Formula (10) by reducing the compound expressed in Formula (11) with a hydride-reducing agent, obtaining the compound expressed in Formula (9) by reacting the compound (10) thus obtained with a halogenating agent, and obtaining the compound expressed in Formula (8) by reacting the compound (9) with a cyanide compound.

The reaction for obtaining the compound (10) from the compound (11) is performed in a suitable solvent. Examples of available solvent include ethers such as diethylether, tetrahydrofuran, dioxane and diglyme, aliphatic hydrocarbons such as hexane and heptane, aromatic hydrocarbons such as benzene and toluene. Examples of the hydride-reducing agent include lithium aluminium hydride, aluminium hydride, aluminium isobutylhydride, lithium borohydride, sodium borohydride-aluminium chloride, diborane and the like. The molar ratio of the hydride-reducing agent to the compound (11) is at least 0.5:1, preferably 0.6:1 to 1.2:1. The reaction is usually carried out at a temperature from ice-cooling to 100° C., preferably 0° C. to 50° C., for about 30 minutes to 10 hours.

The reaction for obtaining the compound (9) from the compound (10) is performed without solvent or in a suitable solvent. Examples of the solvent using in this reaction include ethers such as diethylether, tetrahydrofuran and dioxane, halogenated hydrocarbons such as methylene chloride and dichloroethane, aromatic hydrocarbons such as benzene and toluene. Examples of the halogenating agent include thionyl halides such as thionyl chloride and thionyl bromide, hydrogen halides such as hydrogen chloride, hydrogen bromide and hydrogen iodide, and phosphorus halide such as phosphorus trichloride and phosphorus tribromide. The molar ratio of halogenating agent to the compound (10) is at least equimolar amounts, preferably 1:1 to 1.3:1. The reaction is carried out at a temperature from ice-cooling to 100° C., preferably 0° C. to 50° C., and is terminated in about 30 minutes to 5 hours.

The reaction for obtaining the compound (8) from the compound (9) is performed in a suitable solvent. Examples of the solvent used in this reaction include lower alcohols such as methanol, ethanol and propanol, nonprotic polar solvents such as acetone, N,N-dimethylformamide (DMF), dimethylsulfoxide (DMSO) and triamide hexamethylphosphate (HMPA), and the mixing solvent of water and any of these solvents. Examples of cyanide compound include potassium cyanide, sodium cyanide, silver cyanide, copper cyanide and calcium cyanide. The molar ratio of cyanide compound to the compound (9) is at least equimolar amounts, preferably 1:1 to 1.3:1. The reaction is carried out at a temperature from room temperature to 150° C., preferably room temperature to 100° C., and is terminated in about 1 hour to 24 hours.

(3) Third step

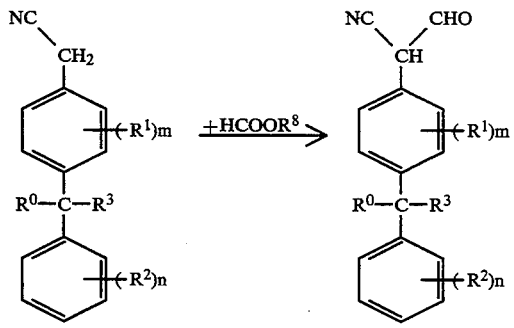

(where $R^0$, $R^1$, $R^2$, $R^3$, m and n are same as defined above, and $R^9$ denotes a lower alkyl group.)

This reaction is to obtain the compound of Formula (7) by reaction of the acetonitrile derivative expressed in Formula (8) and a formate.

The reaction is performed in an inert solvent. Examples usable as inert solvent may include aromatic hydrocarbons such as benzene, toluene and xylene, ethers such as diethylether, tetrahydrofuran and dioxane, N,N-dimethylformamide, dimethylsulfoxide and the like. The molar ratio of the ester to the compound (8) may be at least an equimolar amount, preferably 1.05:1 to 1.25:1. The reaction is preferably performed in ice-cooled state for about 5 to 20 minutes, and then at room temperature for about 4 to 15 hours. In order to progress the reaction sufficiently, sodium alkoxide such as sodium methoxide, or metal hydride such as sodium hydride should be preferably added at least an equimolar amount to the ester.

The reaction product (7) is deposited or separated by steps of adding water to reaction liquid, recovering the water layer, and then adjusting pH to 3 to 4 with mineral acid such as hydrochloric acid.

(4) Fourth step

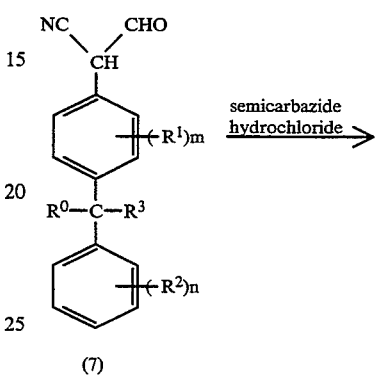

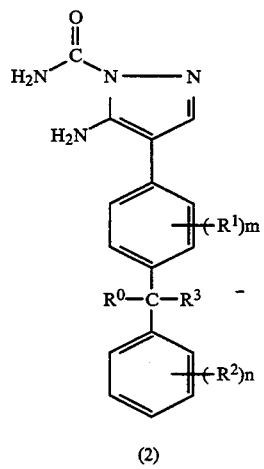

(where $R^0$, $R^1$, $R^2$, $R^3$, m and n are same as defined above.)

This reaction is to obtain the compound expressed in Formula (2) mentioned above by adding semicarbazide mineral acid salt (e.g. semicarbazide hydrochloride) to the compound expressed by Formula (7) under ice-cooling in at least equimolar amounts, preferably about 1 to 1.2 mole per 1 mole of the compound (7), and the mixture is reacted at room temperature for about 4 to 15 hours.

In this reaction, a solvent which does not affect on the reaction, for example, a lower alcohols such as methanol and ethanol, or a mixed solvent of the lower alcohol with water. When using the mixed solvent, a mixing ratio of the lower alcohol to water may be about 1:1 to 10:1.

Reaction scheme-4

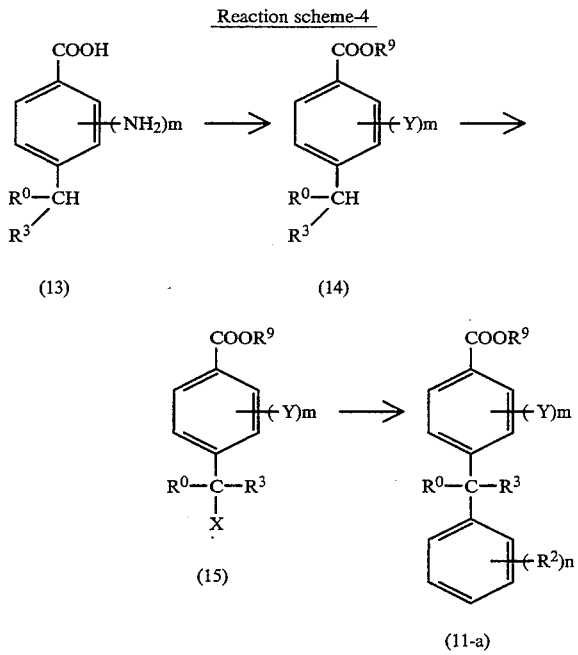

(where $R^0$, $R^2$, $R^3$, m, n, $R^9$ and X are same as defined above, and Y denotes a halogen atom which is identical with or different from X.)

This reaction scheme is suitably adapted to preparation of an intermediate for obtaining the compound of the invention in which $R^1$ in the general Formula (1) is halogen atom.

The reaction of the first step is composed of reacting an amino group-substituted benzoic acid derivative (13) with nitrous acid or its salt (e.g. sodium salt) to obtain a diazonium salt, substituting a diazo group into a halogen atom with copper(I) halide, and esterifying the carboxy group in the same manner as mentioned above to obtain the compound expressed in Formula (14). The preparation of the diazonium salt is performed at a low temperature (usually, from 0° C. to 5° C.) in the presence of excess amount of an acid such as hydrochloric acid, hydrobromic acid, sulfuric acid. The reaction is terminated in about 5 to 30 minutes. The molar ratio of the nitrous acid or its salt to the compound (13) may be 1:1 to 1.05:1.

The substitution of the diazonium group may be carried out at a temperature from 0° C. to 5° C. for 30 minutes to 2 hours by adding copper (I) halide to the reaction liquid without isolating the resulting diazonium salt. The molar ratio of copper(I) halide to the compound (13) may be used 1:1 to 1.05:1. Instead of the copper (I) halide, copper powder and hydrohalogenic acid may be employed.

The compound of Formula (15) is obtained by reacting the compound of Formula (14) with a halogenating agent such as N-bromosuccinimide. The reaction is carried out by heating the mixture in the presence of a catalyst in a solvent at a temperature from 60° C. to 100° C. for 10 minutes to 1 hour. Examples of the catalyst include perbenzoic anhydride, percuminic anhydride, azobisisobutyronitrile and the like.

The compound of Formula (11-a) is obtained by reacting the compound of Formula (15), in the presence of a catalyst, with a benzene derivative expressed by the following Formula.

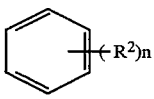

(where $R^2$ and n are same as defined above.)

Examples of the catalyst include anhydrous aluminium chloride, sulfuric acid, phosphoric acid, boron trifluoride and the like. The molar ratio of the catalyst to the compound (13) may be 1:1 to 3:1. In this reaction, the benzene derivatives acts as a solvent, and therefore solvent is not required. The reaction is carried out at a temperature from 0° C. to 100° C., for about 30 minutes to 4 hours.

Reaction scheme-5

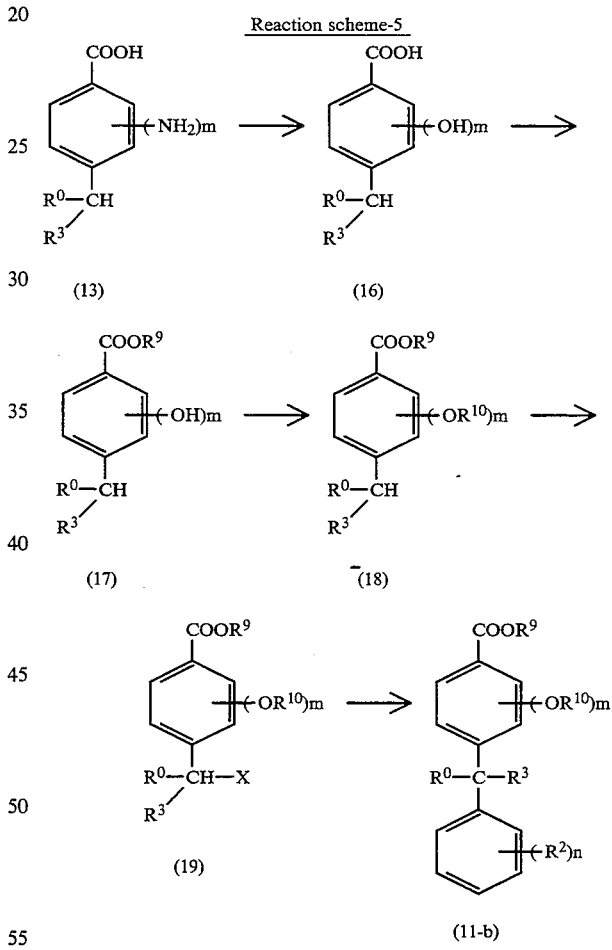

(where $R^0$, $R^2$, $R^3$, m, n, $R^9$ and X are same as defined above, and $R^{10}$ denotes a lower alkyl group.)

This reaction scheme is suitably adapted to preparation of an intermediate for obtaining the compound of the invention in which $R^1$ in the general Formula (1) is alkoxy group.

The reaction of the first step is composed of reacting an amino group-substituted benzoic acid derivative with nitrous acid or its salt (e.g. sodium salt) at a low temperature to obtain a diazonium salt, and heating the diazonium salt to obtain the compound of Formula (16)

in which the amino group of Formula (13) is substituted to a hydroxy group.

The diazonium salt is prepared in the same manner as in the above reaction scheme-4. The heating temperature of the diazonium salt is usually in the range from 5° C. to 100° C., and the reaction is terminated in about 30 minutes to 2 hours.

Next, the carboxy group of the compound of Formula (16) is esterified to obtain the compound of Formula (17). The esterification is carried out in the same manner as in the first step of the reaction scheme-3.

After esterification, the etherification of the compound (17) is carried out. The etherification is performed, for example, by reacting the compound (17) with a dimethyl sulfate in the presence of a base. Examples of the base include sodium hydroxide, potassium hydroxide, potassium carbonate, sodium carbonate and the like. The molar ration of dimethyl sulfate to the compound (17) may be 1:1 to 1.5:1. As other etherification, the reaction of the compound (17) with alcohol $R^{10}OH$ (where $R^{10}$ is same as defined above.), or the reaction of sodium salt of the compound (17), of which the hydroxy group is converted into the sodium salt, with an alkyl halide $R^{10}X$ (where $R^{10}$ and X are same as defined above) may be employed.

The reaction for obtaining the compound (19) from the compound (18) and the reaction for obtaining the compound (11-b) from the compound (19) are carried out in the same manner as that for obtaining the compound (15) from the compound (14) and that for obtaining the compound (11-a) from the compound (15) in the reaction scheme-4, respectively.

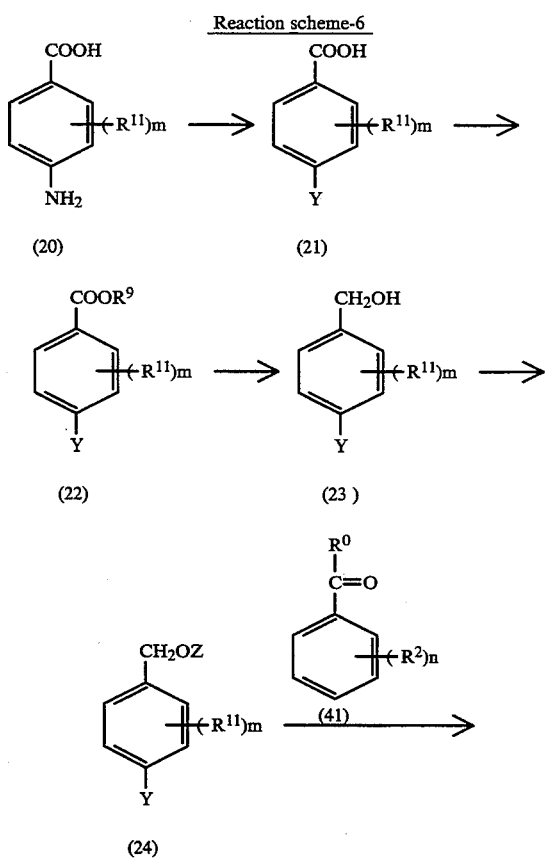

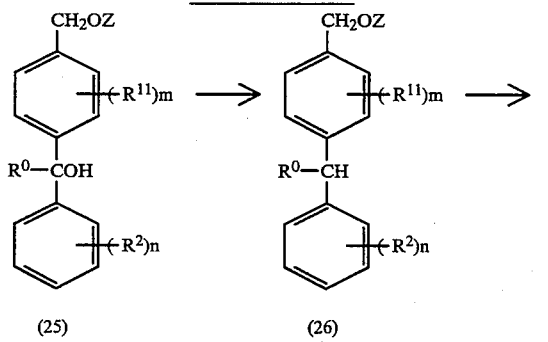

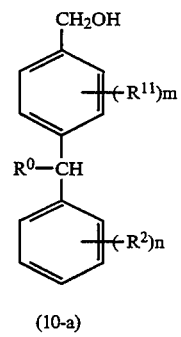

(where $R^0$, $R^2$, m, n, $R^9$ and Y are same as defined above, $R^{11}$ is a lower alkyl group, and z ia a protective group.)

This reaction scheme is suitably adapted to preparation of an intermediate for obtaining the compound of the invention in which $R^1$ in the general Formula (1) is alkyl group.

The reaction of the first step is composed of reacting the compound (20) with nitrous acid or its salt (e.g. sodium salt) to obtain a diazonium salt, substituting a diazo group into a halogen atom Y with copper(I) halide to obtain the compound (21), and esterifying the carboxy group in the same manner as mentioned above to obtain the compound (22). The reaction can be carried out in the same manner as that for obtaining the compound (14) from the compound (13) in the reaction scheme-4.

Then, the compound (22) is converted into the compound (23) by using the hydride-reducing agent. In this reaction, the available hydride reducing agent and reducing condition are the same agents and conditions as in the reducing reaction of the compound (11) to the compound (10) in the second step of the reaction scheme-3.

Next, the hydroxy group which is possessed in the compound (23) is protected by the protective group Z to obtain the compound (24). Examples of the protective group reacting with the compound (23) in order to protect the hydroxy group include t-butyl group, tetrahydropyran-1-yl group, t-butyldimethylsilyl group and the like. The reaction is carried out in a solvent or without a solvent, for example, if using any of the former two protective groups, in the presence of an acid such as 10 camphorsulfuric acid, toluenesulfonic acid and the like, and if using the latter protective group, in the presence of a base such as triethylamine, 4-dimethylaminopyridine (DMAP), imidazole and the like.

The compound (24) is reacted with a alkyl lithium (e.g. n-butyl lithium) under an inert atmosphere, and then is reacted with a carbonyl compound (41) to obtain the compound (25). These reactions are carried out in an inert solvent at a low temperature, usually from −60° C. to 0° C.

The compound (25) is reduced to the compound (26) under hydrogen atmosphere in the presence of a catalyst. Examples of the catalyst include palladium catalyst, platinum catalyst, rhodium catalyst and the like. The reaction can be carried out in a suitable solvent such as methanol, ethanol, ethyl acetate and the like, at a temperature from 0° C. to 100° C., and is terminated in about 30 minutes to 168 hours.

The compound (10-a) is obtained by eliminating the protective group from the compound (26) thus obtained. The elimination reaction is carried out in the presence of an acid in a suitable solvent such as methanol, ethanol and the like. Examples of the acid include hydrochloric acid, sulfuric acid, acetic acid, trifluoroacetic acid and the like. The reaction is carried out at a temperature from 0° C. to 50° C., for about 5 minutes to 10 hours.

As another method for obtaining the compound (10-a) from the compound (25), the following reaction may be used.

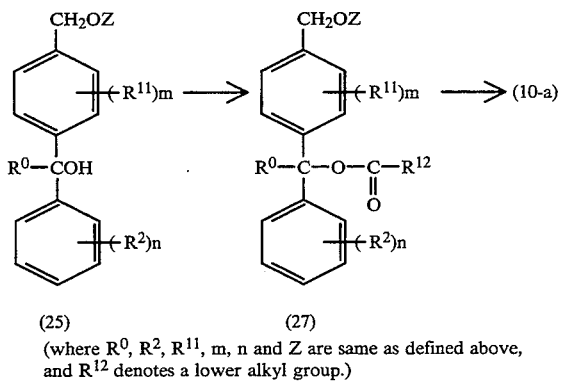

(where $R^0$, $R^2$, $R^{11}$, m, n and Z are same as defined above, and $R^{12}$ denotes a lower alkyl group.)

Specifically, this another method is composed of acylating the compound (25) to obtain the compound (27), and then reducing the compound (27) to obtain the compound (10-a).

The acylation is carried out by using an ordinal acylating agent. Examples of the acylating agent include lower alkanoyl halides such acetyl chloride, propionyl chloride and lower alkanoic acids such as acetic acid and propionic acid, lower alkanoic anhydrides such as acetic anhydride and the like. The acylating agent may be used at least equimolar amount to the compound (25), but usually is used from equimolar amount to an excessive amount to the compound (25).

When using lower alkanoyl halide as the acylating agent, it is preferred that the acylation is carried out in the presence of a basic compound in a suitable solvent. Examples of the available basic compound include organic bases such as triethylamine, trimethylamine, pyridine, dimethylaniline, N-methylmorpholine, 1,5-diazabicyclo[4,3,0]non-5-ene (DBN), 1,8-diazabicyclo[5,4,- 0]undec-7-ene (DBU), 1,4-diazabicyclo[2,2,2]octane (DABCO), potassium carbonate, sodium carbonate, potassium hydrogencarbonate, sodium hydrogencarbonate, sodium hydroxide, potassium hydroxide, sodium hydride, potassium hydride and the like. The molar ratio of the basic compound to the compound (25) is at least 1:1 to 3:1. Examples of the available solvent include halogenated hydrocarbons such as methylene chloride, chloroform, dichloroethane, aromatic hydrocarbons such as benzene, toluene and xylene, ethers such as diethylether, tetrahydrofuran and dimethoxyethane, esters such as ethyl acetate, non-protic polar solvents such as acetone, N,N-dimethylformamide, dimethylsulfoxide and hexamethylphosphoric triamide, pyridine, acetone and the like.

The reaction may be carried out at a temperature from 0° C. to 100° C., but is usually carried out at a temperature from 0° C. to 50° C. for about 30 minutes to 48 hours.

The reaction for obtaining the compound (10-a) from the compound (27) can be carried out in the same manner as in the reducing reaction for obtaining the compound (26) from the compound (25).

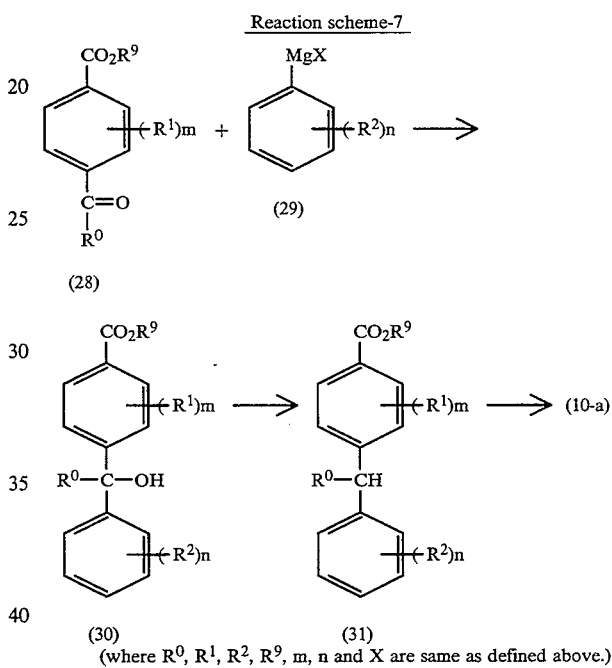

(where $R^0$, $R^1$, $R^2$, $R^9$, m, n and X are same as defined above.)

This reaction scheme is to obtain an intermediate of the compound of the invention by using Grignard reaction.

The reaction is carried out by adding the carbonyl compound (28) to a solution containing a Grignard reagent (29), and then stirring the mixture at a temperature from −10° C. to 0° C. for 10 minutes to 1 hour. The Grignard reagent (29) is obtained by reacting the corresponding halide compound with magnesium in a certain solvent. Examples of the solvent include anhydrous ethers such as tetrahydrofuran, dioxane, ether, and the like. It is suitable that the molar ratio of magnesium to the halogenide is about 1:1 to 1.5:1. The reaction is exothermic during process. After the reaction is completed, the reaction mixture is cooled to a a temperature from −10° C. to 0° C.

The reaction of the carbonyl compound (28) and the Grignard reagent (29) is carried out by adding the the carbonyl compound (28) to the reaction mixture where the Grignard reagent (29) is obtained.

After completion of the reaction, the resulting alcohol (30) is reduced to obtain the compound (31). The reduction is carried out in the same manner as in the reaction for reducing the compound (25) to the compound (26) in the reaction scheme-6. Alternatively, the another reaction for reducing the compound (11) to the compound (10-a) in second step of the reaction scheme-3 may be employed.

Reaction scheme-8

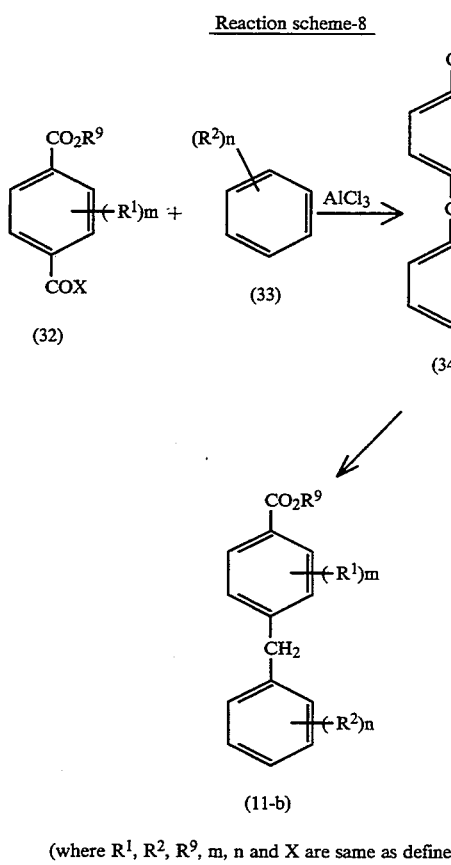

(where $R^1$, $R^2$, $R^9$, m, n and X are same as defined above.)

This reaction scheme is to obtain an intermediate of the compound of the invention by using Fridel-Crafts reaction.

First, an acyl halide derivative (32) and a benzene derivative (33) are mixed with each other at a molar ratio that the acyl halide derivative (32) to benzene derivative (33) is 1:4 to 1:5, in a solvent or without solvent, and then aluminium chloride is added to carry out the reaction. It is suitable that an amount of aluminium chloride to be added is about 3 to 5 times molar of the acyl halide derivative (32).

The reaction is carried out at a temperature from 10° C. to 25° C. for about 1 hour to 4 hours.

When "n" in the above reaction formula is 1, two isomers, where $R^2$ is substituted to o-position and p-position, respectively, are included. These isomers can be separated by using a means such as extraction. After separating each isomer, the reaction product (34) is reduced with sodium borohydride in trifluoroacetic acid to obtain the compound (11-a). When "n" is 2, the isomers are separated and reduced in the same manner as mentioned above. Besides, it is possible to introduce the lower alkyl group, which is $R^0$, to the ketone group in Formula (34) by using an ordinary method.

Instead of aluminium chloride mentioned-above, ferric chloride, zinc chloride, antimony pentachloride, tin tetrachloride, boron trifluoride, or the like is usable as the catalyst.

Reaction scheme-9

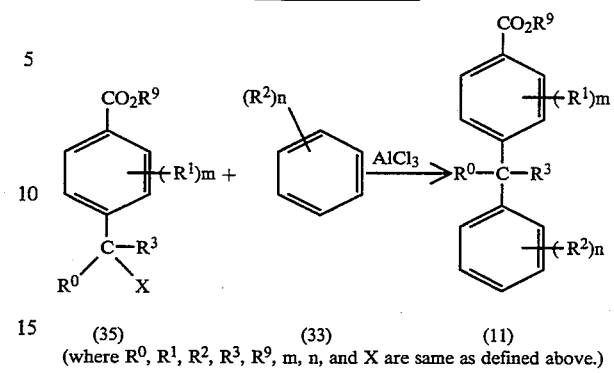

(where $R^0$, $R^1$, $R^2$, $R^3$, $R^9$, m, n, and X are same as defined above.)

This reaction is to obtain the compound (11) in accordance with Friedel-Crafts reaction by using a halide of Formula (35) instead of the acyl halide derivative (32) used in Reaction scheme-8. The others conditions are similar to Reaction scheme-8. In this reaction, the resulting compound (11) contains isomers, which are separable by recrystallization extraction or the like.

Reaction scheme-10

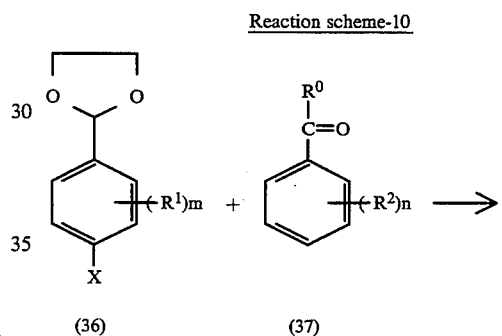

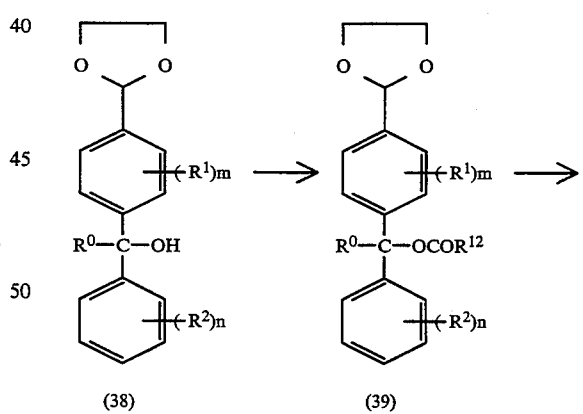

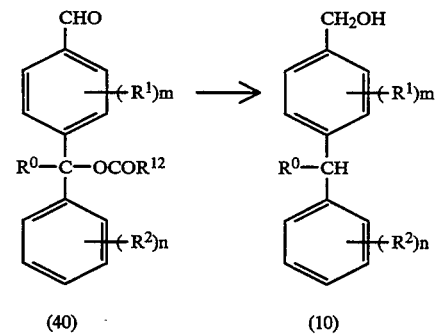

-continued
Reaction scheme-10
(where $R^0$, $R^1$, $R^2$, $R^{12}$, m, n, and X are same as defined above.)

This reaction scheme starts from the halide compound (36) of benzaldehyde-ethyleneacetal derivative (36) to obtain an intermediate of the compound of the invention.

In the first step of this reaction, from the halide compound of benzaldehyde-ethyleneacetal derivative (36), a Grignard reagent (29) is prepared, and is reacted with the benzaldehyde derivative (37) to obtain the compound (38). The reaction is carried out in the same manner as in Reaction scheme-7.

Next, the resulting compound (38) is acylated to obtain the compound (39). The reaction is carried out in the same manner as acylation reaction [i.e. reaction from (25) to (27)] in Reaction scheme-6. The product (39) is hydrolyzed to obtain the aldehyde derivative (40). This reaction can be carried out in the same manner as hydrolysis in (3) of Reaction scheme-2.

The product (40) is reduced to obtain the compound (10) mentioned above, which is the intermediate of the invention. This reaction can be carried out in the same manner as reduction from the compound (25) to the compound (26) in Reaction scheme-6.

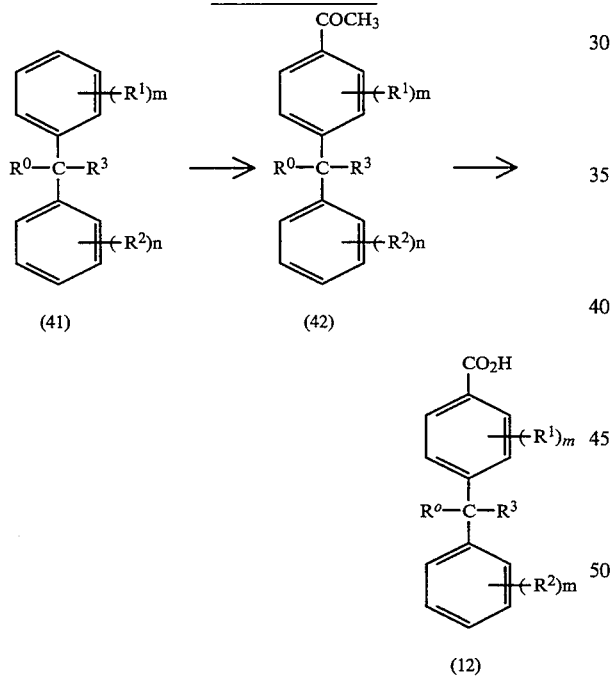

(where $R^0$, $R^1$, $R^2$, $R^3$, m, and n are same as defined above.)

This reaction scheme is to obtain the compound expressed in Formula (12) which is the starting material of the first step of reaction scheme-3.

First, an acetyl group is introduced to a benzene ring of the diphenylmethane derivative (41) by using Friedel-Crafts reaction. The reaction is carried out by mixing the diphenylmethane derivative (41) with acetyl chloride in a solvent or without solvent at a molar ratio that the diphenylmethane derivative (12) to acetyl chloride is in the range from 2:1 to 1:2, and adding anhydrous aluminium chloride. Examples of the solvent include chlorobenzene, nitrobenzene, carbon disulfide, methylene chloride and the like. The others are similar to Reaction scheme-8.

The 4-acetyldiphenylmethane derivative (42) thus obtained is reacted with a proper amount of halogen such as bromine and chlorine, in the presence of a base, in a solvent or without solvent to convert the acetyl group into a carboxy group, thereby obtaining the product (12). Examples of the base include sodium hydroxide, potassium hydroxide, sodium carbonate, potassium carbonate and the like. The reaction may be carried out at a temperature from 0° C. to 30° C., for 10 minutes to 6 hours.

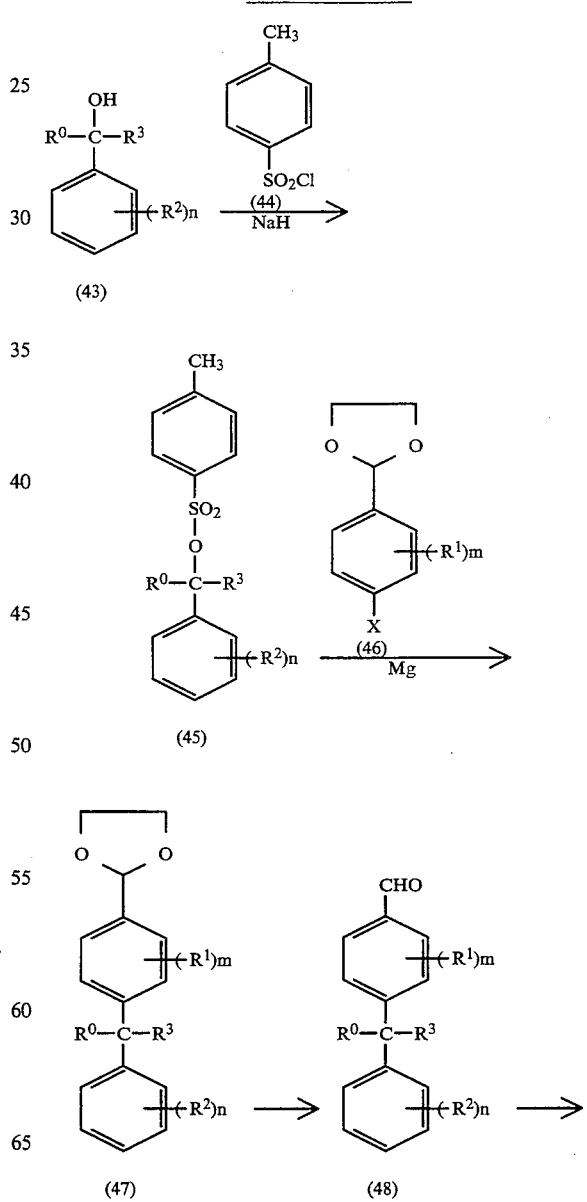

-continued
Reaction scheme-12

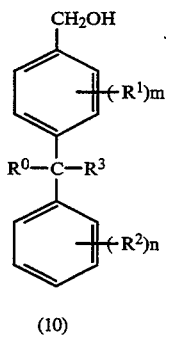

(10)

(where $R^0$, $R^1$, $R^2$, $R^3$, X, m and n are same as defined above.)

This reaction scheme is to obtain the intermediate of the compound of the invention (e.g. the compound (10) in the second step of reaction scheme-3).

In the first step, the benzylalcohol derivative (43) is put into the suspension of sodium hydride under an inert atmosphere. In that case, it is preferred that the benzylalcohol derivative (43) is used in the form of solution by previously dissolving it to the solvent identical with or compatible to the solvent used in the suspension of sodium hydride. Then, after cooling, tosylchloride (44) is put into it at an almost equimolar amount to sodium hydride, and is reacted at room temperature or its vicinity to obtain the benzyltosylate derivative expressed in Formula (45).

In the second step, benzaldehyde-ethyleneacetal halide (46) is reacted with the resulting benzyltosylate derivative (45). More specifically, to the solution that the benzyltosylate derivative (45) and copper (I) halide-dimethylsulfide complex are dissolved into an inert solvent is added the Grignard reagent prepared from benzaldehyde-ethyleneacetal halide (46) and magnesium, and is reacted at room temperature or heating, for 3 to 24 hours to obtain the compound (47).

In the third step, the ethylenedioxy group of the compound (47) is subjected to hydrolysis to convert into a formyl group, thereby obtaining the compound (48). The reaction may be carried out, in the presence of an acidic material such as hydrochloric acid, at room temperature or heating for 10 minutes to 2 hours.

In the fourth step, the formyl group of the compound (48) is reduced to obtain the compound (10) having a hydroxy group. The reaction is carried out by a proper hydrogenation-reducing agent. Examples of the suitable hydrogenation-reducing agent and reaction condition are almost similar to reduction in second step of the reaction scheme-3, for obtaining the compound (10) from the compound (11).

Reaction scheme-13

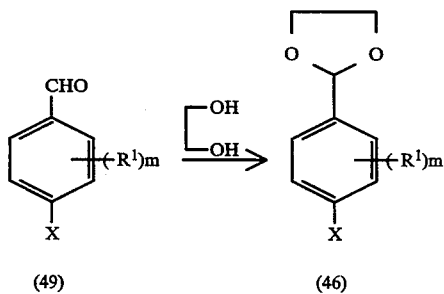

-continued
Reaction scheme-13

(where $R^1$, X and m are same as defined above.)

This reaction scheme is to obtain the benzaldehyde-ethyleneacetal halide (46) used in reaction scheme-12.

More specifically, the benzaldehyde derivative (49) and ethylene glycol are reacted with each other in the presence of an acid to obtain the benzaldehyde-ethyleneacetal halide (46). The reaction is carried out in a proper solvent (e.g. benzene) at a temperature from 80° C. to 110° C., for 1 hour to 5 hours. Examples of the acid are 10-camphorsulfonic acid and the like.

The compounds (1) can easily be converted into a salt thereof by treating them with a pharmaceutically available acid or base. The acid includes inorganic acids such as hydrochloric acid, sulfuric acid, phosphoric acid, hydrobromic acid and the like, and organic acid such as oxalic acid, maleic acid, fumaric acid, malic acid, tartaric acid, citric acid, lactic acid, benzoic acid, acetic acid, p-toluenesulfonic acid, ethanesulfonic acid and the like. The base includes metal hydroxides such as sodium hydroxide, potassium hydroxide, calcium hydroxide and the like, alkali metal carbonates or hydrogen carbonates such as sodium carbonate, sodium hydrogen carbonate, potassium hydrogen carbonate and the like.

The compounds (1) of the invention include also the optical isomers, the syn isomers and the anti isomer. These isomers can easily be separated by a conventional resolution method, for example, by using an optical resoluting agent, by a method using an enzyme, and the like.

The compounds (1) of the invention are usually used in the form of a usual pharmaceutical preparation. The pharmaceutical preparation can be prepared in admixture with conventional pharmaceutically acceptable diluents or carriers, such as fillers, bulking agent, binding agents, wetting agents, disintegrators, surfactants, lubricating agents and the like. The pharmaceutical prepation includes various preparations suitable for treatment of the diseases, for example, tablets, pills, powders, solutions, suspensions, emulsions, granules, capsules, suppositories, injections (solutions, suspensions, etc.) and the like, as well as medicines for external application such as lotions, creams, ointments and the like. In the preparation of tablets, there may be used any conventional carriers, for example, excipients such as lactose, white sugar, sodium chloride, glucose, urea, starches, calcium carbonate, kaolin, crystalline cellusose, silicate, etc.; binding agents such as water, ethanol, propanol, simple syrup, glucose solution, starch solution, gelatin solution, carboxymethyl cellulose, shellac, methyl cellulose, potassium phosphate, polyvinylpyrrolidone, etc.; disintegrators such as dry starch, sodium alginate, agar powder, laminaran powder, sodium hydrogencarbonate, calcium carbonate, polyoxyethylene sorbitan fatty acid esters, sodium laurylsulfate, stearic monoglyceride, starches, lactose, etc.; disintegration inhibitors such as white sugar, stearin, cacao butter, hydrogenated oils, etc.; absorption promoters such as quaternary ammonium salts, sodium laurylsulfate, etc.; wetting agents such as glycerin, starches, etc.; absorbents such as starches, lactose, kaolin, bentonite, colloidal silicates, etc.; rublicants such as purified talc, stearates, boric acid powder, polyethylene glycol, etc.; and the like. The tablets may also be coated with conventional coating agents, for example, may be in the form of a sugar coated tablet, a gelatin-coated tablets, an enteric coating tablet, a film coating tablet, or a double or multiple layers tablet.

In the preparation of pills, there may be used conventional carriers such as excipients (e.g. glucose, lactose, starches, cacao butter, hydrogenated vegetable oils, kaoline, talc, etc.), binding agents (e.g. gum arabic powder, tragacanth powder, gelatin, ethanol, etc.), disintegrators (e.g. laminaran, agar, etc.), and the like. In the preparation of suppositories, there may be used conventional carriers, such as polyethylene glycol, cacao butter, higher alcohols, higher alcohol esters, gelatin, semi-synthetized glycerides, and the like. In the preparation of injections, the solutions, emulsions or suspensions of the compounds are sterilized and are preferably made of isotonic with the body liquid. These solutions, emulsions and suspensions are prepared by admixing the active compound with a conventional diluent, such as water, ethyl alcohol, propylene glycol, ethoxylated isostearyl alcohol, polyoxylated isostraryl alcohol, polyoxyethylene sorbitan fatty acid esters, and the like. The preparation may also be incorporated with sodium chloride, glucose or glycerin in an amount sufficient to make them isotonic with the body liquid. The preparations may also be incorporated with conventional solubilizers, buffering agents, anesthetizing agents, and further, with coloring agents, preservatives, perfumes, flavors, sweeting agents, and other medicaments. The preparation in the form of a paste, cream or gel may be prepared by using, as a diluent, white vaseline, paraffin, glycerin, cellulose derivatives, polyethylene glycol, silicone, bentonite, or the like.

The condensed pyrazole derivatives (1) of the invention or its salts may be contained in any amount in the preparation, which can be selected from a wide range without limitation, and are usually contained in an amount of 1 to 70% by weight based on the whole weight of the preparations.

The pharmaceutical preparations of the invention can be administered in any methods. Suitable method for administration may be selected in accordance with the preparation form, age and sex of the patients, degree of severity of the diseases, and the like. For example, tablets, pills, solutions, suspensions, emulsions, granules and capsules are administered in oral route.

In case of injection, it is administered intravenously alone or together with an auxiliary liquid (e.g. glucose, amino acid solution, etc.). The injections may also be administered in intramuscular, intracutaneous, subcutaneius or intraperitoneal route. Suppositories are administered in intrarectal route.

The dosage of the pharmaceutical preparation of the invention may vary according to administration methods, age and sex of the patients, severity of the diseases and the like, but is usually in the range of about 1 to 100 mg, preferably 5 to 20 mg, of the compound of the invention or its salt per 1 kg of body weight of the patient per day. The preparation is usually administered by dividing into 2 to 4 times per day.

EXAMPLES

The present invention is illustrated by the following Reference Examples and Examples.

Reference Example 1

Preparation of ethyl 4-benzylbenzoate

By using 4-benzylbenzoic acid (211.58 g), ethanol (1.8 l) and concentrated sulfuric acid (20 ml), there was prepared the title compound (232.55 g).

NMR (CDCl$_3$) δ: 7.96 (d, J=8.35Hz, 2H), 7.1–7.9 (m, 7H), 4.35 (q, J=7.25Hz, 2H), 4.02 (s, 2H), 1.37 (t, J=7.25Hz, 3H)

Reference Example 2

Preparation of 4-benzylbenzyl alcohol

By using ethyl 4-benzylbenzoate (232.55 g), lithium aluminium hydride (23.00 g) and ether (1.3 l), there was prepared the title compound (181.47 g).

NMR (CDCl$_3$) δ: 7.1–7.3 (m, 9H), 4.64 (s, 2H), 3.97 (s, 2H)

Reference Example 3

Preparation of 4-benzylbenzyl chloride 4-benzylbenzyl alcohol (181.47 g) was dissolved into chloroform (100 ml), and thionyl chloride (66.8 ml) was added with stirring at a 0° C. After stirring at 0° C. for 4 hours, reaction mixture was concentrated under reduced pressure to give the title compound (198.34 g). This product was used in the subsequent procedure without purification.

NMR (CDCl$_3$) δ: 7.1–7.4 (m, 9H), 4.55 (s, 2H), 3.97 (s, 2H)

Reference Example 4

Preparation of 4-benzylphenylacetonitrile

To a solution of 4-benzylbenzyl chloride (198.34 g) in dimethylchloride (DMF) (50 ml) was added in turn sodium hydrogen carbonate (76.88 g) and sodium cyanide (56.07 g). In that case, the solution was cooled as occasion demands, since heat is slightly generated. After stirring at room temperature for 17 hours, DMF (100 ml) was further added. After stirring at room temperature for 67 hours, ethyl acetate (300 ml) was added, and the precipitate was filtered, washed with ethyl acetate (300 ml). The filtrate and the washings were combined, washed with saturated aqueouse sodium chloride solution (20 ml×4), dried over anhydrous sodium sulfate, concentrated under reduced pressure to give the title compound (189.69 g).

NMR (CDCl$_3$) δ: 7.1–7.3 (m, 9H), 3.97 (s, 2H), 3.69 (s, 2H)

Reference Example 5

Preparation of α-formyl-4-benzylphenylacetonitrile

To a suspension of sodium methoxide (64.26 g) in toluene (2.5 l) was added dropwise at 0° C. a mixture of ethyl formate (88.14 g) and 4-benzylphenylacetonitrile (189.69 g) with stirring. After 30 minutes, ice bath was removed. After 20 hours, ice water (2.6 l) was added to the reaction mixture, and the aqueous layer was separated. The organic layer was washed with 0.5N sodium hydroxide aqueous solution (500 ml×5). The aqueous layer and the washings were combined, adjusted to acid with conc. hydrochloric acid, and stirred at 0° C. for 30 minutes. The precipitate was separated by filtration, washed, and dried to give the title compound.(152.22 g).

On the other hand, the toluene layer was concentrated under reduced pressure, extracted with 0.5N sodium hydroxide aqueous solution. The extract was adjusted to acid with conc. hydrochloric acid. The precipitate was separated by filtration, washed with water, and dried to give the title compound (51.25 g).

NMR (DMSO-d$_6$) δ: 7.2–7.6 (m, 9H), 3.91 (bs, 2H)

Reference Example 6

Preparation of 3-amino-4-(4-benzylphenyl)-2-carbamoylpyrazole

A mixture of α-formyl-4-benzylphenylacetonitrile (152.22 g), semicarbazide hydrochloride (72.24 g), methanol (400 ml) and water (80 ml) was stirred at room temperature, and after 18 hours, maintained pH to about 10 with 5N sodium hydroxide aqueous solution. When heat was generated, the reaction mixture was cooled with ice-water. After stirring at room temperature for 1 hour, the reaction mixture was neutralized with 10% hydrochloric acid, and water (1 l) was added. After stirring for 1 hour, the precipitate was separated by filtration, washed with water, and dried to give the title compound (165.52 g).

NMR (DMSO-$d_6$) δ: 7.65 (s, 1H), 7.58 (bs, 2H), 7.39 (d, J=8.35Hz, 2H), 7.1–7.4 (m, 7H), 6.54 (bs, 2H), 3.92 (s, 2H)

Example 1

Preparation of 8-(4-benzylphenyl)-4-hydroxypyrazolo[1,5-a]-1,3,5-triazine

A mixture of 3-amino-4-(4-benzylphenyl)-2-carbamoylpyrazole (1.00 g), ethyl orthoformate (0.61 ml) and N,N-dimethylformamide (0.86 ml) was stirred at 100° C. to 110° C. for 45 minutes. To the reaction mixture was added ethyl acetate (20 ml). After stirring at room temperature for 30 minutes, the precipitate was separated by filtration, washed with ethyl acetate, and dried to give the title compound (0.72 g).

mp: 300°–303° C.

NMR (DMSO-$d_6$) δ: 8.51 (s, 1H), 8.07 (s, 1H), 7.92 (d, J=8.13Hz, 2H), 7.2–7.4 (m, 7H), 3.95 (s, 2H)

Reference Example 7

Preparation of 3-amino-4-(4-benzylphenyl)pyrazole

A mixture of 3-amino-4-(4-benzylphenyl)-2-carbamoylpyrazole (1.00 g), sodium hydroxide (1.00 g), methanol (40 ml) and water (40 ml) was stirred under heating reflux for 3.5 hours, and ice-water was added.

The mixture was extracted with chloroform, washed with water, dried over Glauber's salt, and concentrated under reduced pressure to give the title compound (0.77 g).

mp: 127°–129.5° C.

NMR (DMSO-$d_6$) δ: 11.61 (bs, 1H), 7.57 (s, 1H), 7.40 (d, J=8.57Hz, 2H), 7.1–7.3 (m, 5H), 7.16 (d, J=8.57Hz, 2H), 4.64 (bs, 2H), 3.90 (s, 2H)

Reference Example 8

Preparation of 3-(4-benzylphenyl)-6-ethoxycarbonyl-7-hydroxypyrazolo[1,5-a]pyrimidine A mixture of 3-amino-4-(4-benzylphenyl)pyrazole (0.75 g), ethoxymethylenemalonic diethylester (1.30 g) and ethanol (30 ml) was stirred under heating reflux for 48 hours. After cooling, sodium ethoxide -ethanol was added, and was stirred at room temperature for 12 hours. Then, at 0° C., 10% hydrochloric acid was added to adjust to acid, and water (50 ml) was added and stirred for 30 minutes. The precipitate was separated by filtration, washed with water, and dried to give the title compound (1.12 g).

mp: 258°–260.5° C. (decomposed)

NMR (DMSO-$d_6$) δ: 8.34 (s, 1H), 8.19 (s, 1H), 7.52 (d, J=8.57Hz, 2H), 7.2–7.5 (m, 7H), 4.25 (q, J=7.04Hz, 2H), 3.99 (s, 2H), 1.29 (t, J=7.04Hz, 3H)

Reference Example 9

Preparation of 3-(4-benzylphenyl)-6-carboxy-7-hydroxypyrazolo[1,5-a]pyrimidine

A mixture of 3-(4-benzylphenyl)-6-ethoxycarbonyl-7-hydroxypyrazolo[1,5-a]pyrimidine (1.35 g), sodium hydroxide (1.50 g), ethanol (35 ml) and water (35 ml) was stirred under heating reflux for 2 hours. Then, to the reaction mixture was added water (50 ml), and hydrochloric acid was added at 0° C. to adjust to acid. After stirring for 30 minutes, the precipitate was separated by filtration, washed with water, and dried to give the title compound (1.24 g).

NMR (DMSO-$d_6$) δ: 8.43 (s, 1H), 8.30 (s, 1H), 7.55 (d, J=7.91Hz, 2H), 7.1–7.5 (m, 7H), 3.98 (s, 2H)

Example 2

Preparation of 3-(4-benzylphenyl)-7-hydroxypyrazolo[1,5-a]pyrimidine

A mixture of 3-(4-benzylphenyl)-6-carboxy-7-hydroxypyrazolo[1,5-a]pyrimidine (1.24 g) and aniline (11 ml) was stirred at 100° C. to 110° C. for 7 hours, and ice-water was put into the reaction mixture. After adding hydrochloric acid to adjust to acid, the reaction mixture was stirred at 0° C. for 1 hour. The precipitate was separated by filtration, washed with methanol-water (1:3)(50 ml), and dried to give the title compound (0.90 g).

mp: 276°–281° C. (decomposed)

NMR (DMSO-$d_6$) δ: 8.15 (s, 1H), 7.78 (d, J=7.57Hz, 1H), 7.50 (d, J=8.13Hz, 2H), 7.10 (d, J=8.13Hz, 2H), 7.2–7.4 (m, 5H), 5.76 (d, J=7.25Hz, 1H), 3.98 (s, 2H)

Example 3

Preparation of 8-(4-benzyl-3-chloro)phenyl-4-hydroxypyrazolo[1,5-a]-1,3,5-triazine In the same manner as in Example 1, there are prepared the title compound.

mp: >300° C.

NMR (DMSO-$d_6$) δ: 8.62 (s, 1H), 8.15 (s, 2H), 7.92 (dd, J=7.9, 1.3Hz, 1H), 7.39 (d, J=7.9Hz, 1H), 7.16–7.30 (m, 6H), 4.09 (s, 2H)

Example 4

Preparation of 8-(4-benzyl-3-methoxy)phenyl-4-hydroxypyrazolo[1,5-a]-1,3,5-triazine In the same manner as in Example 1, there are prepared the title compound.

mp: 264°–271° C.

NMR (DMSO-$d_6$) δ: 8.59 (s, 1H), 8.10 (s, 1H), 7.50–7.62 (m, 2H), 7.10–7.25 (m, 6H), 3.91 (s, 2H), 3.85 (s, 3H)

Example 5

Preparation of 8-(4-benzyl-3-methyl)phenyl-4-hydroxypyrazolo[1,5-a]-1,3,5-triazine In the same manner as in Example 1, there are prepared the title compound.

mp: >300° C.

NMR (DMSO-$d_6$) δ: 8.52 (s, 1H), 8.09 (s, 1H), 7.70–7.90 (m, 2H), 7.14–7.27 (m, 6H), 3.97 (s, 2H), 2.25 (s, 3H)

Reference Example 10

(1) Preparation of methyl 4-methyl-3-chlorobenzoate

To 4-methyl-3-aminobenzoic acid (7.5 g, 0.05 mol) was added conc. hydrochloric acid (50 ml). The obtained suspension was ice-cooled, and a solution obtained by dissolving sodium nitrite (4 g, 0.05 mol) in water (20 ml) was added. After 30 minutes, copper(I) chloride (5.5 g, 0.055 mol) was added, and the reaction mixture was stirred at room temperature for 1 hour, and further stirred at 100° C. for 1 hour. After allowing to cool, the precipitate was separated by filtration, washed with water, and dried. It was suspended in 90 ml of methanol, and conc. sulfuric acid (2.6 ml) was added. After refluxing under heating for 4 hours, the reaction mixture was allowed to cool, and methanol was distilled away under reduced pressure. To the residue was added a saturated aqueous sodium hydrogencarbonate solution, and the reaction mixture was extracted with ethyl acetate, and after washing with water and a saturated aqueous sodium chloride solution, was dried over anhydrous sodium sulfate. After distilling the solvent away, the residue was separated and purified by using a silica-gel column chromatography (ethyl acetate:n-hexane=1:5) to give the title compound (5.8 g, 0.03 mol) (yield 60%).

(2) Preparation of methyl 4-bromomethyl-3-chlorobenzoate

Methyl 4-methyl-3-chlorobenzoate (4.5 g, 0.024 mol) was dissolved in carbon tetrachloride (100 ml), and thereto were added N-bromosuccinimide (4.8 g, 0.026 mol) and a catalytic amount of perbenzoic anhydride. The mixture was heated and refluxed under nitrogen atmosphere for 2 hours, allowed to cool, and the precipitate was separated by filtration. The filtrate was concentrated, and separated and purified by using a silica-gel column chromatography (ethyl acetate:n-hexane=1:20) to give the title compound (4.7 g, 0.018 mol) (yield 75%).

NMR (CDCl$_3$) δ: 8.04 (s, 1H), 7.91 (bd, J=8.13Hz, 1H), 7.50 (d, J=7.92Hz, 1H), 4.58 (s, 2H), 3.92 (s, 3H)

(3) Preparation of methyl 4-benzyl-3-chlorobenzoate

4-Bromomethyl-3-chlorobenzoate (4.7 g, 0.018 mol) was dissolved in 50 ml of benzene, and thereto was added anhyrous aluminium chloride (4.7 g, 0.036 mol). After stirring at room temperature for 3 hours, the reaction liquid was poured into an ice-water and was extracted with ethyl acetate. After washing with saturated aqueous sodium chloride solution, the organic layer was dried over anhydrous sodium sulfate, and the solvent was distilled away. The residue was separated and purified by using a silica-gel column chromatography (ethyl acetate:n-hexane=1:10) to give the title compound (4.6 g, 0.017 mol).

NMR (CDCl$_3$) δ: 8.05 (d, J=1.76Hz, 1H), 7.83 (d, d, J=7.91Hz, 1.76Hz, 1H), 7.1–7.4 (m, 6H), 4.14 (s, 2H), 3.90 (s, 3 H)

Hereinafter, in the same manner as in Reference Examples 2 to 6 by using the product thus obtained, there is obtained the starting material in Example 3.

Reference Example 11

(1) Preparation of methyl 4-methyl-3-methoxybenzoate

To 4-methyl-3-methoxybenzoic acid (7.5 g, 0.05 mol) was added 8 ml of conc. sulfuric acid, and thereto was added water (100 ml). Under ice-cooling, a solution obtained by dissolving sodium nitrite (4 g, 0.05 mol) in water (20 ml) was added. The reaction mixture was stirred at room temperature for 14 hours, and heated at 60° C. for 1 hour. After allowing to cool, the precipitate was separated by filtration, washed with water and dried.

The precipitate was dissolved in methanol (50 ml), and thereto was added conc. sulfuric acid (2.3 ml).

After heating and refluxing for 1 hour, the reaction liquid was allowed to cool, and methanol was distilled away. To the residue was added saturated aqueous sodium hydrogencarbonate, and the precipitate was separated by filtration, washed with water and dried.

The product was dissolved in acetone (50 ml), and thereto were added potassium carbonate (3.7 g, 0.22 mol) and dimethyl sulfate (2.7 ml, 0.022 mol), and the mixture was heated and refluxed for 2.5 hours.

After allowing to cool, the insoluble material was separated by filtration, and acetone was distilled away under reduced pressure. To the residue was added 10% hydrochloric acid, and the mixture was extracted with ethyl acetate. After washing with water and saturated aqueous sodium chloride solution, the organic layer was dried over anhydrous sodium sulfate. After distilling the solvent away, the residue was separated and purified by using a silica-gel column chromatography (ethyl acetate:n-hexane=1:15) to give the title compound (3.8 g, 0.021 mol).

NMR (CDCl$_3$) δ: 7.4–7.6 (m, 2H), 7.17 (d, J=7.47Hz, 1H), 3.90 (s, 3H), 3.88 (s, 3H), 2.26 (s, 3H)

(2) Preparation of methyl 4-benzyl-3-methoxybenzoate

Methyl 4-methyl-3-methoxybenzoate (3.8 g, 0.021 mol) was dissolved in carbon tetrachloride (80 ml), and thereto were added N-bromosuccinimide (4.3 g, 0.021 mol) and a catalytic amount of perbenzoic anhydride, and the mixture was heated and refluxed under nitrogen atmosphere for 3 hours.

After allowing to cool, the insoluble material was separated by filtration, and the filtrate was concentrated. The residue was dissolved in 60 ml of benzene, and thereto was added anhydrous aluminium chloride (8.3 g, 0.062 mol), and the mixture was stirred at room temperature for 2.5 hours. Next, the reaction liquid was poured into ice-water, and was extracted with ethyl acetate. After washing water and saturated aqueous sodium chloride solution, the organic layer was dried over anhydrous sodium sulfate. After distilling the solvent away, the residue was separated and purified by using a silica-gel column chromatography (ethyl acetate:n-hexane=1:10), and the obtained fractions were recrystallized from ethyl acetate-n-hexane. The recrystallized substance was separated by filtration, and the filtrate was concentrated to give the title compound.

The recrystallized substance was recrystallized again, and the filtrate was concentrated, and was combined with the above concentrated filtrate, so that the title compound (4 g, 0.016 mol) was obtained.

NMR (CDCl$_3$) δ: 7.5–7.6 (m, 2H), 7.1–7.3 (m, 5H), 7.10 (d, J=8.13Hz, 1H), 4.00 (s, 2H), 3.89 (s, 3H), 3.87 (s, 3H)

Hereinafter, in the same manner as in Reference Examples 2 to 6 by using the product thus obtained, there is obtained the starting material in Example 4.

Reference Example 12

(1) Preparation of ethyl 4-bromo-3-methylbenzoate

To an aqueous solution of 47% hydrobromic acid (60 ml) and water (60 ml) was added 4-amino-3-methylbenzoic acid (10 g, 0.066 mol), and the mixture was stirred at room temperature for 2 hours. After ice-cooling, a solution obtained by dissolving sodium nitrite (5.3 g, 0.066 mol) in water (25 ml) was added, and the mixture was stirred for 2 hours as it was.

To the mixture was added copper(I) chloride (10 g, 0.07 mol) was added, and the mixture was stirred at room temperature for 15 hours. The precipitate was separated by filtration, washed with water, and dried to give 4-bromo-3-methylbenzoic acid.

This product was dissolved in ethanol (100 ml), and thereto was added conc. 3 ml of sulfuric acid, and the mixture was heated and refluxed for 24 hours. After allowing to cool, ethanol was distilled away, and to the residue was added saturated aqueous sodium hydrogencarbonate solution, and the mixture was extracted with ethyl acetate. After washing with water and saturated aqueous sodium chloride solution, the extract was dried over anhydrous sodium sulfate, and the solvent was distilled away. The residue was separated and purified by using a silica-gel column chromatography (ethyl acetate:n-hexane=1:5) to give the title compound (14 g, 0.058 mol).

(2) Preparation of 4-bromo-3-methylbenzyl alcohol

Ethyl 4-bromo-3-methylbenzoate (14 g, 0.058 mol) was dissolved in ether (200 ml). Under ice-cooling, to the obtained solution was added lithium aluminium hydride (1.8 g, 0.046 mol) little by little, and under this state, the mixture was stirred for 1 hour. After decomposing excessive lithium aluminium hydride with ethyl acetate, water and 10% hydrochloric acid were added, and the mixture was extracted with ethyl acetate. After washing with water and saturated aqueous sodium chloride solution, the extract was dried over anhydrous sodium sulfate, and the solvent was distilled away. The residue was separated and purified by using a column chromatography (ethyl acetate:n-hexane=1:3) to give the title compound (10.6 g, 0.053 mol).

(3) Preparation of 2-(4-bromo-3-methylbenzyloxy)tetrahydropyran 4-bromo-3-methylbenzyl alcohol (2 g, 0.01 mol) was dissolved in methylene chloride (10 ml). Under ice-cooling, to the obtained solution was added 3,4-dihydropyran (1 ml, 0.011 mol) and 10-camphorsulfonic acid (120 mg, 0.5 millimol), and the mixture was stirred at room temperature for 1.5 hours. After diluting with methylene chloride, the mixture was washed with saturated aqueous sodium hydrogencarbonate solution, water and saturated aqueous sodium chloride solution. After drying over anhydrous sodium sulfate, the solvent was distilled away, and the residue was separated and purified by using a silica-gel column chromatography (ethyl acetate:n-hexane=1:3) to give the title compound (2.8 g, 0.01 mol).

NMR (CDCl$_3$) δ: 7.49 (d, J=8.13Hz, 1H), 7.23 (d, J=1.54Hz, 1H), 7.04 (d, d, J=8.13Hz, 1.54Hz, 1H), 4.72 (d, J=12.09Hz, 1H), 4.41 (d, J=12.09Hz, 1H), 3.6–4.1 (m, 1H), 3.4–3.6 (m, 1H), 2.40 (s, 3H), 1.5–1.8 (m, 8H)

(4) Preparation of 2-(4-phenylhydroxymethyl-3-methylbenzyloxy) tetrahydropyran 2-(4-Bromo-3-methylbenzyloxy)tetrahydropyran (1.4 g, 5 millimol) was dissolved in tetrahydrofuran (5 ml), and cooled to −20° C. with methanol-water. Under nitrogen atmosphere, thereto was added 15% hexane solution (5 ml) of n-butyllithium, and in this state, the mixture was stirred for 30 minutes. Next, benzaldehyde (0.6 ml, 6 millimol) was added, and stirred for 2 hours. During this procedure, inner-temperature was raised from −20° C. to 30° C. Then, water was added, and the mixture was extracted with ethyl acetate. After washing with water and saturated aqueous sodium chloride solution, the solvent was distilled away, and the residue was separated and purified by using a silica-gel column chromatography (ethyl acetate:n-hexane=1:5 to 1:2) to give the title compound (0.9 g, 2.9 millimol).

NMR (CDCl$_3$) δ: 7.47 (d, J=7.91Hz, 1H), 7.1–7.4 (m, 7H), 5.97 (s, 1H), 4.75 (d, J=11.86Hz, 1H), 4.43 (d, J=11.87Hz, 1H), 4.6–4.8 (m, 1H), 3.7–4.1 (m, 1H), 3.3–3.7 (m, 1H), 2.24 (s, 3H), 1.4–1.9 (m, 6H)

(5) Preparation of 2-(4-benzyl-3-methylbenzyloxy)tetrahydropyran 2-(4-Phenylhydroxymethyl-3-methylbenzyloxy)tetrahydropyran (2.5 g, 8 millimol) was dissolved in ethanol (20 ml). 5%-palladium carbon was added at a catalytic amount, and stirred at room temperature under hydrogen atmosphere for 6 days. After the insoluble material was distilled away, the filtrate was concentrated, and the residue was separated and purified by using a silica-gel column chromatography (ethyl acetate:n-hexane=1:3) to give the title compound (1.65 g, 5.6 millimol).

NMR (CDCl$_3$) δ: 7.0–7.5 (m, 8H), 4.75 (d, J=11.64Hz, 1H), 4.42 (d, J=11.65Hz, 1H), 4.6–4.8 (m, 1H), 3.97 (s, 2H), 3.8–4.0 (m, 1H), 3.4–3.6 (m, 1H), 2.24 (s, 3H), 1.4–1.8 (m, 6H)

(6) Preparation of 4-benzyl-3-methylbenzyl alcohol 2-(4-benzyl-3-methylbenzyloxy)tetrahydropyran (2.9 g, 0.01 mol) was dissolved in methanol (50 ml). To the obtained solution was added 10% hydrochloric acid (10 ml), and the mixture was stirred at room temperature for 1 hour. After distilling methanol, saturated aqueous sodium chloride solution was added, and the mixture was extracted with ethyl acetate. After washing with saturated aqueous sodium hydrogencarbonate solution, water and saturated aqueous sodium chloride solution, the extract was dried over anhydrous sodium sulfate, and the solvent was distilled away to give the title compound (2.2 g, 0.01 mol).

NMR (CDCl$_3$) δ: 7.0–7.4 (m, 8H), 4.64 (s, 2H), 3.98 (s, 2H), 2.25 (s, 3H)

Hereinafter, in the same manner as in Reference Examples 3 to 6 by using the product thus obtained, there is obtained the starting material in Example 5.

Reference Example 13

(1) Preparation of 2,4'-dimethoxy-4-ethoxycarbonylbenzhydrol

To tetrahydrofuran (10 ml) were added magnesium (0.25 g, 10 millimol) and a small amount of iodine. Next, under nitrogen atmosphere, thereto was added 4-bromoanisole (1.2 ml, 9.5 millimol), and the mixture was vigorously stirred.

Magnesium was dissolved with generating heat. At the time that the major part of magnesium was dissolved, and heat generation was terminated, the reaction liquid was cooled with methanol-water (−20 ° C.).

To this mixture was added ethyl 3-methoxy-4-formylbenzoate (1.8 g, 8.64 millimol) immediately, and the mixture was stirred at the same temperature for 30 minutes. After adding saturated aqueous ammonium chloride solution, the reaction liquid was returned to room temperature, and extracted with ethyl acetate. The organic layer was washed with water, dried over anhydrous sodium sulfate, and the solvent was distilled away.

The residue was separated and purified by using a silica-gel column chromatography (ethyl acetate:n-hexane=3:8) to give the title compound (2.21 g, 7 millimol, 70%).

NMR (CDCl$_3$) δ: 7.66 (dd, J=6.9, 1.6Hz, 1H), 7.68 (d, J=1.3Hz, 1H), 7.42 (d, J=7.9Hz, 1H), 7.27 (dd, J=6.6, 2.0Hz, 2H), 6.85 (dd, J=6.6Hz, 2.0Hz, 2H), 6.04 (d, J=4.5Hz, 1H), 4.37 (q, J=6.3Hz, 2H), 3.85 (s, 3H), 3.79 (s, 3H), 2.77 (d, J=5.0Hz, 1H), 1.39 (t, J=6.3Hz, 3H)

(2) Preparation of ethyl 3-methoxy-4-(4-methoxyphenylmethyl)benzoate 2,4'-dimethoxy-4-ethoxycarbonyl-benzhydrol (2.21 g, 7 millimol) was dissolved in ethanol (30 ml), and thereto was added a catalytic amount of 20% palladium hydroxide-carbon.

The mixture was stirred at room temperature under hydrogen atmosphere for 16 hours. After diluting with ethyl acetate, the catalyst was separated by filtration, and the solvent was distilled away to give the title compound (1.91 g, 6.4 millimol, 91%), NMR (CDCl$_3$) δ: 7.57 (dd, J=7.6, 1.7Hz, 1H), 7.52 (d, J=1.3Hz, 1H), 7.08-7.12 (m, 3H), 6.81 (dd, J=6.6, 2.3Hz, 2H), 4.36 (q, J=6.9Hz, 2H), 3.94 (s, 2H), 3.88 (s, 3H), 3.78 (s, 3H), 1.38 (t, J=6.9Hz, 3H)

(3) Preparation of 2,4'-dimethoxy-4-hydroxymethyl-diphenylmethane

Ethyl 3-methoxy-4-(4-methoxyphenylmethyl)benzoate (1.91 g, 6.4 millimol) was dissolved in ethyl ether (20 ml), and ice-cooled. Lithium aluminium hydride (250 mg, 6.5 millimol) was added, and in this state, stirred for 1 hour. After decomposing excessive lithium aluminium hydride with ethyl acetate, water and 10% hydrochloric acid were added, and the reaction mixture was extracted with ethyl acetate. After washing with water, the extract was dried over anhydrous sodium sulfate, and the solvent was distilled away to give the title compound (1.64 g, 6.4 millimol, 100%).

NMR (CDCl$_3$) δ: 7.11 (d, J=8.9Hz, 2H), 7.02 (d, J=7.6Hz, 1H), 6.90 (s, 1H), 6.79-6.86 (m, 3H), 4.65 (s, 2H), 3.89 (s, 2H), 3.83 (s, 3H), 3.77 (s, 3H)

(4) Preparation of 4-chloromethyl-2,4'-dimethoxydiphenylmethane 2,4'-Dimethoxy-4-hydroxymethyl-diphenylmethane (1.64 g, 6.4 millimol) was dissolved in tetrahydrofuran (20 ml), and thereto were added triphenylphosphine (2.52 g, 9.6 millimol) and carbon tetrachloride (8 ml). Under nitrogen atmosphere, the mixture was heated and refluxed for 2 hours, and after allowing to cool, separated and purified by using a silica-gel column chromatography (ethyl acetate:n-hexane=1:5) to give the title compound (1.75 g, 6.4 millimol, 100%).

NMR (CDCl$_3$) δ: 7.11 (dd, J=6.6, 2.3Hz, 2H), 7.01 (d, J=7.9Hz, 1H), 6.83-6.89 (m, 4H), 4.56 (s, 2H), 3.89 (s, 2H), 3.84 (s, 3H), 3.78 (s, 3H)

(5) Preparation of 3-methoxy-4-(4-methoxyphenylmethyl)phenylacetonitrile

4-Chloromethyl-2,4'-dimethoxydiphenylmethane (1.75 g, 6.4 millimol) was dissolved in dimethylformamide (6 ml), and thereto were added sodium cyanide (0.4 g, 7.8 millimol), and the mixture was stirred at room temperature for 15 hours.

The reaction liquid was diluted with ethyl acetate, and an insoluble material was separated by filtration. The filtrate was washed with water, and dried over anhydrous sodium sulfate. Next, the solvent was distilled away to give the title compound (1.66 g, 6.3 millimol, 98%).

NMR (CDCl$_3$) δ: 7.10 (dd, J=6.6, 2.3Hz, 2H), 7.03 (d, J=7.9Hz, 1H), 6.80-6.83 (m, 4H), 3.88 (s, 2H), 3.84 (s, 3H), 3.77 (s, 3H), 3.71 (s, 2H)

Example 6

Preparation of 4-hydroxy-8-[3-methoxy-4-(4-methoxyphenylmethyl) phenylpyrazolo[1,5-a]-1,3,5-triazine 3-Methoxy-4-(4-methoxyphenylmethyl)-phenylacetonitrile (1.66 g, 6.3 millimol) was dissolved in benzene (50 ml), and thereto were added ethyl formate (0.9 ml) and sodium methoxide (1.3 g, 24 millimol), and the mixture was vigorously stirred at room temperature. After 4 hours, water and 10% hydrochloric acid were added, and the mixture was extracted with ethyl acetate. The reaction liquid was washed with water, dried over anhydrous sodium sulfate, and the solvent was distilled away. The residue was dissolved in methanol (20 ml).

Thereto was added an aqueous solution obtained by dissolving semicarbazide hydrochloride (0.9 g, 8 millimol) in water (4 ml), and the mixture was stirred at room temperature for 15 hours.

The reaction liquid was cooled with ice, and thereto was added 2N-NaOH till showing alkaline. Next, the reaction liquid was returned to room temperature, and stirred for 30 minutes. Again, the reaction liquid was cooled with ice, neutralized with 10% hydrochloric acid, diluted with water, and insoluble substance was distilled away. After washing with water, the filtrate was dried at 60° C. under reduced pressure.

In the same manner as in Example 1, 3-amino-4-[3-methoxy-4-(4-methoxyphenyl)methyl]phenyl-2-carbamoylpyrazole thus obtained was suspended in dimethylformamide (3 ml), and thereto was added ethyl orthoformate (1.5 ml), and the mixture was heated and refluxed at 100° C. to 110° C. for 3 hours.

After allowing to cool, the reaction liquid was diluted with ethyl acetate, and insoluble substance was separated by filtration. The product was washed with ethyl acetate and ether, and dried to give the title compound (1 g, 2.8 millimol, 44%).

NMR (DMSO-d$_6$) δ: 8.60 (s, 1H), 8.12 (s, 1H), 7.62 (d, J=1.3Hz, 1H), 7.54 (dd, J=7.9, 1.7Hz, 1H); 7.13 (d, J=7.6Hz, 1H), 7.12 (dd, J=6.6, 2.3Hz, 2H), 6.82 (dd, J=6.9, 2.3Hz, 2H), 3.85 (s, 3H), 3.83 (s, 2H), 3.70 (s, 3H)
mp 280°-283° C.

Reference Example 14

(1) Preparation of 4-ethoxycarbonyl-2-methoxy-2'-methylbenzhydrol

In the same manner as in Reference Example 13, there was prepared the title compound.

NMR (CDCl$_3$) δ: 7.60 (dd, J=7.9, 1.7Hz, 1H), 7.56 (d, J=1.3Hz, 1H), 7.38-7.41 (m, 1H), 7.15-7.22 (m, 4H), 6.30 (s, 1H), 4.37 (q, J=6.9Hz, 2H), 3.90 (s, 3H), 2.75 (bs, 1H), 2.27 (s, 3H), 1.38 (t, J=6.9Hz, 3H)

(2) Preparation of ethyl 3-methoxy-4-(2-methylphenylmethyl)benzoate

In the same manner as in Reference Example 13, there was prepared the title compound.

NMR (CDCl$_3$) δ: 7.54 (s, 1H), 7.53 (dd, J=6.9, 1.7Hz, 1H), 7.11-7.26 (m, 3H), 7.03 (dd, J=5.9, 2.3Hz, 1H), 6.87 (d, J=8.3Hz, 1H), 4.37 (q, J=6.9Hz, 2H), 3.97 (s, 2H), 3.90 (s, 3H), 2.23 (s, 3H), 1.38 (t, J=6.9Hz, 3H)

(3) Preparation of 4-hydroxymethyl-2-methoxy-2'-methyldiphenylmethane

In the same manner as in Reference Example 13, there was prepared the title compound.

NMR (CDCl$_3$) δ: 7.09-7.18 (m, 3H), 7.01-7.04 (m, 1H), 6.93 (s, 1H), 6.80 (d, J=1.0Hz, 2H), 4.66 (s, 2H), 3.93 (s, 2H), 3.85 (s, 3H), 2.25 (s, 3H)

(4) Preparation of 4-chloromethyl-2-methoxy-2'-methyldiphenylmethane

In the same manner as in Reference Example 13, there was prepared the title compound.

NMR (CDCl₃) δ: 7.14–7.18 (m, 3H), 7.03–7.11 (m, 1H), 6.92 (s, 1H), 6.79–6.88 (m, 2H), 4.59 (s, 2H), 3.94 (s, 2H), 3.88 (s, 3H), 2.26 (s, 3H)

(5) Preparation of 3-methoxy-4-(2-methylphenylmethyl)phenylacetonitrile

In the same manner as in Reference Example 13, there was prepared the title compound.

NMR (CDCl₃) δ: 7.16–7.19 (m, 3H), 7.01–7.15 (m, 1H), 6.76–6.88 (m, 3H), 3.93 (s, 2H), 3.87 (s, 3H), 3.67 (s, 2H), 2.25 (s, 3H)

Example 7

Preparation of 4-hydroxy-8-[3-methoxy-4-(2-methylphenylmethyl) phenylpyrazolo[1,5-a]-1,3,5-triazine In the same manner as in Example 6, by using 3-methoxy-4-(2-methylphenylmethyl)phenylacetonitrile, there was prepared the title compound.

mp: 282°–285° C.

NMR (DMSO-d₆) δ: 8.61 (s, 1H), 8.12 (s, 1H), 7.65 (d, J=1.3Hz, 1H), 7.52 (dd, J=7.9, 1.6Hz, 1H), 7.09–7.17 (m, 3H), 6.98–7.01 (m, 1H), 6.90 (d, J=7.9 Hz, 1H), 3.88 (s, 2H), 3.86 (s, 3H), 2.23 (s, 3H)

Reference Example 15

(1) Preparation of 4-ethoxycarbonyl-2-methoxy-4'-methylbenzhydrol

In the same manner as in Reference Example 13, there was prepared the title compound.

NMR (CDCl₃) δ: 7.66 (dd, J=7.9, 1.7Hz, 1H), 7.53 (d, J=1.3Hz, 1H), 7.42 (d, J=8.1Hz, 1H), 7.25 (d, J=7.9, Hz, 2H), 7.12 (d, J=7.9Hz, 2H), 6.05 (d, J=5.0Hz, 1H), 4.37 (q, J=7.3Hz, 2H), 3.86 (s, 3H), 2.80 (d, J=5.3Hz, 1H), 2.33 (s, 3H), 1.39 (t, J=7.3Hz, 3H)

(2) Preparation of ethyl 3-methoxy-4-(4-methylphenylmethyl)benzoate

In the same manner as in Reference Example 13, there was prepared the title compound.

NMR (CDCl₃) δ: 7.56 (dd, J=7.9, 1.7Hz, 1H), 7.52 (d, J=1.5Hz, 1H), 7.06–7.11 (m, 5H), 4.36 (q, J=6.9Hz, 2H), 3.96 (s, 2H), 3.88 (s, 3H), 2.31 (s, 3H), 1.38 (t, J=6.9Hz, 3H)

(3) Preparation of 4-hydroxymethyl-2-methoxy-4'-methyldiphenylmethane

In the same manner as in Reference Example 13, there was prepared the title compound.

NMR (CDCl₃) δ: 7.02–7.11 (m, 5H), 6.83–6.90 (m, 2H), 4.65 (s, 2H), 3.92 (s, 2H), 3.83 (s, 3H), 2.30 (s, 3H)

(4) Preparation of 4-chloromethyl-2-methoxy-4'-methyldiphenylmethane

In the same manner as in Reference Example 13, there was prepared the title compound.

NMR (CDCl₃) δ: 7.00–7.08 (m, 5H), 6.85–6.88 (m, 2H), 4.56 (s, 2H), 3.91 (s, 2H), 3.84 (s, 3H), 2.31 (s, 3H)

(5) Preparation of 3-methoxy-4-(4-methylphenylmethyl)phenylacetonitrile

In the same manner as in Reference Example 13, there was prepared the title compound.

Example 8

Preparation of 4-hydroxy-8-[3-methoxy-4-(4-methylphenylmethyl) phenylpyrazolo[1,5-a]-1,3,5-triazine In the same manner as in Example 6, by using 3-methoxy-4-(4-methylphenylmethyl)phenylacetonitrile, there was prepared the title compound.

mp: 265°–270° C.

NMR (DMSO-d₆) δ: 8.61 (s, 1H), 8.12 (s, 1H), 7.61 (d, J=1.4Hz, 1H), 7.54 (dd, J=7.7, 1.6Hz, 1H), 7.07–7.15 (m, 5H), 3.85 (s, 2H), 3.84 (s, 3H), 2.24 (s, 3H)

Reference Example 16

(1) Preparation of 2.2'-dimethoxy-4-ethoxycarbonylbenzhydrol

In the same manner as in Reference Example 13, there was prepared the title compound.

NMR (CDCl₃) δ: 7.65 (dd, J=8.0, 1.6Hz, 1H), 7.55 (d, J=1.6Hz, 1H), 7.38 (d, J=7.9Hz, 1H), 7.23–7.30 (m, 1H), 7.15 (dd, J=7.3, 1.6Hz, 1H), 6.91 (t, J=7.6Hz, 2H), 6.34 (d, J=5.3Hz, 1H), 4.38 (q, J=7.2Hz, 2H), 3.86 (s, 3H), 3.83 (s, 3H), 3.51 (t, J=5.6Hz, 1H), 1.39 (t, J=7.2Hz, 3H)

(2) Preparation of ethyl 3-methoxy-4-(2-methoxyphenylmethyl)benzoate

In the same manner as in Reference Example 13, there was prepared the title compound.

NMR (CDCl₃) δ: 7.53–7.56 (m, 2H), 7.17–7.24 (m, 1H), 7.01–7.06 (m, 2H), 6.83–6.89 (m, 2H), 4.36 (q, J=7.2, Hz, 2H), 3.99 (s, 2H), 3.89 (s, 3H), 3.80 (s, 3H), 1.38 (t, J=7.2Hz, 3H)

(3) Preparation of 3-methoxy-4-(2-methoxyphenylmethyl)acetonitrile

In the same manner as in Reference Example 13, there was prepared the title compound.

NMR (CDCl₃) δ: 7.16–7.22 (m, 1H), 6.98–7.04 (m, 2H), 6.76–6.89 (m, 4H), 3.93 (s, 2H), 3.84 (s, 3H), 3.81 (s, 3H), 3.70 (s, 2H)

Example 9

Preparation of 4-hydroxy-8-[3-methoxy-4-(2-methoxyphenylmethyl) phenylpyrazolo[1,5-a]-1,3,5-triazine In the same manner as in Example 6, by using 3-methoxy-4-(2-methoxyphenylmethyl)acetonitrile, there was prepared the title compound.

mp: 255°–258° C.

NMR (DMSO-d₆) δ: 8.61 (s, 1H), 8.12 (s, 1H), 7.63 (d, J=1.3Hz, 1H), 7.51 (dd, J=7.9, 1.7Hz, 1H), 7.16–7.22 (m, 1H), 6.93–7.00 (m, 3H), 6.81–6.86 (m, 1H) 3.85 (s, 5H, overlapped), 3.79 (s, 3H)

Reference Example 17

(1) Preparation of 3'-methoxy-4-(tetrahydropyran-2-yloxymethyl)-2-methylbenzhydrol To tetrahydrofuran (30 ml) were added magnesium (1 g, 41 millimol) and a small amount of iodine, and under nitrogen atmosphere, thereto was added 2-bromo-5-(tetrahydropyran-2-yloxy)methyl-toluene (8.4 g, 30 millimol), and the mixture was heated and refluxed. After 1.5 hours, the reaction liquid was cooled with ice, and thereto was added 3-methoxybenzealdehyde (3.6 ml, 30 millimol), and stirred at room temperature for 2 hours.

Next, to the reaction liquid was added saturated aqueous aluminium chloride solution, and the mixture was extracted with ethyl acetate. The organic layer was washed with water, dried over anhydrous sodium sulfate, and the solvent was separated by filtration. The residue was separated and purified by using a silica-gel column chromatography (ethyl acetate:n-hexane=1:2) to give the title compound (3.8 g, 11 millimol).

NMR (CDCl₃) δ: 7.46 (d, J=7.9, Hz, 1H), 7.15–7.26 (m, 4H), 6.78–6.90 (m, 2H), 5.96 (s, 1H), 4.75 (d, J=11.9Hz, 1H), 4.65–4.72 (m, 1H) 4.45 (d, J=12.1Hz, 1H), 3.88–3.92 (m, 1H), 3.77 (s, 3H), 3.52–3.56 (m, 1H), 2.16 (bs, 1H), 1.56–1.85 (m, 6H)

(2) Preparation of 3'-methoxy-4-(tetrahydropyran-2-yloxymethyl)-2-methyldiphenylmethane 3'-Methoxy-4-(tetrahydropyran-2-yloxymethyl)-2-methylbenzhydrol (4 g, 11.7 millimol) was dissolved in ethanol (50 ml). After adding a catalytic amount of 5% palladium carbon, the mixture was stirred at room temperature under hydrogen atmosphere for 90 hours.

After separating palladium carbon by filtration, the solvent was distilled away, and the residue was separated and purified by using a silica-gel column chromatography (ethyl acetate:n-hexane=1:5) to give the title compound (1.2 g, 3.7 millimol, 32%).

NMR (CDCl$_3$) δ: 7.10–7.21 (m, 4H), 6.67–6.75 (m, 3H), 4.75 (d, J=11.6Hz, 1H), 4.47–4.72 (m, 1H), 4.44 (d, J=11.9Hz, 1H), 3.89–3.98 (m, 1H), 3.76 (s, 3H), 3.51–3.59 (m, 1H), 2.24 (s, 3H), 1.23–1.90 (m, 6H)

(3) Preparation of 4-chloromethyl-2-methyl-3'-methoxydiphenylmethane

3'-Methoxy-4-(tetrahydropyran-2-yloxymethyl)-2-methyldiphenylmethane (1.4 g, 4.3 millimol) was dissolved in methanol (10 ml), and thereto was added 10% hydrochloric acid (2 ml), and the mixture was stirred at room temperature.

After 1 hour, to the mixture was added saturated aqueous sodium hydrogencarbonate, and the mixture was extructed with ethyl acetate, and after washing with water, dried over anhydrous sodium sulfate. The residue was dissolved in tetrahydrofuran (15 ml). To the obtained solution were added triphenylphosphine (1.7 g, 6.5 millimol) and carbon tetrachloride (4.3 ml, 44.5 millimol). The mixture was heated and refluxed under nitrogen atmosphere for 19 hours. After allowing to cool, the product was separated and purified by using a silica-gel column chromatography (ethyl acetate:n-hexane=1:5) to give the title compound (1.1 g, 4.3 millimol).

NMR (CDCl$_3$) δ: 7.07–7.25 (m, 4H), 6.66–6.76 (m, 3H), 4.55 (s, 2H), 3.95 (s, 2H), 3.76 (s, 3H), 2.25 (s, 3H)

(4) Preparation of 4-(3-methoxyphenylmethyl)-3-methylphenylacetonitrile

In the same manner as in Reference Example 13, there was prepared the title compound.

NMR (CDCl$_3$) δ: 7.10–7.22 (m, 4H), 6.64–6.76 (m, 3H), 3.95 (s, 2H), 3.76 (s, 3H), 3.69 (s, 2H), 2.25 (s, 3H)

Example 10

Preparation of 4-hydroxy-8-[4-(3-methoxyphenylmethyl)-3-methyl]phenylpyrazolo[1,5-a]-1,3,5-triazine In the same manner as in Example 6, by using 4-(3-methoxyphenylmethyl)-3-methylphenylacetonitrile, there was prepared the title compound.

mp: 227°–229° C.

NMR (DMSO-d$_6$) δ: 8.55 (s, 1H), 8.11 (s, 1H), 7.83 (s, 1H), 7.79 (dd, J=7.6, 1.6Hz, 1H), 7.17–7.23 (m, 2H), 6.70–6.78 (m, 3H), 3.94 (s, 2H), 3.70 (s, 3H), 2.25 (m, 3H)

Reference Example 18

(1) Preparation of 2,3'-dimethoxy-4-(tetrahydropyran-2-yloxymethyl) benzhydrol

In the same manner as in Reference Example 17, there was prepared the title compound.

NMR (CDCl$_3$) δ: 7.19 (t, J=8.3Hz, 2H), 6.91–6.99 (m, 4H), 6.80 (d, J=2.6Hz, 1H), 6.02 (s, 1H), 4.76 (d, J=11.9Hz, 1H), 4.69 (t, J=3.3Hz, 1H), 4.48 (d, J=11.9Hz, 1H), 3.84–3.90 (m, 1H), 3.83 (s, 3H), 3.79 (s, 3H), 3.50–3.60 (m, 1H), 3.00 (bs, 1H), 1.56–1.85 (m, 6H)

(2) Preparation of 2,3'-dimethoxy-4-(tetrahydropyran-2-yloxymethyl) diphenylmethane In the same manner as in Reference Example 17, there was prepared the title compound.

7.17 (t, J=8.0Hz, 1H), 7.03 (d, J=7.6Hz, 1H), 6.70–6.88 (m, 5H), 4.75 (d, J=11.9Hz, 1H), 4.70 (t, J=3.0Hz, 1H), 4.47 (d, J=11.9Hz, 1H), 3.89–3.95 (m, 1H), 3.93 (s, 2H), 3.83 (s, 3H), 3.77 (s, 3H), 3.52–3.57 (m, 1H), 1.51–1.86 (m, 6H)

The tetrahydropyran-2-yl group which was protective group of hydroxy group was removed from the above product to give 2,3'-dimethoxy-4-hydroxymethyl-diphenylmethane.

NMR (CDCl$_3$) δ: 7.18 (t, J=7.6Hz, 1H), 7.05 (d, J=7.6Hz, 1 H), 6.91 (s, 1H), 6.70–6.86 (m, 4H), 4.66 (s, 2H), 3.93 (s, 2H), 3.84 (s, 3H), 3.76 (s, 3H)

Hereinafter, in the same manner as in Reference Example 17, there was prepared 4-(3-methoxyphenylmethyl)-3-methoxyphenylacetonitrile.

Example 11

Preparation of 4-hydroxy-8-[3-methoxy-4-(3-methoxyphenylmethyl) phenylpyrazolo[1,5-a]-1,3,5-triazine In the same manner as in Example 6, by using 4-(3-methoxyphenylmethyl)-3-methoxyphenylacetonitrile, there was prepared the title compound.

mp: 260°–262° C.

NMR (DMSO-d$_6$) δ: 8.61 (s, 1H), 8.12 (s, 1H), 7.63 (d, J=1.7Hz, 1H), 7.55 (dd, J=8.6, 1.4Hz, 1H), 7.14–7.20 (m, 2H), 6.72–6.79 (m, 3H), 3.88 (s, 2H), 3.86 (s, 3H), 3.71 (s, 3H)

Reference Example 19

(1) Preparation of 2-methoxy-3'-methyl-4-(tetrahydropyran-2-yloxymethyl) benzhydrol In the same manner as in Reference Example 17, there was prepared the title compound.

NMR (CDCl$_3$) δ: 7.14–7.23 (m, 4H), 7.05 (d, J=6.9Hz, 1H), 6.91–6.94 (m, 2H), 6.02 (s, 1H), 4.76 (d, J=11.9Hz, 1H), 4.66–4.70 (m, 1H), 4.49 (d, J=11.9Hz, 1H), 3.88–3.96 (m, 1H), 3.83 (s, 3H), 3.50–3.58 (m, 1H), 2.95 (bs, 1H), 2.33 (s, 3H), 1.51–1.89 (m, 6H)

(2) Preparation of 2-methoxy-3'-methyl-4-(tetrahydropyran-2-yloxymethyl) diphenylmethane In the same manner as in Reference Example 17, there was prepared the title compound, NMR (CDCl$_3$) δ: 7.14 (t, J=7.6Hz, 1H), 6.97–7.03 (m, 4H), 6.85–6.88 (m, 2H), 4.76 (d, J=11.9Hz, 1H), 4.70 (t, J=3.0Hz, 1H), 4.47 (d, J=11.9Hz, 1H), 3.89–3.96 (m, 1H), 3.91 (s, 2H), 3.83 (s, 3H), 3.52–3.59 (m, 1H), 2.30 (s, 3H), 1.51–1.86 (m, 6H)

The tetrahydropyran-2-yl group which was protective group of hydroxy group was removed from the above product to give 2-methoxy-3'-methyl-4-hydroxymethyl-diphenylmethane, NMR (CDCl$_3$) δ: 7.15 (t, J=7.6Hz, 1H), 6.98–7.05 (m, 4H), 6.91 (s, 1H), 6.85 (dd, J=7.6, 1.7Hz, 1H), 4.66 (s, 2H), 3.92 (s, 2H), 3.84 (s, 3H), 2.30 (s, 3H)

Hereinafter, in the same manner as in Reference Example 17, there was prepared 4-(3-methylphenylmethyl)-3-methoxyphenylacetonitrile.

Example 12

Preparation of 4-hydroxy-8-[3-methoxy-4-(3-methylphenylmethyl) phenylpyrazolo[1,5-a]-1,3,5-triazine In the same manner as in Example 6, by using 4-(3-methylphenylmethyl)-3-methoxyphenylacetonitrile, there was prepared the title compound.

mp: 267°–269° C.

NMR (DMSO-d$_6$) δ: 8.60 (s, 1H), 8.12 (s, 1H), 7.62 (d, J=1.3Hz, 1H), 7.54 (dd, J=7.6, 1.3Hz, 1H), 7.12–7.16

(m, 2H), 6.98–7.01 (m, 3H), 3.87 (s, 2H), 3.85 (s, 3H), 2.25 (s, 3H)

Reference Example 20

(1) Preparation of 4-methoxycarbonyl-3'-methylbenzhydrol

A mixture of m-bromotoluene (8.00 g), magnesium metal (1.2 g) and tetrahydrofuran (20 ml) was heated under nitrogen atmosphere by using a dryer. At the time that the reaction was initiated, heating was terminated, and the mixture was stirred till generation of heat was ended, and further heated and refluxed for 1 hour. The reaction mixture was cooled to 0° C., and ethyl terephthalaldehydate (4.6 g) was added under stirring. After stirring at 0° C. for 5 minutes, to the mixture were added saturated aqueous ammonium chloride solution (50 ml) and water (100 ml), and the mixture was extracted with ethyl acetate. The extract was washed with water, saturated sodium hydrogen carbonate solution and saturated aqueous sodium chloride solution, dried over anhydrous magnesium sulfate, and concentrated under reduced pressure. The residue was separated and purified by using a silica-gel column chromatography (ethyl acetate:n-hexane=1:5) to give the title compound (8.80 g).

NMR (CDCl$_3$) δ: 7.80 (d, J=8.23Hz, 2H), 7.47 (d, J=8.23Hz, 2H), 7.21–7.26 (m, 1H), 7.08–7.16 (m, 3H), 5.85 (s, 1H), 3.90 (s, 3H), 2.33 (s, 3H)

(2) Preparation of 4-methoxycarbonyl-3'-methyldiphenylmethane

To a solution of the product obtained in the step (1) in ethanol (50 ml) was added a catalytic amount of 20% paradium hydroxide carbon (50 ml). The mixture was stirred at room temperature and ordinary pressure under hydrogen atmosphere for 12 hours. The catalyst was separated by filtration, and the filtrate was concentrated. The residue was separated and purified by using a column chromatography (diethyl ether:n-hexane=1:20) to give the title compound (7.6 g).

NMR (CDCl$_3$) δ: 7.63 (d, J=8.23Hz, 2H), 7.15–7.27 (m, 3H), 6.96–7.04 (m, 3H), 3.99 (s, 2H), 3.89 (s, 3H), 2.31 (s, 3H)

(3) Preparation of 4-hydroxymethyl-3'-methyldiphenylmethane

To a suspension of lithium aluminium hydride (1.78 g) in diethyl ether (50 ml) was added dropwise a solution of the product (7.5 g) obtained in the step (2) in diethylether (100 ml) under ice-cooling. After dropping, the mixture was stirred at 0° C. for 1 hour. Excessive lithium aluminium hydride was decomposed with ethyl acetate (100 ml), water was added, and the mixture was extracted with ethyl acetate. The extract was washed with 10% aqueous sulfuric acid solution, saturated sodium hydrogencarbonate solution and saturated aqueous sodium chloride solution, dried over anhydrous magnesium sulfate, and the solvent was distilled away. The residue was separated and purified by using a silica-gel column chromatography (ethyl acetate:n-hexane=1:5) to give the title compound (5.7 g).

NMR (CDCl$_3$) δ: 7.25–7.30 (m, 2H), 7.14–7.20 (m, 8H), 6.97–7.08 (m, 3H), 4.65 (s, 2H), 3.94 (s, 2H), 2.31 (s, 3H)

(4) Preparation of 4-chloromethyl-3'-methyldiphenylmethane

To a solution of the product (5.6 g) obtained in the step (3) in chloroform (50 ml) was added dropwise a solution of thionyl chloride (2.3 ml) in chloroform (5 ml) at 0° C. under stirring. After dropping, the mixture was stirred at 0° C. for 1 hour. Next, water (100 ml) was added, and excessive thionyl chloride was decomposed, and the reaction liquid was extracted with chloroform. The extract was washed with water, saturated sodium hydrogencarbonate solution and saturated aqueous sodium chloride solution, dried over anhydrous magnesium sulfate, and the solvent was distilled away to give the title compound (6.0 g).

NMR (CDCl$_3$) δ: 7.25–7.31 (m, 2H), 7.15–7.20 (m, 3H), 6.96–7.03 (m, 3H), 4.56 (s, 2H), 3.93 (s, 2H), 2.31 (s, 3H)

(5) Preparation of 4-(3-methylphenylmethyl)-phenylacetonitrile

To a solution of the product (6.0 g) obtained in the step (4) in N,N-dimethylformamide (20 ml) was added sodium cyanide (1.47 g), and the mixture was stirred at room temperature for 13 hours. To the mixture was added ethyl acetate (150 ml), and the mixture was stirred at room temperature for 1 hour. The precipitate was separated by filtration, and the filtrate was washed with water and saturated aqueous sodium chloride solution, dried over anhydrous magnesium sulfate. Next, the solvent was distilled away to give the title compound (5.8 g).

NMR (CDCl$_3$) δ: 7.15–7.25 (m, 5H), 6.95–7.03 (m, 3H), 3.93 (s, 2H), 3.70 (s, 2H), 2.31 (s, 3H)

Example 13

Preparation of 4-hydroxy-8-[4-(3-methylphenylmethyl)phenyl]pyrazolo[1,5-a]-1,3,5-triazine To a suspention of sodium methoxide (2.8 g) in benzene (100 ml) were added dropwise a mixture of ethyl formate (2.4 ml) and the product (5.8 g) obtained in the step (5) of Reference Example 20 under stirring on ice-cooling.

After 15 minutes, ice bath was removed. After 2 hours, to the mixture was added ice-water (100 ml) and diethyl ether (200 ml). The water layer was separated, and the organic layer was washed with 0.5N sodium hydroxide aqueous solution. The water layer and the washings were combined, and the mixture was adjusted to pH 3 to 4 with conc. hydrochloric acid, and extracted with ethyl acetate. The extract was washed with water and saturated aqueous sodium chloride solution, dried over anhydrous magnesium sulfate. Next, the solvent was distilled away to give α-formyl-4-(3-methylphenylmethyl)phenylacetonitrile. The product was used in subsequent procedure without purification.

To a solution obtained by dissolving α-formyl-4-(3-methylphenylmethyl)phenylacetonitrile thus obtained in methanol (50 ml) and water (10 ml) was added semicarbazide hydrochloride (3.2 g) under stirring on ice-cooling. Ice bath was removed, and after 13 hours, the mixture was adjusted to alkaline (pH 10 to 11) with 5N-sodium hydroxide aqueous solution, and stirred for 1 hour. Next, the reaction mixture was neutralized (pH 8 to 9) with 10% hydrochloric acid aqueous solution, and the precipitate was separated by filtration. By washing and drying, 3-amino-2-carbamoyl-4-{4-(3-methylphenylmethyl)phenyl}pyrazole (6.3 g) was obtained. The product was used in subsequent procedure without purification.

A mixture of 3-amino-2-carbamoyl-4-{4-(3-methylphenylmethyl) phenyl}pyrazole (3.0 g), ethyl orthoformate (2 ml) and N,N-dimethylformamide (4 ml) was heated and stirred at 100° C. to 110° C. After 1 hour, to the mixture was added ethyl acetate (50 ml). The precipitate was separated by filtration, washed with ethyl acetate, dried to give the title compound (2.0 g).

mp: 271°–278° C.

NMR (DMSO-d$_6$) δ: 8.49 (s, 1H), 8.08 (s, 1H), 7.91 (d, J=8.24Hz, 2H), 7.26 (d, J=8.24Hz, 2H), 7.11–7.22 (m, 1H), 6.94–7.09 (m, 3H), 3.91 (s, 2H), 2.27 (s, 3H)

Reference Example 21

(1) Preparation of methyl 4-(2-methylphenylmethyl)-benzoate

In the same manner as in Reference Example 20, there was prepared the title compound.

NMR (CDCl$_3$) δ: 7.94 (d, J=8.26Hz, 2H), 7.14–7.20 (m, 5H), 7.08–7.11 (m, 1H), 4.03 (s, 2H), 3.89 (s, 3H), 2.21 (s, 3H)

(2) Preparation of 4-hydroxyethyl-2'-methyldiphenylmethane

In the same manner as in Reference Example 20, there was prepared the title compound.

NMR (CDCl$_3$) δ: 7.27 (d, J=8.56Hz, 2H), 7.08–7.18 (m, 6H), 4.65 (s, 2H), 3.98 (s, 2H), 2.24 (s, 3H)

(3) Preparation of 4-chloromethyl-2'-methyldiphenylmethane

In the same manner as in Reference Example 20, there was prepared the title compound.

NMR (CDCl$_3$) δ: 7.25–7.30 (m, 2H), 7.07–7.17 (m, 6H), 4.56 (s, 2H), 3.98 (s, 2H), 2.23 (s, 3H)

(4) Preparation of 4-(2-methylphenylmethyl)-phenylacetonitrile

In the same manner as in Reference Example 20, there was prepared the title compound.

NMR (CDCl$_3$) δ: 7.17–7.26 (m, 2H), 7.08–7.17 (m, 6H), 3.98 (s, 2H), 3.71 (s, 2H), 2.22 (s, 3H)

Example 14

Preparation of 4-hydroxy-8-[4-(2-methylphenylmethyl)phenyl]pyrazolo[1,5-a]-1,3,5-triazine In the same manner as in Example 13, by using 4-(2-methylphenylmethyl)phenylacetonitrile, there was prepared the title compound.

mp: 274°–279° C.

NMR (DMSO-d$_6$) δ: 8.48 (s, 1H), 8.07 (s, 1H), 7.91 (d, J=8.26Hz, 2H), 7.14 (d, J=8.26Hz, 2H), 7.05–7.29 (m, 4H), 3.97 (s, 2H), 2.23 (s, 3H)

Reference Example 22

(1) Preparation of 3-methoxy-4'-methoxycarbonylbenzhydrol

In the same manner as in Reference Example 20, there was prepared the title compound.

NMR (CDCl$_3$) δ: 8.00 (d, J=8.23Hz, 2H), 7.47 (d, J=8.23Hz, 2H), 7.23–7.29 (m, 1H), 6.91–6.94 (m, 2H), 6.80–6.87 (m, 1H), 5.85 (s, 1H), 3.90 (s, 3H), 3.78 (s, 3H)

(2) Preparation of methyl 4-(3-methoxyphenylmethyl)-benzoate

In the same manner as in Reference Example 20, there was prepared the title compound.

NMR (CDCl$_3$) δ: 7.91–7.97 (m, 2H), 7.15–7.26 (m, 3H), 6.71–6.78 (m, 3H), 3.99 (s, 2H), 3.89 (s, 3H), 3.76 (s, 3H)

(3) Preparation of 4-hydroxymethyl-3'-methoxydiphenylmethane

In the same manner as in Reference Example 20, there was prepared the title compound.

NMR (CDCl$_3$) δ: 7.25–7.30 (m, 2H), 7.17–7.23 (m, 3H), 6.69–6.79 (m, 3H), 4.66 (s, 2H), 3.95 (s, 2H), 3.77 (s, 3H)

(4) Preparation of 4-chloromethyl-3'-methoxydiphenylmethane

In the same manner as in Reference Example 20, there was prepared the title compound.

NMR (CDCl$_3$) δ: 7.23–7.32 (m, 2H), 7.13–7.20 (m, 3H), 6.71–6.78 (m, 3H), 4.56 (s, 2H), 3.95 (s, 2H), 3.77 (s, 3H)

(5) Preparation of 4-(3-methoxyphenylmethyl)-phenylacetonitrile

In the same manner as in Reference Example 20, there was prepared the title compound.

NMR (CDCl$_3$) δ: 7.18–7.25 (m, 5H), 6.71–6.77 (m, 3H), 3.94 (s, 2H), 3.77 (s, 3H), 3.70 (s, 2H)

Example 15

Preparation of 4-hydroxy-8-[4-(3-methoxyphenylmethyl)phenyl]pyrazolo[1,5-a]-1,3,5-triazine In the same manner as in Example 13, by using 4-(3-methoxyphenylmethyl)phenylacetonitrile, there was prepared the title compound.

mp: 264°–268° C.

NMR (DMSO-d$_6$) δ: 8.49 (s, 1H), 8.07 (s, 1H), 7.92 (d, J=8.24Hz, 2H), 7.27 (d, J=8.24Hz, 2H), 7.13–7.23 (m, 1H), 6.69–6.86 (m, 3H), 3.92 (s, 2H), 3.73 (s, 3H)

Reference Example 23

(1) Preparation of 4-hydroxymethyl-4'-methyldiphenylmethane

In the same manner as in Reference Example 20, there was prepared the title compound.

NMR (CDCl$_3$) δ: 7.27 (d, J=8.24Hz, 2H), 7.17 (d, J=8.24Hz, 2H), 7.04–7.11 (m, 4H), 4.64 (S, 2H), 3.93 (s, 2H), 2.31 (s, 3H)

(2) Preparation of 4-chloromethyl-4'-methyldiphenylmethane

In the same manner as in Reference Example 20, there was prepared the title compound.

NMR (CDCl$_3$) δ: 7.25–7.36 (m, 2H), 7.17 (d, J=7.91Hz, 2H), 7.04–7.11 (m, 4H), 4.55 (s, 2H), 3.93 (s, 2H), 2.31 (s, 3H)

(3) Preparation of 4-(4'-methylphenylmethyl)-phenylacetonitrile

In the same manner as in Reference Example 20, there was prepared the title compound.

NMR (CDCl$_3$) δ: 7.18–7.25 (m, 4H), 7.03–7.12 (m, 4H), 3.93 (s, 2H), 3.67 (s, 2H), 2.31 (s, 3H)

Example 16

Preparation of 4-hydroxy-8-[4-(4-methylphenylmethyl)phenyl]pyrazolo[1,5-a]-1,3,5-triazine In the same manner as in Example 13, by using 4-(4'-methylphenylmethyl)phenylacetonitrile, there was prepared the title compound.

mp: 285°–292° C.

NMR (DMSO-d$_6$) δ: 8.47 (s, 1H), 8.06 (s, 1H), 7.90 (d, J=8.24Hz, 2H), 7.25 (d, J=8.24Hz, 2H), 7.02–7.19 (m, 4H), 3.90 (s, 2H), 2.26 (s, 2H)

Reference Example 24

(1) Preparation of 4-methoxycarbonyl-2'-methoxybenzophenone

To a mixture of anisole (216 g) and terephtalic acid-methyl ester-chloride (99 g) was added aluminium chloride (200 g) at 0° C. in an amount of ⅓ to ¼ at a time. In that case, temperature was kept to 25° C. or less, and it took from 45 minutes to 1 hour for addition. The temperature returned to room temperature after 30 minutes from termination of addition, and after stirring for 1.5 hours to 2 hours, the pink colored precipitate was obtained by pouring ice-water. The precipitate was separated by filtration, dried with water and washed with methanol. Methanol washings were concentrated under reduced pressure, and washed with a small amount of methanol to give the title compound.

NMR (CDCl$_3$) δ: 8.09 (d, J=8.58Hz, 2H), 7.82 (d, J=8.79Hz, 2H), 7.35–7.65 (m, 2H), 6.95–7.20 (m, 2H), 3.94 (s, 3H), 3.69 (s, 3H)

Reference Example 25

(1) Preparation of 4-methoxycarbonyl-4'-methoxybenzophenone

In Reference Example 24, the pink colored precipitate was washed with methanol, and dried to give the title compound (104.23 g).

NMR (CDCl$_3$) δ: 8.14 (d, J=8.79Hz, 2H), 7.82 (d, J=9.01Hz, 2H), 7.78 (d, J=8.57Hz, 2H), 6.97 (d, J=8.79Hz, 2H), 3.96 (s, 3H), 3.90 (s, 3H)

(2) Preparation of methyl 4-(4-methoxyphenylmethyl)benzoate

To a mixture of sodium borohydride (2.27 g) and trifluoroacetic acid (50 ml), which was previously prepared under nitrogen atmosphere, was added a solution of 4-methoxycarbonyl-4'-methoxybenzophenone (2.70 g) and methylene chloride (30 ml) at room temperature. After reacting for 24 hours, the reaction mixture was poured into ice-water, and methylene chloride layer was separated. Water layer was further extracted with methylene chloride (50 ml×2).

Methylene chloride layer was washed with saturated aqueous sodium hydrogencarbonate and saturated aqueous sodium chloride solution, dried over Glauber's salt, and concentrated to give the title compound (2.55 g).

NMR (CDCl$_3$) δ: 7.94 (d, J=8.35Hz, 2H), 7.23 (d, J=8.57Hz, 2H), 7.09 (d, J=9.01Hz, 2H), 6.83 (d, J=8.79 Hz, 2H), 3.97 (s, 2H), 3.91 (s, 3H), 3.79 (s, 3H)

(3) Preparation of 4-(4-methoxyphenylmethyl)benzyl alcohol

In the same manner as in Reference Example 20, by using methyl 4-(4-methoxyphenylmethyl)benzoate (2.55 g), there was prepared the title compound (1.87 g).

NMR (CDCl$_3$) δ: 7.1–7.4 (m, 4H), 7.09 (d, J=8.35Hz, 2H), 6.81 (d, J=8.79Hz, 2H), 4.64 (s, 2H), 3.92 (s, 2H), 3.77 (s, 3H)

(4) Preparation of 4-(4-methoxyphenylmethyl)benzylchloride

In the same manner as in Reference Example 20, by using 4-(4-methoxyphenylmethyl)benzyl alcohol (1.87 g), there was prepared the title compound (2.02 g).

NMR (CDCl$_3$) δ: 7.30 (d, J=9.01Hz, 2H), 7.14 (d, J=8.57Hz, 2H), 7.09 (d, J=9.01Hz, 2H), 6.81 (d, J=8.79Hz, 2H), 4.55 (s, 2H), 3.91 (s, 2H), 3.77 (s, 3H)

(5) Preparation of 4-(4-methoxyphenylmethyl)phenylacetonitrile

In the same manner as in Reference Example 20, by using 4-(4-methoxyphenylmethyl)benzylchloride (2.02 g), there was prepared the title compound (1.86 g).

NMR (CDCl$_3$) δ: 7.1–7.3 (m, 4H), 7.07 (d, J=8.79Hz, 2H), 6.81 (d, J=8.79Hz, 2H), 3.91 (s, 2H), 3.77 (s, 3H), 3.68 (s, 2H)

Example 17

Preparation of 4-hydroxy-8-[4-(2-methoxyphenylmethyl)phenyl]pyrazolo[1,5-a]-1,3,5-triazine In the same manner as in steps (2) to (5) of Reference Example 25, by using 4-methoxycarbonyl-2'-methoxybenzophenone, there was prepared 4-(2-methoxyphenylmethyl)phenylacetonitrile, and then in the same manner as in Example 13, by using this product, there was prepared the title compound.

mp: 246°–256° C.

NMR (DMSO-d$_6$) δ: 8.49 (s, 1H), 8.06 (s, 1H), 7.88 (d, J=8.13Hz, 2H), 6.8–7.3 (m, 6H), 3.90 (s, 2H), 3.78 (s, 3H)

Example 18

Preparation of 4-hydroxy-8-[4-(4-methoxyphenylmethyl)phenyl]pyrazolo[1,5-a]-1,3,5-triazine In the same manner as in Example 13, by using 4-(4-methoxyphenylmethyl)acetonitrile, there was prepared the title compound.

mp: 295.5°–297.5° C.

NMR (DMSO-d$_6$) δ: 8.52 (s, 1H), 8.01 (s, 1H), 7.91 (d, J=7.92Hz, 2H), 7.26 (d, J=8.25Hz, 2H), 7.15 (d, J=8.57Hz, 2H), 6.85 (d, J=8.57Hz, 2H), 3.88 (s, 2H), 3.71 (s, 3H)

Reference Example 26

(1) Preparation of methyl 4-ethylbenzoate

A mixture of 4-ethylbenzoic acid (5.12 g), thionyl chloride (3.0 ml) and methanol (150 ml) was heated and refluxed. After 3 hours, the mixture was concentrated under reduced pressure to give methyl 4-ethylbenzoate (5.59 g). This product was used in the subsequent step without purification.

(2) Preparation of methyl 4-(α-bromoethyl)benzoate

To a solution of methyl 4-ethylbenzoate (5.12 g) in carbon tetrachloride (50 ml) were added perbenzoic anhydride (0.20 g) and N-bromosuccinimide (6.07 g) in turn, and the mixture was heated and refluxed. After 30 minutes, the mixture was allowed to cool, and the precipitate was separated by filtration, and washed with carbon tetrachloride. The filtrate and the washings were combined, and concentrated under reduced pressure to give the title compound (8.28 g)

NMR (CDCl$_3$) δ: 8.02 (d, J=8.35Hz, 2H), 7.49 (d, J=8.35Hz, 2H), 5.19 (q, J=7.03Hz, 1H), 3.91 (s, 3H), 2.04 (d, J=7.03Hz, 3H)

(3) Preparation of methyl 4-(α-methylbenzyl)benzoate

In the same manner as in Reference Example 25, by using methyl 4-(α-bromoethyl)benzoate and benzene, there was prepared the title compound.

NMR (CDCl$_3$) δ: 7.94 (d, J=8.35Hz, 2H), 7.1–7.4 (m, 7H), 4.19 (q, J=7.95Hz, 1H), 3.88 (s, 3H), 1.65 (d, J=7.25Hz, 3H)

(4) Preparation of 4-hydroxymethyl-α-methyldiphenylmethane

In the same manner as in Reference Example 25, there was prepared the title compound.

NMR (CDCl$_3$) δ: 7.1–7.4 (m, 9H), 4.63 (s, 2H), 4.14 (q, J=7.25Hz, 1H), 1.63 (d, J=7.25Hz, 3H)

(5) Preparation of 4-chloromethyl-α-methyldiphenylmethane

In the same manner as in Reference Example 25, there was prepared the title compound.

NMR (CDCl$_3$) δ: 7.1–7.4 (m, 9H), 4.54 (s, 2H), 4.14 (q, J=7.25Hz, 1H), 1.62 (d, J=7.25Hz, 3H)

(6) Preparation of 4-(α-methylbenzyl)phenylacetonitrile

In the same manner as in Reference Example 25, there was prepared the title compound.

NMR (CDCl$_3$) δ: 7.1–7.4 (m, 9H), 4.14 (q, J=7.25Hz, 1H), 3.68 (s, 2H), 1.63 (d, J=7.25Hz, 3H)

Example 19

Preparation of 4-hydroxy-8-[4-(α-methylbenzyl)-phenyl]pyrazolo[1,5-a]-1,3,5-triazine In the same manner as in Example 13, by using 4-(α-methylbenzyl)phenylacetonitrile, there was prepared the title compound.

mp: 291°–293° C.

NMR (DMSO-d$_6$) δ: 8.52 (s, 1H), 8.09 (s, 1H), 7.91 (d, J=8.25Hz, 2H), 7.13–7.33 (m, 7H), 4.17 (q, J=7.25Hz, 1H), 1.60 (d, J=7.25Hz, 3H)

Reference Example 27

(1) Preparation of methyl 4-(n-butyl)benzoate

In the same manner as in Reference Example 26, there was prepared the title compound.

NMR (CDCl$_3$) δ: 7.93 (d, J=8.35Hz, 2H), 7.22 (d, J=8.35Hz, 2H), 3.89 (s, 3H), 2.5–2.8 (m, 2H), 1.1–1.8 (m, 4H), 0.8–1.1 (m, 3H)

(2) Preparation of methyl 4-(α-bromo-n-butyl)benzoate

In the same manner as in Reference Example 25, there was prepared the title compound.

NMR (CDCl$_3$) δ: 8.00 (d, J=8.13Hz, 2H), 7.44 (d, J=8.35Hz, 2H), 4.95 (t, J=7.47Hz, 1H), 3.91 (s, 3H), 1.9–2.4 (m, 2H), 1.1–1.7 (m, 2H), 0.8–1.1 (m, 3H)

(3) Preparation of methyl 4-(α-propyl-benzyl)benzoate

In the same manner as in Reference Example 25, there was prepared the title compound.

NMR (CDCl$_3$) δ: 7.93 (d, J=8.35Hz, 2H), 7.1–7.4 (m, 7H), 3.95 (q, J=7.69Hz, 1H), 3.87 (s, 3H), 1.8–2.2 (m, 2H), 1.0–1.5 (m, 2H), 0.7–1.0 (m, 3H)

(4) Preparation of 4-hydroxymethyl-α-propyldiphenylmethane

In the same manner as in Reference Example 25, there was prepared the title compound.

NMR (CDCl$_3$) δ: 7.1–7.4 (m, 9H), 4.61 (s, 2H), 3.90 (t, J=7.69Hz, 1H), 1.8–2.2 (m, 2H), 1.66 (bs, 1H), 1.0–1.4 (m, 2H), 0.8–1.0 (m, 3H)

(5) Preparation of 4-chloromethyl-α-propyldiphenylmethane

In the same manner as in Reference Example 25, there was prepared the title compound.

NMR (CDCl$_3$) δ: 7.0–7.5 (m, 9H), 4.53 (s, 2H), 3.90 (t, J=7.69Hz, 1H), 1.8–2.2 (m, 2H), 1.0–1.4 (m, 2H), 0.7–1.0 (m, 3H)

(6) Preparation of 4-(α-propyl-benzyl)phenylacetonitrile

In the same manner as in Reference Example 25, there was prepared the title compound.

NMR (CDCl$_3$) δ: 7.1–7.4 (m, 9H), 3.91 (t, J=7.69Hz, 1H), 3.67 (s, 2H), 1.8–2.2 (m, 2H), 1.0–1.4 (m, 2H), 0.8–1.0 (m, 3H)

Example 20

Preparation of 4-hydroxy-8-[4-(α-propylbenzyl)-phenyl]pyrazolo[1,5-a]-1,3,5-triazine In the same manner as in Example 13, by using 4-(α-propylbenzyl)phenylacetonitrile, there was prepared the title compound.

mp: 280°–285° C.

NMR (DMSO-d$_6$) δ: 8.48 (s, 1H), 8.06 (s, 1H), 7.89 (d, J=8.14Hz, 2H), 7.1–7.5 (m, 7H), 3.8–4.0 (m, 1H), 1.8–2.2 (m, 2H), 1.0–1.4 (m, 2H), 0.7–1.0 (m, 3H)

Reference Example 28

(1) Preparation of 3'-chloro-4-methoxycarbonylbenzhydrol

In the same manner as in step (1) of Reference Example 20, there was prepared the title compound.

NMR (CDCl$_3$) δ: 8.02 (d, J=8.59Hz, 2H), 7.44 (d, J=8.24Hz, 2H), 7.23–7.28 (m, 4H), 5.85 (s, 1H), 3.91 (s, 3H)

(2) Preparation of 3'-chloro-4-methoxycarbonyldiphenylmethane

To a solution of 3'-chloro-4-methoxycarbonylbenzhydrol (6.0 g) in methylene chloride (50 ml) was added dropwise a solution of trifluoroacetic acid (20 ml) in methylene chloride (5 ml) under ice-cooling, and thereto was added tablets of sodium borohydride (9 tablets, 2.7 g), and the mixture was stirred at 0° C. for 5 minutes and then at room temperature for 17 hours. Next, under ice-cooling, cooled water (100 ml) was added, and the reaction product was extracted with ethyl acetate. The extract was washed with 10% hydrochloric acid aqueous solution, saturated aqueous sodium hydrogencarbonate solution and saturated aqueous sodium chloride solution, dried over anhydrous magnesium sulfate, and the solvent was distilled away. The residue was separated and purified by using a silica-gel column chromatography (ethyl ether:n-hexane=1:30) to give the title compound (2.3 g).

NMR (CDCl$_3$) δ: 7.96 (d, J=8.24Hz, 2H), 7.14–7.24 (m, 5H), 7.02–7.05 (m, 1H), 3.97 (s, 2H), 3.88 (s, 3H)

(3) Preparation of 3'-chloro-4-hydroxymethyldiphenylmethane

In the same manner as in step (3) of Reference Example 20, there was prepared the title compound.

NMR (CDCl$_3$) δ: 7.24–7.32 (m, 2H), 7.10–7.21 (m, 5H), 7.05–7.08 (m, 1H), 4.67 (s, 2H), 3.95 (s, 2H)

(4) Preparation of 3'-chloro-4-chloromethyldiphenylmethane

In the same manner as in step (4) of Reference Example 20, there was prepared the title compound.

NMR (CDCl$_3$) δ: 7.29–7.34 (m, 2H), 7.15–7.23 (m, 5H), 7.04–7.07 (m, 1H), 4.57 (s, 2H), 3.95 (s, 2H)

(5) Preparation of 4-(3-chlorophenylmethyl)-phenylacetonitrile

In the same manner as in step (5) of Reference Example 20, there was prepared the title compound.

NMR (CDCl$_3$) δ: 7.15–7.28 (m, 7H), 7.03–7.06 (m, 1H), 3.95 (s, 2H), 3.72 (s, 2H)

Example 21

Preparation of 8-[4-(3-chlorophenylmethyl)phenyl]-4-hydroxypyrazolo[1,5-a]-1,3,5-triazine In the same manner as in Example 13, there was prepared the title compound.

mp: >300° C. (decomposed)

NMR (DMSO-d$_6$) δ: 8.51 (s, 1H), 8.09 (s, 1H), 7.94 (d, J=7.91Hz, 2H), 7.20–7.34 (m, 6H), 3.97 (s, 2H)

Reference Example 29

(1) Preparation of 4'-chloro-4-methoxycarbonylbenzhydrol

In the same manner as in step (1) of Reference Example 20, there was prepared the title compound.

NMR (CDCl$_3$) δ: 8.00 (d, J=8.59Hz, 2H), 7.43 (d, J=8.24Hz, 2H), 7.24–7.36 (m, 4H), 5.86 (s, 1H), 3.90 (s, 3H)

(2) Preparation of 4'-chloro-4-methoxycarbonyldiphenylmethane

In the same manner as in step (2) of Reference Example 28, there was prepared the title compound.

NMR (CDCl₃) δ: 7.96 (d, J=8.26Hz, 2H), 7.21–7.28 (m, 4H), 7.12 (d, J=8.56Hz, 2H), 3.99 (s, 2H), 3.96 (s, 3H)

(3) Preparation of 4'-chloro-4-hydroxymethyldiphenylmethane

In the same manner as in step (3) of Reference Example 20, there was prepared the title compound.

NMR (CDCl₃) δ: 7.22–7.31 (m, 4H), 7.08–7.17 (m, 4H), 4.66 (s, 2H), 3.94 (s, 2H)

(4) Preparation of 4'-chloro-4-chloromethyldiphenylmethane

In the same manner as in step (4) of Reference Example 20, there was prepared the title compound.

NMR (CDCl₃) δ: 7.23–7.34 (m, 4H), 7.07–7.16 (m, 4H), 4.56 (s, 2H), 3.94 (s, 2H)

(5) Preparation of 4-(4-chlorophenylmethyl)phenylacetonitrile

In the same manner as in step (5) of Reference Example 20, there was prepared the title compound.

NMR (CDCl₃) δ: 7.24–7.27 (m, 4H), 7.15–7.21 (m, 2H), 7.06–7.11 (m, 2H), 3.94 (s, 2H), 3.71 (s, 2H)

Example 22

Preparation of 8-[4-(4-chlorophenylmethyl)phenyl]-4-hydroxypyrazolo[1,5-a]-1,3,5-triazine In the same manner as in Example 13, there was prepared the title compound.

mp: 292°–296° C.

NMR (DMSO-d₆) δ: 8.51 (s, 1H), 8.08 (s, 1H), 7.93 (d, J=8.24Hz, 2H), 7.24–7.34 (m, 6H), 3.95 (s, 2H)

Reference Example 30

(1) Preparation of 3'-methoxy-4-methoxycarbonyl-α-methylbenzhydrol

A mixture of m-bromoanisole (4.0 g), magnesium metal (546 mg) and tetrahydrofuran (30 ml) was heated under nitrogen atmosphere by using a dryer. Heat was stopped at the time that the reaction was initiated, and the mixture was stirred till generation of heat was terminated. The reaction mixture was cooled to 0° C., and thereto was added methyl p-acetylbenzoate (4.0 g) under stirring, and the mixture was stirred at 0° C. for 10 minutes. Next, saturated ammonium chloride (50 ml) and water (100 ml) were added, and the mixture was extracted with ethyl acetate. The extract was 10% aqueous hydrochloric acid solution, water, saturated aqueous sodium hydrogencarbonate solution and saturated aqueous sodium chloride solution, dried over anhydrous magnesium sulfate, and concentrated under reduced pressure. The residue was separated and purified by using a silica-gel column chromatography (ethyl acetate:n-hexane=1:5) to give the title compound (2.9 g).

NMR (CDCl₃) δ: 7.97 (d, J=8.59Hz, 2H), 7.49 (d, J=8.59Hz, 2H), 7.20–7.27 (m, 1H), 6.93–6.99 (m, 2H), 6.77–6.81 (m, 1H), 3.90 (s, 3H), 3.77 (s, 3H), 1.95 (s, 3H)

(2) Preparation of 3'-methoxy-4-methoxycarbonyl-α-methyldiphenylmethane

In the same manner as in step (2) of Reference Example 20, there was prepared the title compound.

NMR (CDCl₃) δ: 7.96 (d, J=8.24Hz, 2H), 7.16–7.30 (m, 3H), 6.72–6.81 (m, 3H), 4.18 (q, J=7.26Hz, 1H), 3.89 (s, 3H), 3.77 (s, 3H), 1.64 (d, J=7.26Hz, 3H)

(3) Preparation of 4-hydroxymethyl-3'-methoxy-α-methyldiphenylmethane

In the same manner as in step (3) of Reference Example 20, there was prepared the title compound.

NMR (CDCl₃) δ: 7.17–7.30 (m, 5H), 6.70–6.82 (m, 3H), 4.65 (s, 2H), 4.12 (q, J=7.26Hz, 1H), 3.77 (s, 3H), 1.62 (d, J=7.26Hz, 3H)

(4) Preparation of 4-chloromethyl-3'-methoxy-α-methyldiphenylmethane

In the same manner as in step (4) of Reference Example 20, there was prepared the title compound.

NMR (CDCl₃) δ: 7.17–7.31 (m, 5H), 6.71–6.82 (m, 3H), 4.55 (s, 2H), 4.12 (q, J=7.26Hz, 1H), 3.77 (s, 3H), 1.62 (d, J=7.26Hz, 3H)

(5) Preparation of 4-[1-(3-methoxyphenyl)ethan-1-yl]phenylacetonitrile

In the same manner as in step (5) of Reference Example 20, there was prepared the title compound.

NMR (CDCl₃) δ: 7.18–7.26 (m, 5H), 6.71–6.81 (m, 3H), 4.12 (q, J=7.26Hz, 1H), 3.77 (s, 3H), 3.70 (s, 2H), 1.62 (d, J=7.26Hz, 3H)

Example 23

Preparation of 4-hydroxy-8-{4-[1-(3-methoxyphenyl)ethan-1-yl]phenyl}pyrazolo[1,5-a]-1,3,5-triazine In the same manner as in Example 13, there was prepared the title compound.

mp: 282°–285° C.

NMR (DMSO-d₆) δ: 8.49 (s, 1H), 8.07 (s, 1H), 7.91 (d, J=8.24Hz, 2H), 7.31 (d, J=8.24Hz, 2H), 7.16–7.22 (m, 1H), 6.81–6.85 (m, 2H), 6.71–6.75 (m, 1H), 4.13 (q, J=7.26Hz, 1H), 3.72 (s, 3H), 1.59 (d, J=7.26Hz, 3H)

Reference Example 31

(1) Preparation of 6-ethoxycarbonyl-7-hydroxy-3-[3-methoxy-4-(3-methoxyphenylmethyl)phenyl]pyrazolo[1,5-a]pyrimidine In the same manner as in Reference Example 8, by using 3-amino-4-[3-methoxy-4-(3-methoxyphenylmethyl)phenyl]pyrazole (1.5 g), there was prepared the title compound (1.85 g).

mp: 226°–238° C. (foamed)

NMR (DMSO-d₆) δ: 8.35 (s, 1H), 8.25 (s, 1H), 7.0–7.6 (m, 4H), 6.7–6.8 (m, 3H), 4.25 (q, J=6.92Hz, 2H), 3.90 (s, 2H), 3.88 (s, 3H), 3.71 (s, 3H), 1.29 (t, J=6.92Hz, 3H)

NMR of 3-amino-4-[3-methoxy-4-(3-methoxyphenylmethyl)phenyl]pyrazole used as a starting material is shown below.

NMR (CDCl₃) δ: 7.47 (bs, 1H), 7.1–7.3 (m, 1H), 7.09 (d, J=8.24Hz, 1H), 6.9–7.0 (m, 2H), 6.7–6.9 (m, 3H), 4.28 (b, 3H), 3.95 (s, 2H), 3.85 (s, 3H), 3.78 (s, 3H)

(2) Preparation of 6-carboxy-7-hydroxy-3-[3-methoxy-4-(3-methoxyphenylmethyl)phenyl]pyrazolo[1,5-a]pyrimidine In the same manner as in Reference Example 9, by using 6-ethoxycarbonyl-7-hydroxy-3-[3-methoxy-4-(3-methoxyphenylmethyl) phenyl]pyrazolo[1,5-a]pyrimidine (1.80 g), reaction was carried out, and the obtained precipitate was washed in turn with water and ether, and dried to give the title compound (1.68 g).

mp: 175°–182° C. (foamed)

NMR (DMSO-₆) δ: 8.44 (s, 1H), 8.35 (s, 1H), 7.1–7.3 (m, 4H), 6.7–6.9 (m, 3H), 3.90 (s, 2H), 3.88 (s, 3H), 3.71 (s, 3H)

Example 24

Preparation of 7-hydroxy-3-[3-methoxy-4-(3-methoxyphenylmethyl)phenyl]pyrazolo[1,5-a]pyrimidine In the same manner as in Example 2, by using 6-carboxy-7-hydroxy-3-[3-methoxy-4-(3-methoxyphenylmethyl)phenyl]pyrazolo[1,5-a]pyrimidine (1.62 g), there was prepared the title compound (1.31 g).

mp: 238°–240° C. (decomposed)

NMR (DMSO-d$_6$) δ: 8.18 (s, 1H), 7.77 (d, J=6.81Hz, 1H), 7.0–7.4 (m, 4H), 6.6–7.0 (m, 3H), 5.76 (d, J=7.25Hz, 1H), 3.88 (s, 3H), 3.71 (s, 3H)

Reference Example 32

(1) Preparation of 3-amino-4-(α-methylbenzyl)phenylpyrazole

In the same manner as in Reference Example 7, by using 3-amino-2-carbamoyl-4-(α-methylbenzyl)phenylpyrazole (3.66 g), the reaction was carried out, and the reaction product was separated and purified by using a silica-gel column chromatography (chloroform:methanol=30:1) to give the title compound (2.0 g).

NMR (CDCl$_3$) δ: 7.46 (s, 1H), 7.1–7.4 (m, 5H), 7.38 (d, J=8.24Hz, 2H), 7.25 (d, J=8.25Hz, 2H), 3.5–5.5 (b, 3H), 4.16 (q, J=7.26Hz, 1H), 1.66 (d, J=7.26Hz, 3H)

(2) Preparation of 6-carboxy-7-hydroxy-3-[4-(α-methylbenzyl)phenyl]pyrazolo[1,5-a]pyrimidine In the same manner as in Reference Example 8 and the steps (1) and (2) of Reference Example 31, by using 3-amino-4-(α-methylbenzyl) phenylpyrazole (1.95 g), there was prepared the title compound (2.56 g).

NMR (DMSO-d$_6$) δ: 8.42 (s, 1H), 8.30 (s, 1H), 7.54 (d, J=8.24Hz, 2H), 7.38 (d, J=8.24Hz, 2H), 7.1–7.4 (m, 5H), 4.22 (q, J=7.26Hz, 1H), 1.62 (d, J=7.26 Hz, 3H)

Example 25

Preparation of 7-hydroxy-3-[4-(α-methylbenzyl)phenyl]pyrazolo[1,5-a]pyrimidine

In the same manner as in Example 2, by using 6-carboxy-7-hydroxy-3-[4-(α-methylbenzyl)phenyl]-pyrazolo[1,5-a]pyrimidine (1.95 g), there was prepared the title compound (1.30 g).

mp: 290°–293° C. (decomposed)

NMR (DMSO-d$_6$) δ: 8.12 (s, 1H), 7.75 (d, J=7.47Hz, 1H), 7.1–7.6 (m, 9H), 5.75 (d, J=7.47Hz, 1H), 4.20 (q, J=7.47Hz, 1H), 1.62 (d, J=7.26Hz, 3H)

Reference Example 33

Preparation of 2-bromo-5-t-butyldimethylsilyloxymethyltoluene

To a solution of 2-bromo-5-hydroxymethyltoluene (87.4 g) in methylene chloride (350 ml) were added, under ice-cooling with stirring, trietylamine (72.7 ml) and 4-dimethylaminopyridine (DMAP)(500 mg), and then thereto was added t-butyldimethylsilyl chloride (65.5 g). The mixture was stirred at 0° C. for 15 minutes, and stirred at room temperature for 3 hours. The reaction mixture is filtrated, and the filtrate was concentrated under reduced pressure. To the residue was added water (100 ml), and the mixture was extracted with ethyl acetate.

The extract was washed with 10% aqueous hydrochloric acid solution, water, saturated aqueous sodium hydrogencarbonate solution and saturated aqueous sodium chloride solution, dried over anhydrous magnesium sulfate, and the solvent was distilled away. The residue was purified by a reduced pressure distillation (110° C. to 115° C./0.4 mmHg) to give the title compound (127.5 g).

NMR (CDCl$_3$) δ: 7.47 (d, J=8.10Hz, 1H), 7.17 (s, 1H), 6.70–7.02 (m, 1H), 4.65 (s, 2H), 2.39 (s, 3H), 0.94 (s, 9H), 0.09 (s, 6H)

Reference Example 34

Preparation of 4-t-butyldimethylsillyloxymethyl-3'-methoxy-2-methylbenzhydrol

To a suspension of magnesium metal (2.4 g) in tetrahydrofuran (10 ml) were added 10 ml of a solution of 2-bromo-5-t-butyldimethylsilyloxymethyltoluene (30 g) in tetrahydrofuran (100 ml) and dibromoethane (0.1 ml) under nitrogen atmosphere, and the mixture was stirred. After the reaction was initiated, to the mixture was added dropwise residual tetrahydrofuran solution (100 ml) so as to quietly continue the generation of heat. After dropping, the mixture was stirred till the generation of heat was terminated, and further stirred for 30 minutes. Then, to the mixture were added 3-methoxybenzaldehyde (11.58 ml) and the mixture was stirred for 1 hour under ice-cooling. Next, to the mixture were added saturated ammonium chloride (100 ml) and water (50 ml) under stirring under ice-cooling, and the mixture was stirred under ice-cooling for 30 minutes, and extracted with ethyl acetate. The extract was washed with 10% hydrochloric acid solution, water, saturated aqueous sodium hydrogen carbonate solution and saturated aqueous sodium chloride solution, dried over anhydrous magnesium sulfate, and concentrated under reduced pressure. The residue was separated and purified by using a silica-gel column chromatography (ethyl acetate:n-hexane=1:12 followed by 1:8) to give the title compound (22.0 g).

NMR (CDCl$_3$) δ: 7.33 (d, J=7.91Hz, 1H), 7.07–7.16 (m, 2H), 7.00 (s, 1H), 6.77–6.89 (m, 2H), 6.66–6.71 (m, 1H), 5.97 (s, 1H), 4.70 (s, 2H), 3.78 (s, 3H), 2.27 (s, 3H), 0.93 (s, 9H), 0.09 (s, 6H)

Reference Example 35

Preparation of α-acetoxy-4-t-butyldimethylsilyloxymethyl-3'-methoxy-2-methyldiphenylmethane To a solution of 4-t-butyldimethylsilyloxymethyl-3'-methoxy-2-methylbenzhydrol (22 g) in pyridine (50 ml) were added 4-dimethylaminopyridine (500 mg) under ice-cooling with stirring, and thereto was added dropwise acetylchloride (4.2 ml). After dropping, the mixture was stirred under ice-cooling for 10 minutes, and further stirred at room temperature for 3.5 hours. Under ice-cooling, to the mixture was added water (100 ml), and the mixture was extracted with ethyl acetate. The extract was washed with 10% hydrochloric acid solution, water, saturated aqueous sodium hydrogencarbonate solution and saturated aqueous sodium chloride solution, dried over anhydrous magnesium sulfate, and the solvent was distilled away under reduced pressure. The residue was separated and purified by using a silica-gel column chromatography (ethyl acetate:n-hexane=1:8) to give the title compound (22.8 g).

NMR (CDCl$_3$) δ: 7.33 (d, J=7.83Hz, 1H), 7.15–7.23 (m, 3H), 7.00 (s, 1H), 6.80–6.87 (m, 3H), 4.70 (s, 2H), 3.77 (s, 3H), 2.30 (s, 3H), 2.14 (s, 3H), 0.94 (s, 9H), 0.10 (s, 6H)

Reference Example 36

Preparation of 4-t-butyldimethylsilyloxymethyl-3'-methoxy-2-methyldiphenylmethane To a solution of α-acetoxy-4-t-butyldimethylsilyloxymethyl -3'-methoxy-2-methyldiphenylmethane (36.5 g) in ethanol (130 ml) were added triethylamine (20 ml), and thereto was added 5%-palladium-barium sulfate (3.0 g). Under hydrogen atmosphere, the mixture was stirred at ordinary temperature and ordinary pressure for 16 hours. The catalyst was separated by filtration, and after adding water (100 ml), the filtrate was extracted with ethyl acetate. The extract was washed with 10% hydrochloric acid solution, water, saturated aqueous sodium hydrogencarbonate solution and saturated aqueous sodium chloride solution, dried over anhydrous magnesium sulfate, and the solvent was distilled away under reduced pressure to give the title compound (31 g).

NMR (CDCl$_3$) δ: 7.04–7.21 (m, 4H), 6.66–6.72 (m, 3H), 4.69 (s, 2H), 3.90 (s, 2H), 3.75 (s, 3H), 2.23 (s, 3H), 0.94 (s, 9H), 0.10 (s, 6H)

Reference Example 37

Preparation of 4-hydroxymethyl-3'-methoxy-2-methylbenzhydrol

To a solution of 4-t-butyldimethylsilylmethyl-3'-methoxy-2-methyldiphenylmethane (26.5 g) in methanol (100 ml) was added dropwise 10% hydrochloric acid solution (30 ml) at room temperature with stirring.

After dropping, the mixture was stirred at room temperature for 30 minutes. Methanol was distilled away under reduced pressure, and to the residue was added water (50 ml), and the mixture was extracted with ethyl acetate. The extract was washed 10% hydrochloric acid solution, water, saturated aqueous sodium hydrogencarbonate solution and saturated aqueous sodium chloride solution, dried over anhydrous magnesium sulfate, and the solvent was distilled away under reduced pressure. The residue was separated and purified by using a silica-gel column chromatography (ethyl acetate:n-hexane=1:3) to give the title compound (16.5 g).

NMR (CDCl$_3$) δ: 7.08–7.21 (m, 4H), 6.66–6.74 (m, 3H), 4.64 (s, 2H), 3.95 (s, 2H), 3.76 (s, 3H), 2.25 (s, 3H)

Reference Example 38

(1) Preparation of 4-chloromethyl-3'-methoxy-2-methyldiphenylmethane

In the same manner as in Reference Example 3, by using 4-hydroxymethyl-3'-methoxy-2-methyldiphenylmethane (2.70 g), there was prepared the title compound (2.90 g).

NMR (CDCl$_3$) δ: 7.0–7.3 (m, 4H), 6.6–6.8 (m, 3H), 4.55 (s, 2H), 3.94 (s, 2H), 3.76 (s, 3H), 2.25 (s, 3H)

(2) Preparation of 4-(3-methoxyphenylmethyl)-3-methylphenylacetonitrile

In the same manner as in Reference Example 4, by using 4-chloromethyl-3'-methoxy-2-methyldiphenylmethane (2.90 g), there was prepared the title compound (2.35 g).

NMR (CDCl$_3$) δ: 7.0–7.4 (m, 4H), 6.6–6.9 (m, 3H), 3.93 (s, 2H), 3.75 (s, 3H), 3.67 (s, 2H), 2.24 (s, 3H)

(3) Preparation of 3-amino-2-carbamoyl-4-[4-(3-methoxyphenylmethyl)-3-methyl]phenylpyrazole In the same manner as in Reference Examples 5 and 6, by using 4-(3-methoxyphenylmethyl)-3-methylphenylacetonitrile (2.35 g), there was prepared the title compound (1.88 g).

NMR (DMSO-d$_6$) δ: 7.65 (s, 1H), 7.56 (bs, 1H), 7.0–7.3 (m, 3H), 6.5–6.9 (m, 4H), 3.91 (s, 2H), 3.70 (s, 3H), 2.23 (s, 3H)

Reference Example 39

(1) Preparation of 3-amino-4-[4-(3-methoxyphenylmethyl)-3-methyl]phenylpyrazole

In the same manner as in Reference Example 7, by using 3-amino-2-carbamoyl-4-[4-(3-methoxyphenylmethyl)-3-methyl]phenylpyrazole (1.88 g), the reaction was carried out, and the reaction product was separated and purified by using a silica-gel column chromatography (chloroform:methanol=30:1) to give the title compound (1.32 g).

NMR (CDCl$_3$) δ: 7.47 (s, 1H), 7.1–7.3 (m, 4H), 6.6–6.8 (m, 3H), 3.96 (s, 2H), 3.77 (s, 3H), 3.5–4.3 (b, 3H), 2.27 (s, 3H)

(2) Preparation of 6-carboxy-7-hydroxy-3-[4-(3-methoxyphenylmethyl)-3-methyl]phenylpyrazolo[1,5-a]pyrimidine In the same manner as in Reference Example 8, by using 3-amino-4-[4-(3-methoxyphenylmethyl)-3-methyl]phenylpyrazole (1.30 g), there was prepared the title compound (1.31 g).

mp: 182°–188° C. (foamed)

NMR (DMSO-d$_6$) δ: 8.44 (s, 1H), 8.33 (s, 1H), 7.4–7.5 (m, 2H), 7.1–7.3 (m, 2H), 6.7–6.8 (m, 3H), 3.97 (s, 2H), 3.71 (s, 3H), 2.28 (s, 3H)

Example 26

Preparation of 7-hydroxy-3-[4-(3-methoxyphenylmethyl)-3-methyl]phenylpyrazolo[1,5-a]pyrimidine In the same manner as in Example 2, by using 6-carboxy-7-hydroxy-3-[4-(3-methoxyphenylmethyl)-3-methyl]phenylpyrazolo[1,5-a]pyrimidine (1.26 g), there was prepared the title compound (1.05 g).

mp: 271°–275° C.

NMR (DMSO-d$_6$) δ: 8.17 (s, 1H), 7.80 (d, J=7.26Hz, 1H), 7.3–7.4 (m, 2H), 7.1–7.3 (m, 2H), 6.7–6.8 (m, 3H), 5.76 (d, J=7.26Hz, 1H), 3.96 (s, 2H), 3.71 (s, 3H), 2.27 (s, 3H)

Reference Example 40

Preparation of 3-amino-4-[4-(3-methylphenylmethyl)-phenyl]pyrazole

To a solution of 3-amino-2-carbamoyl-4-[4-(3-methylphenylmethyl) phenyl]pyrazole (2.0 g) in methanol (20 ml) was added 5N sodium hydroxide solution (10 ml), and the mixture was refluxed for 4 hours. Methanol was distilled away under reduced pressure. To the residue was added water (100 ml), and the mixture was neutralized (pH 7 to 8) with conc. hydrochloric acid, and extracted with chloroform. The extract was washed with water and saturated aqueous sodium chloride solution, dried over anhydrous magnesium sulfate, and the solvent was distilled away under reduced pressure. The residue was separated and purified by using a silica-gel column chromatography (ethyl acetate:n-hexane=1:1 followed by chloroform:methanol=10:1) to give a mixture containing the title compound. This mixture Was used in the subsequent reaction without isolation.

Reference Example 41

Preparation of 6-carboxy-7-hydroxy-3-[4-(3-methylphenylmethyl)phenyl]pyrazolo[1,5-a]pyrimidine In the same manner as in Reference Example 8, by using 3-amino-4-[4-(3-methylphenylmethyl)phenyl]-pyrazole (1.31 g), there was prepared 6-ethoxycarbonyl-7-hydroxy-3-[4-(3-methylphenylmethyl)phenyl]-pyrazolo[1,5-a]pyrimidine.

NMR (DMSO-d$_6$) δ: 8.34 (s, 1H), 8.21 (s, 1H), 7.49 (d, J=8.25Hz, 2H), 7.34 (d, J=8.25Hz, 2H), 7.1–7.2 (m, 1H), 6.9–7.1 (m, 3H), 4.25 (q, J=7.26Hz, 2H), 3.94 (s, 2H), 2.27 (s, 3H), 1.29 (t, J=7.25Hz, 3H)

In the same manner as in Reference Example 31, by using the product thus obtained, there was prepared the title compound (1.64 g).

NMR (DMSO-d$_6$) δ: 8.43 (s, 1H), 8.32 (s, 1H), 7.58 (d, J=8.25Hz, 2H), 7.33 (d, J=8.25Hz, 2H), 7.1–7.2 (m, 1H), 6.9–7.1 (m, 3H), 3.94 (s, 2H), 2.27 (s, 3H)

Example 27

Preparation of 7-hydroxy-3-[4-(3-methylphenylmethyl)phenyl]-pyrazolo[1,5-a]pyrimidine A mixture of 6-carboxy-7-hydroxy-3-[4-(3-methylphenylmethyl)phenyl]pyrazolo[1,5-a]pyrimidine (1.44 g) and aniline (10 ml) was heated at 100° C. to 110° C. with stirring, and reacted with each other for 1 hour. After completion of reaction, ice-water (100 ml) was poured into the mixture, and the precipitate was filtrated, washed with water and 30% methol, dried, and separated and purified by using a silica-gel column chromatography (chloroform:methanol=30:1) to give the title compound (0.50 g).

mp: 273°–276° C. (decomposed)

NMR (DMSO-d$_6$) δ: 8.13 (s, 1H), 7.77 (d, J=7.26Hz, 1H), 7.49 (d, J=8.25Hz, 2H), 7.31 (d, J=8.25Hz, 2H), 6.9–7.2 (m, 4H), 5.76 (d, J=7.59Hz, 1H), 3.93 (s, 2H), 2.27 (s, 3H)

Reference Example 42

(1) Preparation of 3-amino-2-carbamoyl-4-[4-(3-methoxyphenylmethyl)phenyl]pyrazole In the same manner as in Reference Examples 5 and 6, by using 4-(3-methoxyphenylmethyl)phenylacetonitrile (10.01 g), there was prepared the title compound (11.36 g).

NMR (DMSO-d$_6$) δ: 7.68 (s, 1H), 7.62–7.66 (m, 2H), 7.39 (d, J=7.91Hz, 2H), 7.11–7.25 (m, 3H), 6.73–6.82 (m, 3H), 6.58 (bs, 2H), 3.89 (s, 2H), 3.71 (s, 3H)

(2) Preparation of 3-amino-4-[4-(3-methoxyphenylmethyl)phenyl]pyrazole

To a solution of 3-amino-2-carbamoyl-4-[4-(3-methoxyphenylmethyl)phenyl]pyrazole (4.1 g) in methanol (50 ml) was added 5N sodium hydroxide solution (20 ml), and the mixture was refluxed for 30 minutes. Methanol was distilled away under reduced pressure. To the residue was added water (150 ml), and the mixture was neutralized (pH 7 to 8) with conc. hydrochloric acid, and extracted with chloroform. The extract was washed with water and saturated aqueous sodium chloride solution, dried over anhydrous magnesium sulfate, and the solvent was distilled away under reduced pressure. The residue was separated and purified by using a silica-gel column chromatography (ethyl acetate:n-hexane=1:1, followed by ethyl acetate) to give the title compound (1.8 g).

mp: 118°–120° C.

NMR (CDCl$_3$) δ: 7.49 (s, 1H), 7.32–7.37 (m, 2H), 7.15–7.28 (m, 4H), 6.74–6.87 (m, 3H), 3.96 (s, 2H), 3.82 (s, 3H)

In the same manner as mentioned above, by using the residual starting material (11.36 g) of the step (2), there was prepared the title compound (5.14 g).

(3) Preparation of 6-ethoxycarbonyl-7-hydroxy-3-[4-(3-methoxyphenylmethyl)phenyl]pyrazolo[1,5-a]pyrimidine In the same manner as in Reference Example 8, by using 3-amino-4-[4-(3-methoxyphenylmethyl)phenyl]pyrazole (5.00 g), there was prepared the title compound (7.20 g).

mp: 236°–240° C. (foamed)

NMR (DMSO-d$_6$) δ: 8.34 (s, 1H), 8.22 (s, 1H), 7.51 (d, J=7.92Hz, 2H), 7.36 (d, J=8.25Hz, 2H), 7.1–7.3 (m, 1H), 6.7–6.9 (m, 3H), 4.25 (q, J=7.26Hz, 2H), 3.95 (s, 2H), 3.73 (s, 3H), 1.29 (t, J=7.26Hz, 3H)

(4) Preparation of 6-carboxy-7-hydroxy-3-[4-(3-methoxyphenylmethyl)phenyl]pyrazolo[1,5-a]pyrimidine In the same manner as in the step (2) of Reference Example 31, there was prepared the title compound (6.70 g).

mp: 190°–192° C. (foamed)

NMR (DMSO-d$_6$) δ: 8.43 (s, 1H), 8.32 (s, 1H), 7.57 (d, J=7.92Hz, 2H), 7.35 (d, J=8.25Hz, 2H), 7.1–7.3 (m, 1H), 6.7–6.9 (m, 3H), 3.95 (s, 2H), 3.73 (s, 3H)

Example 28

Preparation of 7-hydroxy-3-[4-(3-methoxyphenylmethyl)phenyl]pyrazolo[1,5-a]pyrimidine In the same manner as in Example 2, by using 6-carboxy-7-hydroxy-3-[4-(3-methoxyphenylmethyl)phenyl]pyrazolo[1,5-a]pyrimidine (6.70 g), there was prepared the title compound (5.67 g).

mp: 246°–249° C.

NMR (DMSO-d$_6$) δ: 8.17 (s, 1H), 7.79 (d, J=7.59Hz, 1H), 7.50 (d, J=8.25Hz, 2H), 7.33 (d, J=8.25Hz, 2H), 7.1–7.3 (m, 1H), 6.7–6.9 (m, 3H), 5.76 (d, J=7.26Hz, 1H), 3.94 (s, 2H), 3.72 (s, 3H)

Reference Example 43

Preparation of 4-t-butyldimethylsilyloxymethyl-2,3'-dimethylbenzhydrol

Magnesium (0.84 g, 34.6 millimol) was suspended in tetrahydrofuran (30 ml), and thereto was added a small amount of iodine. Under nitrogen atmosphere, a solution of 2-bromo-5-t-butyldimethylsilyloxymethyltoluene (10 g, 31.6 millimol) in tetrahydrofuran (10 ml) was added. When the mixture was heated for some time, the reaction was started, and heat generated. After stirring for 2 hours as it was, m-methylbenzaldehyde (3.16 g, 26.3 millimol) was added. After stirring for 2 hours, to the mixture was added saturated aqueous ammonium chloride solution, and the mixture was extracted with ethyl acetate. The organic layer was washed with water, dried over anhydrous sodium sulfate, and the solvent was distilled away under reduced pressure. The residue was separated and purified by using a silica-gel column chromatography (ethyl acetate:n-hexane=1:6) to give the title compound (6 g, 16.8 millimol, 64%).

NMR (CDCl$_3$) δ: 7.46 (d, J=7.9Hz, 1H), 7.05–7.23 (m, 6H), 5.96 (s, 1H), 4.71 (s, 2H), 2.32 (s, 3H), 2.25 (s, 3H), 0.94 (s, 9H), 0.10 (s, 6H)

Reference Example 44

Preparation of α-acetoxy-4-t-butyldimethylsilyloxymethyl-2,3'-dimethylbenzhydrol 4-t-Butyldimethylsilyloxymethyl-2,3'-dimethylbenzhydrol (6 g, 16.8 millimol) was dissolved in pyridine (10 ml), and thereto was added dimethylaminopyridine (200 mg, 1,6 millimol), and the mixture was cooled with ice. To the mixture were added acetylchloride (1.54 g, 19.6 millimol) and methylene chloride (10 ml). The mixture was returned to room temperature, and stirred for 2 hours. After adding water, the mixture was extracted with ethyl acetate, the organic layer was washed with in turn dil. hydrochloric acid, water and saturated aqueous sodium chloride solution, dried over anhydrous sodium sulfate. The solvent was distilled away to give the title compound (6.9 g, 16.6 millimol, 99%).

NMR (CDCl$_3$) δ: 7.35 (d, J=7.9Hz, 1H), 7.08–7.23 (m, 6H), 7.00 (s, 1H), 4.70 (s, 2H), 2.31 (s, 3H), 2.29 (s, 3H), 2.14 (s, 3H), 0.94 (s, 9H), 0.10 (s, 6H)

Reference Example 45

Preparation of 4-hydroxymethyl-2,3'-dimethyldiphenylmethane

α-acetoxy-4-t-butyldimethylsilyloxymethyl-2,3'-dimethylbenzhydrol (6.9 g, 16.6 millimol) was dissolved in 10% triethylamine-ethanol solution (20 ml), and thereto was added 5% palladium-barium sulfate (0.5 g). After stirring at room temperature for 19 hours under hydrogen atmosphere, the insoluble material was separated by filtration, and the solvent was distilled away. The residue was dissolved in ethyl acetate, washed with 10% hydrochloric acid, water and saturated aqueous sodium chloride solution, dried over anhydrous sodium sulfate. After the solvent was distilled away under reduced pressure, the residue was dissolved in methanol (100 ml), and thereto was added 10% hydrochloric acid (20 ml), and the mixture was stirred at room temperature for 30 minutes. After distilling water away, to the residue was added water, and the mixture was extracted with ethyl acetate. The organic layer was washed with saturated aqueous sodium hydrogencarbonate solution, water and saturated aqueous sodium chloride solution, and the solvent was distilled away under reduced pressure. The residue was separated and purified by using a silica-gel column chromatography (ethyl acetate:n-hexane=1:1) to give the title compound (3.4 g, 15 millimol, 90%).

NMR (CDCl$_3$) δ: 6.89–7.18 (m, 7H), 4.65 (s, 2H), 3.94 (s, 2H), 2.30 (s, 3H), 2.25 (s, 3H)

Reference Example 46

(1) Preparation of 4-chloromethyl-2,3'-dimethyldiphenylmethane

In the same manner as in Reference Example 3, by using 4-hydroxy-2,3'-dimethyldiphenylmethane (3.4 g), there was prepared the title compound (3.66 g).

NMR (CDCl$_3$) δ: 6.8–7.3 (m, 7H), 4.54 (s, 2H), 3.92 (s, 2H), 2.29 (s, 3H), 2.25 (s, 3H)

(2) Preparation of 3-methyl-4-(3-methylphenylmethyl)-phenylacetonitrile

In the same manner as in Reference Example 4, by using 4-chloromethyl-2,3'-dimethyldiphenylmethane (3.65 g), there was prepared the title compound (3.35 g).

NMR (CDCl$_3$) δ: 6.8–7.3 (m, 7H), 3.93 (s, 2H), 3.70 (s, 2H), 2.30 (s, 3H), 2.25 (s, 3H)

(3) Preparation of 3-amino-2-carbamoyl-4-[3-methyl-4-(3-methylphenylmethyl)phenylpyrazole In the same manner as in Reference Examples 5 and 6, by using 3-methyl-4-(3-methylphenylmethyl)-phenylacetonitrile (3.35 g), there was prepared the title compound (3.89 g).

NMR (DMSO-d$_6$) δ: 7.66 (s, 1H), 7.57 (bs, 2H), 6.8–7.3 (m, 7H), 6.53 (bs, 2H), 3.90 (s, 2H), 2.25 (s, 3H), 2.23 (s, 3H)

Example 29

Preparation of 4-hydroxy-8-[3-methyl-4-(3-methylphenylmethyl)phenyl]pyrazolo[1,5-a]-1,3,5-triazine In the same manner as in Example 1, by using 3-amino-2-carbamoyl-4-[3-methyl-4-(3-methylphenylmethyl)phenylpyrazole (0.49 g), there was prepared the title compound (0.23 g).

mp: 259°–262° C.

NMR (DMSO-d$_6$) δ: 8.54 (s, 1H), 8.11 (s, 1H), 7.82 (s, 1H), 7.79 (d, J=7.92Hz, 1H), 7.1–7.2 (m, 2H), 6.9–7.0 (m, 3H), 3.93 (s, 2H), 2.25 (s, 3H), 2.24 (s, 3H)

Reference Example 47

(1) Preparation of 3-amino-4-[3-methyl-4-(3-methylphenylmethyl)]phenylpyrazole

In the same manner as in Reference Example 7, by using 2-carbamoyl-3-amino-4-[3-methyl-4-(3-methylphenylmethyl)]phenylpyrazole (1.60 g), there was prepared the title compound (0.99 g).

NMR (CDCl$_3$) δ: 7.48 (s, 1H), 7.1–7.3 (m, 4H), 6.9–7.1 (m, 3H), 4.36 (b, 4H), 3.95 (s, 2H), 2.31 (s, 3H), 2.28 (s, 3H)

(2) Preparation of 6-ethoxycarbonyl-7-hydroxy-3-[3-methyl-4-(3-methylphenylmethyl)]phenylpyrazolo[1,5-a]pyrimidine In the same manner as in Reference Example 8, by using 3-amino-4-[3-methyl-4-(3-methylphenylmethyl)]-phenylpyrazole (0.99 g), there was prepared the title compound (1.43 g).

mp: 226°–234° C. (foamed)

NMR (DMSO-d$_6$) δ: 8.36 (s, 1H), 8.23 (s, 1H), 7.3–7.4 (m, 2H), 7.1–7.3 (m, 2H), 6.9–7.1 (m, 3H), 4.25 (q, J=6.93Hz, 2H), 3.96 (s, 2H), 2.28 (s, 3H), 2.26 (s, 3H), 1.29 (t, J=6.93Hz, 3H)

(3) Preparation of 6-carboxy-7-hydroxy-3-[3-methyl-4-(3-methylphenylmethyl)]phenylpyrazolo[1,5-a]pyrimidine In the same manner as in step (2) of Reference Example 31, by using 6-ethoxycarbonyl-7-hydroxy-3-[3-methyl-4-(3-methylphenylmethyl)]phenylpyrazolo[1,5-a]pyrimidine (1.43 g), there was prepared the title compound (1.31 g).

mp: 182°–187° C. (foamed)

NMR (DMSO-d$_6$) δ: 8.45 (s, 1H), 8.34 (s, 1H), 7.2–7.6 (m, 2H), 7.1–7.3 (m, 2H), 6.9–7.1 (m, 3H), 3.95 (s, 2H), 2.27 (s, 3H), 2.26 (s, 3H)

Example 30

Preparation of 7-hydroxy-3-[3-methyl-4-(3-methylphenylmethyl) phenylpyrazolo[1,5-a]pyrimidine In the same manner as in Example 2, by using 6-carboxy-7-hydroxy-3-[3-methyl-4-(3-methylphenylmethyl)]phenylpyrazolo[1,5-a]pyrimidine (1.2 g), there was prepared the title compound (1.02 g).

mp: 293°–299° C. (decomposed)

NMR (DMSO-d$_6$) δ: 8.18 (s, 1H), 7.81 (dd, J=7.26Hz, 5.78Hz, 1H), 7.3–7.4 (m, 2H), 7.1–7.3 (m, 2H), 6.9–7.1 (m, 3H), 5.77 (d, J=7.26Hz, 1H), 3.95 (s, 2H), 2.28 (s, 3H), 2.26 (s, 3H)

Reference Example 48

(1) Preparation of 4-(1,3-dioxolan-2-yl)-3',4'-methylenedioxybenzhydrol

To a suspension of magnesium (0.45 g, 19 millimol) in tetrahydrofuran (20 ml) was added a small amount of iodine. To the mixture was added a solution of p-bromobenzaldehyde ethylene acetal (3.85 g, 16.8 millimol) in tetrahydrofuran (10 ml). After a while, heat was generated, and magnesium was dissolved. After stirring for 2 hours as it was, the mixture was cooled with ice, and thereto was added piperonale (2.55 g, 16.8 millimol) at a breath. After stirring for 1 hour as it was, saturated ammonium chloride solution was added, and the mixture was extracted with ethyl acetate. The organic layer was washed with water, dried over anhydrous sodium sulfate, and the solvent was distilled away. The residue was separated and purified by using a silica-gel column chromatography (ethyl acetate:n-hexane=1:2) to give the title compound (3.6 g, 12 millimol, 71%).

NMR (CDCl₃) δ: 7.46 (d, J=8.25Hz, 2H), 7.38 (d, J=8.58Hz, 2H), 6.82–6.84 (m, 2H), 6.75 (d, J=8.58Hz, 1H), 5.92 (s, 2H), 5.80 (s, 1H), 5.77 (s, 1H), 3.99–4.15 (m, 4H)

(2) Preparation of α-acetoxy-4-(1,3-dioxolan-2-yl)-3',4'-methylenedioxydiphenylmethane 4-(1,3-Dioxolan-2-yl)-3',4'-methylenedioxybenzhydrol (3.6 g, 12 millimol) was dissolved in methylene chloride (10 ml), and thereto were added pyridine (1.1 ml, 14.4 millimol) and 4-dimethylaminopyridine (150 mg, 1.2 millimol), and the mixture was cooled with ice. After adding acetyl chloride (1.2 ml, 14.4 millimol) to the mixture, the ice bath was removed off, and the mixture was stirred for 2 hours. To the mixture was added water, and the mixture was extracted with ethyl acetate. The organic layer was washed with 10% hydrochloric acid, water and saturated aqueous sodium chloride solution, dried over anhydrous sodium sulfate, and the solvent was distilled away under reduced pressure to give the title compound (4.4 g, 12 millimol, 100%)

NMR (CDCl₃) δ: 7.45 (d, J=8.25Hz, 2H), 7.34 (d, J=7.92Hz, 2H), 6.80 (s, 1H), 6.78–6.82 (m, 2H), 6.74 (d, J=7.92Hz, 1H), 5.93 (s, 2H), 5.80 (s, 1H), 4.02–4.14 (m, 4H), 2.14 (s, 3H)

(3) Preparation of α-acetoxy-4-formyl-3',4'-methylenedioxydiphenylmethane

α-Acetoxy-4-(1,3-dioxolan-2-yl)-3',4'-methylenedioxydiphenylmethane (9.6 g, 28 millimol) was dissolved in tetrahydrofuran (60 ml), and thereto was added 10% hydrochloric acid (20 ml). After stirring at room temperature for 30 minutes as it was, to the mixture was added saturated aqueous sodium hydrogencarbonate solution, and the mixture was extracted with ethyl acetate. The organic layer was washed with water and saturated aqueous sodium chloride solution in turn, dried over anhydrous sodium sulfate, and the solvent was distilled away under reduced pressure to give the title compound (8.3 g, 28 millimol, 100%).

NMR (CDCl₃) δ: 10.01 (s, 1H), 7.86 (d, J=8.6Hz, 2H), 7.50 (d, J=8.3Hz, 2H), 6.74–6.84 (m, 4H), 5.95 (s, 2H), 2.18 (s, 3H)

(4) Preparation of 4-hydroxymethyl-3',4'-methylenedioxydiphenylmethane

α-Acetoxy-4-formyl-3',4'-methylenedioxydiphenylmethane (8.3 g, 28 millimol) was dissolved in ethyl acetate (50 ml), and thereto was added 5% palladium carbon (1 g). The mixture was stirred at room temperature for 16.5 hours under hydrogen atmosphere, palladium carbon was removed by filtration. After distilling the solvent away under reduced pressure, to the residue was added n-hexane, and the precipitate was separated by filtration to give the title compound (5.8 g, 24 millimol, 86%).

NMR (CDCl₃) δ: 7.29 (d, J=8.3Hz, 2H), 7.17 (d, J=8.0Hz, 2H), 6.73 (d, J=8.6Hz, 1H), 6.64–6.67 (m, 2H), 5.91 (s, 2H), 4.66 (s, 2H), 3.89 (s, 2H)

(5) Preparation of 4-chloromethyl-3',4'-methylenedioxydiphenylmethane

In the same manner as in Reference Example 3, by using 4-hydroxymethyl-3',4'-methylenedioxydiphenylmethane (1.73 g), there was prepared the title compound (1.86 g).

NMR (CDCl₃) δ: 7.30 (d, J=8.25Hz, 2H), 7.16 (d, J=8.25Hz, 2H), 6.7–6.8 (m, 1H), 6.6–6.7 (m,2H), 5.91 (s, 2H), 4.56 (s, 2H), 3.89 (s, 2H)

In the same manner as mentioned above, by using the residual starting material (5.30 g), there was prepared the title compound (5.70 g), and this product was combined with the product previously prepared to use in a subsequent step.

(6) Preparation of 4-(3,4-methylenedioxyphenylmethyl)phenylacetonitrile

In the same manner as in Reference Example 4, by using 4-chloromethyl-3', 4'-methylenedioxydiphenylmethane (7.56 g), there was prepared the title compound (7.15 g).

NMR (CDCl₃) δ: 7.24 (d, J=8.25Hz, 2H), 7.18 (d, J=8.25Hz, 2H), 6.7–6.8 (m, 1H), 6.5–6.7 (m, 2H), 5.92 (s, 2H), 3.89 (s, 2H), 3.71 (s, 2H)

(7) Preparation of 3-amino-2-carbamoyl-4-[4-(3,4-methylenedioxyphenylmethyl)phenyl]pyrazole In the same manner as in Reference Examples 5 and 6, by using 4-(3,4-methylenedioxyphenylmethyl)phenylacetonitrile (7.15 g), there was prepared the title compound (8.26 g).

NMR (DMSO-d₆) δ: 7.67 (s, 1H), 7.6–7.7 (b, 2H), 7.38 (d, J=8.24Hz, 2H), 7.21 (d, J=7.92Hz, 2H), 6.81 (d, J=7.92Hz, 1H), 6.80 (s, 1H), 6.71 (dd, J=7.92, 1.32Hz, 1H), 6.56 (b, 2H), 5.95 (s, 2H), 3.83 (s, 2H)

Example 31

Preparation of 4-hydroxy-8-[4-(3,4-methylenedioxyphenylmethyl)phenyl]pyrazolo[1,5-a]-1,3,5-triazine In the same manner as in Example 1, by using 3-amino-2-carbamoyl-4-[4-(3,4-methylenedioxyphenylmethyl)phenyl]pyrazole (1.00 g), there was prepared the title compound (0.45 g).

mp: >300° C. (decomposed)

NMR (DMSO-d₆) δ: 8.54 (s, 1H), 8.10 (s, 1H), 7.92 (d, J=8.25Hz, 2H), 7.28 (d, J=8.25Hz, 2H), 6.7–6.9 (m, 3H), 5.95 (s, 2H), 3.86 (s, 2H)

Reference Example 49

(1) Preparation of 3,5-dimethoxy-4'-(1,3-dioxolan-2-yl)benzhydrol

To a suspension of magnesium (0.9 g, 37 millimol) in tetrahydrofuran (30 ml) was added a small amount of iodine, and thereto was added a solution of p-bromobenzaldehyde ethylene acetal (8.0 g, 33 millimol) in tetrahydrofuran (10 ml) under nitrogen atmosphere. After a while, heat was generated, and magnesium was dissolved. After stirring for 1.5 hours as it was, the mixture was cooled with ice, and thereto was added at a breath 3,5-dimethoxybenzaldehyde (5 g, 30 millimol). After stirring for 2 hours as it was, saturated aqueous ammonium chloride solution was added, and the mixture was extracted with ethyl acetate. The organic layer was washed with water, and dried over anhydrous sodium sulfate, and the solvent was distilled away under reduced pressure. The residue was separated and purified by using a silica-gel column chromatography (ethyl acetate:n-hexane=1:2) to give the title compound (8.8 g, 27.7 millimol, 92%).

NMR (CDCl₃) δ: 7.45 (d, J=8.5Hz, 2H), 7.40 (d, J=8.57Hz, 2H), 6.53 (d, J=2.31Hz, 2H), 6.35 (t, J=2.31Hz, 1H), 5.80 (s, 1H), 5.77 (s, 1H), 3.99–4.14 (m, 4H), 3.76 (s, 6H)

(2) Preparation of α-acetoxy-3,5-dimethoxy-4-(1,3-dioxolan-2-yl)diphenylmethane 3,5-Dimethoxy-4'-(1,3-dioxolan-2-yl)benzhydrol (8.8 g, 27.7 millimol) was dissolved in methylene chloride (30 ml), and thereto was added pyridine (2.7 ml, 33.2 millimol) and 4-dimethylaminopyridine (0.7 g, 5.5 millimol), and the mixture was cooled with ice. After acetyl chloride (2.4 ml, 33.2 millimol) was added, ice bath was removed, and the mixture was stirred for 3 hours. To the mixture was added water, and the mixture was extracted with ethyl acetate. The organic layer was washed with 10% hydrochloric acid, water and saturated aqueous sodium chloride solution, and dried over anhydrous sodium sulfate. The solvent was distilled away under reduced pressure to give the title compound (10.3 g) at a quantitative yield.

NMR (CDCl$_3$) δ: 7.45 (d, J=8.25Hz, 2H), 7.36 (d, J=8.25Hz, 2H), 6.79 (s, 1H), 6.48 (d, J=2.31Hz, 2H), 6.36 (t, J=2.31Hz, 1H), 5.80 (s, 1H), 3.99–4.14 (m, 4H), 3.76 (s, 6H), 2.15 (s, 3H)

(3) Preparation of α-acetoxy-3,5-dimethoxy-4-formyldiphenylmethane

α-Acetoxy-3,5-dimethoxy-4-(1,3-dioxolan-2-yl)-diphenylmethane (10.3 g, 28 millimol) was dissolved in tetrahydrofuran (60 ml), and thereto was added 10% hydrochloric acid (20 ml). After stirring for 30 minutes as it was, saturated sodium hydrogencarbonate solution was added, and the mixture was extracted with ethyl acetate. The organic layer was washed with water and saturated aqueous sodium chloride solution, dried over anhydrous sodium sulfate, and the solvent was distilled away under reduced pressure to give the title compound (8.8 g, 28 millimol, 100%).

NMR (CDCl$_3$) δ: 10.00 (s, 1H), 7.86 (d, J=8.58Hz, 2H), 7.52 (d, J=8.24Hz, 2H), 6.81 (s, 1H), 6.48 (d, J=1.98Hz, 2H), 6.39 (t, J=2.31Hz, 1H), 3.77 (s, 6H), 2.19 (s, 3H)

(4) Preparation of 3,5-dimethoxy-4′-hydroxymethyldiphenylmethane

α-Acetoxy-3,5-dimethoxy-4-formyldiphenylmethane (8.8 g, 28 millimol) was dissolved in ethyl acetate (50 ml), and thereto was added 5% palladium carbon (1 g). After stirring for 15 hours at room temperature under hydrogen atmosphere, palladium carbon was removed by filtration. The solvent was distilled away under under reduced pressure, and to the residue was added n-hexane. The precipitate was separated by filtration to give the title compound (5.6 g, 22 millimol, 79%).

NMR (CDCl$_3$) δ: 7.28 (d, J=8.25Hz, 2H), 7.18 (d, J=8.25Hz, 2H), 6.31–6.33 (m, 3H), 4.64 (s, 2H), 3.90 (s, 2H), 3.74 (s, 6H)

(5) Preparation of 4′-chloromethyl-3,5-dimethoxydiphenylmethane

In the same manner as in Reference Example 3, by using 3,5-dimethoxy-4′-hydroxymethyldiphenylmethane (5.10 g), there was prepared the title compound (5.46 g).

NMR (CDCl$_3$) δ: 7.30 (d, J=8.25Hz, 2H), 7.18 (d, J=8.25Hz, 2H), 6.3–6.4 (m, 3H), 4.56 (s, 2H), 3.90 (s, 2H), 3.75 (s, 6H)

(6) Preparation of 4-(3,5-dimethoxyphenylmethyl)-phenylacetonitrile

In the same manner as in Reference Example 4, by using 4′-chloromethyl-3,5-dimethoxydiphenylmethane (5.46 g), there was prepared the title compound (5.19 g).

NMR (CDCl$_3$) δ: 7.1–7.3 (m, 4H), 6.3–6.4 (m, 3H), 3.90 (s, 2H), 3.75 (s, 6H), 3.71 (s, 2H)

(7) Preparation of 3-amino-2-carbamoyl-4-[4-(3,5-dimethoxyphenylmethyl)phenyl]pyrazole In the same manner as in Reference Examples 5 and 6, by using 4-(3,5-dimethoxyphenylmethyl)phenylacetonitrile (5.19 g), there was prepared the title compound (3.55 g).

NMR (DMSO-d$_6$) δ: 7.67 (s, 1H), 7.6–7.7 (b, 2H), 7.39 (d, J=8.24Hz, 2H), 7.24 (d, J=8.24Hz, 2H), 6.57 (b, 2H), 6.41 (d, J=1.98Hz, 2H), 6.32 (t, J=1.98Hz, 1H), 3.92 (s, 2H), 3.70 (s, 6H)

Example 32

Preparation of 4-hydroxy-8-[4-(3,5-dimethoxyphenylmethyl)phenyl]pyrazolo[1,5-a]-1,3,5-triazine In the same manner as in Example 1, by using 3-amino-2-carbamoyl-4-[4-(3,5-dimethoxyphenylmethyl)-phenyl]pyrazole (1.00 g), there was prepared the title compound (0.29 g).

mp: 286°–289° C. (decomposed)

NMR (DMSO-d$_6$) δ: 8.53 (s, 1H), 8.09 (s, 1H), 7.93 (d, J=8.25Hz, 2H), 7.30 (d, J=8.25Hz, 2H), 6.40 (d, J=2.31Hz, 2H), 6.32 (t, J=2.31Hz, 1H), 3.87 (s, 2H), 3.70 (s, 6H)

Reference Example 50

(1) Preparation of 4-acetyl-α,α-dimethyldiphenylmethane

To a solution of α,α-dimethyldiphenylmethane (3.92 g) and acetyl chloride (1.56 g) in chlorobenzene (5 ml) was added aluminium chloride (2.67 g) at a amount of ¼ at a time under ice-cooling with stirring. After the ice bath was removed, the mixture was stirred at room temperature for 8 hours, and the reaction mixture was poured into ice-water, and stirred for 30 minutes. The mixture was extracted with ethyl acetate (30 ml×2).

The organic layer was washed with saturated aqueous sodium chloride solution (30 ml×3), dried over Glauber's salt, concentrated under reduced pressure. The residue was separated and purified by using a silicagel column chromatography (n-hexane:ethyl acetate=20:1) to give the title compound (3.77 g).

NMR (CDCl$_3$) δ: 7.85 (d, J=8.57Hz, 2H), 7.0–7.4 (m, 7H), 2.56 (s, 3H), 1.69 (s, 6H)

(2) Preparation of α,α-dimethyl-4-ethoxycarbonyldiphenylmethane

To a mixture of 4-acetyl-α,α-dimethyldiphenylmethane (3.77 g), sodium hydroxide (5.21 g), dioxane (6 ml) and water (44 ml) was added dropwise bromine (7.58 g) under ice-cooling with stirring. In that case, the temperature of liquid was kept to 10° C. or less. After dropping, the mixture was stirred for 1 hour under ice-cooling, and stirred at room temperature for 3 hours. To the reaction mixture thus obtained was added chloroform (100 ml), and the organic layer was separated. The organic layer was washed with saturated sodium hydrogencarbonate and saturated aqueous sodium chloride solution in turn, dried over Glauber's salt, concentrated under reduced pressure.

To the residue were added ethanol (100 ml) and conc. sulfuric acid (5 ml), and the mixture was heated and refluxed for 4 hours. After ice-water was poured, the mixture was extracted with ethyl acetate (100 ml×2). The organic layer was washed with saturated aqueous sodium chloride solution, dried over Glauber's salt, concentrated under reduced pressure to give the title compound (4.27 g).

NMR (CDCl$_3$) δ: 7.93 (d, J=8.25Hz, 2H), 7.0–7.4 (m, 7H), 4.35 (q, J=7.03Hz, 2H), 1.69 (s, 6H), 1.37 (t, J=7.03Hz, 3H)

(3) Preparation of α,α-dimethyl-4-hydroxymethyldiphenylmethane

In the same manner as in Reference Example 2, by using α,α-dimethyl-4-ethoxycarbonyldiphenylmethane (4.25 g), there was prepared the title compound (3.20 g).

NMR (CDCl$_3$) δ: 7.0–7.4 (m, 9H), 4.64 (s, 2H), 1.68 (s, 6H)

(4) Preparation of 4-chloromethyl-α,α-dimethyldiphenylmethane

In the same manner as in Reference Example 3, by using α,α-dimethyl-4-hydroxymethyldiphenylmethane (3.20 g), there was prepared the title compound (3.46 g).

NMR (CDCl$_3$) δ: 7.0–7.4 (m, 9H), 4.56 (s, 2H), 1.67 (s, 6H)

(5) Preparation of 4-(2-Phenylpropan-2-yl)phenylacetonitrile

In the same manner as in Reference Example 4, by using 4-chloromethyl-α,α-dimethyldiphenylmethane (3.46 g), there was prepared the title compound (3.15 g).

NMR (CDCl$_3$) δ: 7.0–7.4 (m, 9H), 3.69 (s, 2H), 1.67 (s, 6H)

(6) Preparation of 3-amino-2-carbamoyl-4-[4-(2-phenylpropan-2-yl)phenyl]pyrazole In the same manner as in Reference Examples 5 and 6, by using 4-(2-phenylpropan-2-yl)phenylacetonitrile (3.15 g), there was prepared the title compound (2.67 g).

NMR (DMSO-d$_6$) δ: 7.67 (s, 1H), 7.61–7.63 (b, 2H), 7.13–7.63 (m, 9H), 6.58 (b, 2H), 1.63 (s, 6H)

Example 33

Preparation of 4-hydroxy-8-[4-(2-phenylpropan-2-yl)phenyl]pyrazolo[1,5-a]-1,3,5-triazine In the same manner as in Example 1, by using 3-amino-2-carbamoyl-4-[4-(2-phenylpropan-2-yl)phenyl]pyrazole (0.99 g), there was prepared the title compound (0.53 g).

mp: 288°–290° C. (decomposed)

NMR (DMSO-d$_6$) δ: 8.52 (s, 1H), 8.10 (s, 1H), 7.89 (d, J=8.58 Hz, 2H), 7.1–7.3 (m, 7H), 1.66 (s, 6H)

Reference Example 51

(1) Preparation of 3-amino-4-[4-(2-phenylpropan-2-yl)phenyl]pyrazole

To a suspension of 3-amino-2-carbamoyl-4-[4-(2-phenylpropan-2-yl)phenyl]pyrazole (1.5 g) in methanol (20 ml) was added 5N sodium hydroxide solution (2 l), and the mixture was refluxed. To the mixture was added water (50 ml) under ice-cooling, and the mixture was neutralized (pH 7 to 8) with 10% hydrochloric acid solution, and was extracted with chloroform. The organic layer was washed with water and saturated aqueous sodium chloride, dried over anhydrous potassium carbonate, and the solvent was distilled away under reduced pressure. The residue was separated and purified by using a silica-gel column chromatography (chloroform:methanol=1:3) to give the title compound (980 mg, 75.5%).

NMR (CDCl$_3$) δ: 7.54 (s, H), 7.13–7.32 (m, 9H), 4.47 (b, 3H), 1.70 (s, 6H)

(2) Preparation of 6-ethoxycarbonyl-7-hydroxy-3-[4-(2-phenylpropan-2-yl)phenyl]pyrazolo[1,5-a]pyrimidine To a suspension of 3-amino-4-[4-(2-phenylpropan-2-yl)phenyl]pyrazole (920 mg) in ethanol (10 ml) was added diethyl ethoxymethylenemalonate (1.34 ml), and the mixture was heated and refluxed for 3 days. To the mixture was added sodium methoxide (540 mg) under ice-cooling, and the mixture was stirred for 1 day. Ethanol was distilled away under reduced pressure, and thereto was added water (50 ml) under ice-cooling. The mixture was adjusted to acid with 10% hydrochloric acid, and the precipitate was separated by filtration, washed with water to give the title compound (1.26 g, 94.6%).

NMR (DMSO-d$_6$) δ: 8.35 (s, 1H), 8.19 (s, 1H), 7.49 (d, J=8.37Hz, 2H), 7.15–7.33 (m, 7H), 4.26 (q, J=7.29Hz, 2H), 1.69 (s, 6H), 1.30 (t, J=7.29Hz, 3H)

(3) Preparation of 6-carboxy-7-hydroxy-3-[4-(2-phenylpropan-2-yl)phenyl]pyrazolo[1,5-a]pyrimidine To a solution of 6-ethoxycarbonyl-7-hydroxy-3-[4-(2-phenylpropan-2-yl)phenyl]pyrazolo[1,5-a]pyrimidine (1.2 g) in ethanol (20 ml) was added 5N sodium hydroxide solution (3.0 ml), and the mixture was heated and refluxed for 20 hours. The solvent was distilled away under reduced pressure, and thereto was added water (100 ml) under ice-cooling. The mixture was adjusted to acid with 10% hydrochloric acid, and the precipitate was separated by filtration, washed with water to give the title compound (1.0 g, 89.6%).

NMR (DMSO-d$_6$) δ: 8.43 (s, 1H), 8.31 (s, 1H), 7.56 (d, J=4.05Hz, 2H), 7.25–7.33 (m, 6H), 7.15–7.21 (m, 1H), 1.69 (s, 6H)

Example 34

Preparation of 7-hydroxy-3-[4-(2-phenylpropan-2-yl)phenyl]pyrazolo[1,5-a]pyrimidine To 6-carboxy-7-hydroxy-3-[4-(2-phenylpropan-2-yl)phenyl]pyrazolo[1,5-a]pyrimidine (950 mg) was added aniline (7.0 ml), and the mixture was stirred at 100° C. for 3 hours. To the reaction mixture was added water (20 ml) under ice-cooling. The mixture was adjusted to acid with 10% hydrochloric acid, and the precipitate was separated by filtration, washed with 30% methanol-water to give the title compound (830 mg) at a quantitative yield.

mp: 290°–300° C. (decomposed)

NMR (DMSO-d$_6$) δ: 8.14 (s, 1H), 7.77 (d, J=7.29Hz, 1H), 7.48 (d, J=8.34Hz, 2H), 7.25–7.31 (m, 5H), 7.15–7.20 (m, 2H), 5.76 (d, J=7.29Hz, 1H), 1.69 (s, 6H)

Reference Example 52

(1) Preparation of 3-amino-4-[4-(3,4-methylenedioxyphenylmethyl)phenyl]pyrazole

To a suspension of 3-amino-2-carbamoyl-4-[4-(3,4-methylenedioxyphenylmethyl)phenyl]pyrazole (2.0 g) in methanol (20 ml) was added 5N sodium hydroxide solution (2.0 ml), and the mixture was refluxed for 1 hour. The solvent was distilled away under reduced pressure, and thereto was added water (50 ml) under ice-cooling. The mixture was neutralized (pH 7 to 8) with 10% hydrochloric acid, and the precipitate was separated by filtration, washed with chloroformdiethyl ether to give the title compound (1.3 g, 74.0%).

NMR (CDCl$_3$) δ: 7.45 (s, 1H), 7.35 (d, J=8.37Hz, 2H), 7.19 (d, J=8.37Hz, 2H), 6.20–6.76 (m, 3H), 5.90 (s, 2H), 3.89 (s, 2H)

(2) Preparation of 6-ethoxycarbonyl-7-hydroxy-3-[4-(3,4-methylenedioxyphenylmethyl)phenyl]-pyrazolo[1,5-a]pyrimidine To a solution of 3-amino-4-[4-(3,4-methylenedioxyphenylmethyl)phenyl]pyrazole (1.5 g) in ethanol (10 ml) was added diethyl ethoxymethylenemalonate (2.07 ml), and the mixture was heated and refluxed for 12 hours. To the mixture was added sodium methoxide (829 mg) under ice-cooling, and the mixture was stirred at room temperature for 1 day. The solvent was distilled away under reduced pressure, and thereto was added water (50 ml) under ice-cooling. The mixture was adjusted to acid with 10% hydrochloric acid, and the precipitate was separated by filtration, washed with water to give the title compound (2.1 g) at a quantitative yield.

NMR (DMSO-d$_6$) δ: 8.48 (s, 1H), 8.16 (s, 1H), 7.88 (d, J=7.92Hz, 2H), 7.21 (d, J=8.25Hz, 2H), 6.69–6.81 (m, 3H), 5.94 (s, 2H), 4.20 (q, J=6.75Hz, 2H), 3.84 (s, 2H), 1.28 (t, J=6.75Hz, 3H)

(3) Preparation of 6-carboxy-7-hydroxy-3-[4-(3,4-methylenedioxyphenylmethyl)phenyl]pyrazolo[1,5-a]pyrimidine To a solution of 6-ethoxycarbonyl-7-hydroxy-3-[4-(3,4-methylenedioxyphenylmethyl)phenyl]-pyrazolo[1,5-a]pyrimidine (1.2 g) in ethanol (60 ml) was added 5N sodium hydroxide solution (3.0 ml), and the mixture was heated and refluxed for 20 hours. The solvent was distilled away under reduced pressure, and thereto was added water (100 ml) under ice-cooling. The mixture was adjusted to acid with 10% hydrochloric acid, and the precipitate was separated by filtration, washed with water to give the title compound (1.0 g, 89.3%).

NMR (DMSO-$d_6$) δ: 8.44 (s, 1H), 8.30 (s, 1H), 7.54 (d, J=7.91Hz, 2H), 7.43 (d, J=7.92Hz, 2H), 6.80–6.83 (m, 2H), 6.71–6.75 (m, 1H), 5.95 (s, 2H), 3.89 (s, 2H)

Example 35

Preparation of 7-hydroxy-4-[4-(3,4-methylenedioxyphenylmethyl)phenyl]pyrazolo[1,5-a]pyrimidine To 6-carboxy-7-hydroxy-3-[4-(3,4-methylenedioxyphenylmethyl)phenyl]pyrazolo[1,5-a]pyrimidine (1.65 g) was added aniline (10 ml), and the mixture was stirred at 100° C. for 3 hours. To the reaction mixture was added water (5 ml) under ice-cooling. The mixture was adjusted to acid with 10% hydrochloric acid, and the precipitate was separated by filtration, washed with methanol-water (3:7) and methanol-diethyl ether (5:95) to give the title compound (1.25 g, 85.4%).

mp: 245°–253° C. (decomposed)

NMR (DMSO-$d_6$) δ: 8.14 (s, 1H), 7.77 (d, J=7.29Hz, 1H), 7.48 (d, J=8.37Hz, 2H), 7.31 (d, J=8.37Hz, 2H), 6.80–6.83 (m, 2H), 6.69–6.75 (m, 1H), 5.95 (s, 2H), 5.76 (d, J=7.56Hz, 1H), 3.84 (s, 2H)

Reference Example 53

This Reference Example is to prepare the intermediate of the compound of the invention, which is identical with the title compound of step (3) of Reference Example 22.

(1) Preparation of 3-methoxybenzyltosylate

To tetrahydrofuran (10 ml) was suspended 60% aqueous sodium hydride solution (480 mg, 12 millimol). To mixture was added dropwise a solution of 3-methoxybenzyl alcohol (1.38 g) in tetrahydrofuran (5 ml) under nitrogen atmosphere, and the mixture was stirred at room temperature for 20 minutes. After cooling with methanol-ice, to the reaction liquid was added dropwise a solution obtained by dissolving tosylchloride (2.3 g, 12 millimol) in tetrahydrofuran (5 ml), After dropping, the mixture was returned to room temperature, and stirred for 15 hours. After adding a small amount of ethanol, the mixture was diluted with ether, and the insoluble material was removed by filtration.

After separating the solvent by filtration, n-hexane was added, and the precipitate was separated by filtration to give the title compound (2.42 g, 8.3 millimol, 83%).

NMR (CDCl$_3$) δ: 7.80 (d, J=8.2Hz, 2H), 7.32 (d, J=7.9Hz, 2H), 7.22 (t, J=7.9Hz, 1H), 6.76–6.87 (m, 3H), 5.03 (s, 2H), 3.76 (s, 3H), 2.44 (s, 3H)

(2) Preparation of 4-(3-methoxyphenylmethyl)benzaldehyde ethlyene acetal

To a solution of 4-bromobenzaldehyde ethylene acetal (1.5 g, 6.5 millimol) in tetrahydrofuran (7 ml) were added magnesium (170 mg, 7 millimol) and a small amount of iodine, and the mixture was vigorously stirred under nitrogen atmosphere. After most of magnesium was dissolved, the solution was added to a solution of 3-methoxybenzyltosylate (1.46 g, 5 millimol) and copper(I) bromidedimethylsulfide complex (50 mg, 0.25 millimol) in benzene (14 ml). The mixture was stirred at room temperature for 22 hours. Next, saturated ammonium chloride solution was added, and the mixture was extracted with ethyl acetate, the organic layer was washed with water, dried over anhydrous sodium sulfate, and the solvent was distilled away under reduced pressure, The residue was separated and purified by using a silica-gel column chromatography (ethyl acetate:n-hexane=1:3) to give the title compound (850 mg, 3.14 millimol, 63%).

NMR (CDCl$_3$) δ: 7.39 (d, J=8.2Hz, 2H), 7.16–7.22 (m, 3H), 6.72–6.78 (m, 3H), 5.79 (s, 1H), 4.02–4.15 (m, 4H), 3.96 (s, 2H), 3.76 (s, 3H)

(3) Preparation of 4-(3-methoxyphenylmethyl)benzaldehyde 4-(3-Methoxyphenylmethyl)benzaldehyde ethylene acetal (700 mg, 2.6 millimol) was dissolved in tetrahydrofuran (5 ml), and thereto was added 10% hydrochloric acid. After stirring at room temperature for 30 minutes, to the mixture was added saturated aqueous sodium chloride solution, and the mixture was extracted with ethyl acetate. The extract was washed, dried over anhydrous sodium sulfate, and the solvent was distilled away to give the title compound (580 mg, 2.6 millimol, 100%).

NMR (CDCl$_3$) δ: 9.97 (s, 1H), 7.80 (d, J=8.3Hz, 2H), 7.35 (d, J=7.9Hz, 2H), 7.22 (t, J=7.6Hz, 1H), 6.71–6.79 (m, 3H), 4.03 (s, 2H), 3.78 (s, 3H)

(4) Preparation of 4-hydroxymethyl-3'-methoxydiphenylmethane 4-(3-Methoxyphenylmethyl)benzaldehyde (580 mg, 2.6 millimol) was dissolved in ethanol (5 ml), and was cooled with ice. To the mixture was added sodium borohydride (100 mg, 2.6 millimol), and the mixture was stirred for 30 minutes. After excessive sodium borohydride was decomposed with acetone, and saturated aqueous sodium chloride solution was added. The mixture was extracted with ethyl acetate. The organic layer was dried over anhydrous sodium sulfate, and the solvent was distilled away to give the title compound (580 mg, 2.6 millimol, 100%). The compound thus obtained is identical with the title compound in the step (3) of Reference Example (22).

Reference Example 54

Preparation of 4-bromobenzaldehyde ethylene acetal

To a solution of 4-bromobenzaldehyde (102 g, 0.55 mol) and ethylene glycol (100 g, 1.65 mol) in benzene (1 l) were added a small amount of 10-camphorsulfonic acid, and the mixture was refluxed for 3 hours, while water was removed with Dean-Stark. After allowing to cool, saturated sodium hydrogencarbonate solution was added, and the mixture was extracted with ethyl acetate. The organic layer was washed with water, dried over anhydrous sodium sulfate, and the solvent was distilled to give the title compound (126 g, 0.55 mol, 100%).

The obtained compound is a starting material in the step (2) of Reference Example 53 and the step (2) of next Reference Example 55.

NMR (CDCl$_3$) δ: 7.51 (d, J=8.6Hz, 2H), 7.35 (d, J=8.3Hz, 2H), 5.77 (s, 1H), 3.98–4.15 (m, 4H)

Reference Example 55

This is the other example for preparing the compound identical with the objective compound in the (3) of Reference Example 28.

(1) Preparation of 3-chlorobenzyltosylate

To tetrahydrofuran (30 ml) was suspended 60% aqueous sodium hydride solution (3.52 g, 88 millimol). To mixture was added dropwise a solution of 3-chlorobenzyl alcohol (11.4 g, 80 millimol) in tetrahydrofuran (80 ml) under nitrogen atmosphere, and the mixture was stirred at room temperature for 20 minutes. After cooling with methanol-ice, to the reaction liquid was added dropwise a solution obtained by dissolving tosylchloride (16.8 g, 88 millimol) in tetrahydrofuran (80 ml). After dropping, the mixture temperature was returned to room temperature, and stirred for 19 hours. After adding a small amount of ethanol, the mixture was diluted with ether, and the insoluble material was removed by filtration. After distillating the solvent away, n-hexane was added, and the precipitate was separated by filtration to give the title compound (19.1 g, 64 millimol, 80%).

NMR (CDCl$_3$) δ: 7.78 (d, J=8.2Hz, 2H), 7.13–7.34 (m, 6H), 5.02 (s, 2H), 2.45 (s, 3H)

(2) Preparation of 4-(3-chlorophenylmethyl)benzaldehyde ethylene acetal

To a solution of 4-bromobenzaldehyde ethylene acetal (16.0 g) in tetrahydrofuran (70 ml) were added magnesium (1.87 g) and iodine (catalytic amount), and the mixture was stirred at room temperature under nitrogen atmosphere. A Grignard reagent was formed, and the mixture was stirred for 15 minutes from generating heat, and further stirred for 45 minutes at 50° to 60° C., and the temperature was returned to room temperature.

On the other hand, to a solution of 3-chlorobenzyltosylate (14.8 g) in benzene (140 ml) was added copper(I) bromide-dimethylsulfide complex (1.0 g), and the mixture was stirred at room temperature under nitrogen atmosphere. To the mixture was added dropwise the Grignard reagent mentioned-above at room temperature. After generating heat, the mixture was stirred at room temperature for 18 hours.

To the mixture were added saturated aqueous ammonium chloride solution (150 ml), and the mixture was extracted with ethyl acetate. The organic layer was washed with saturated aqueous ammonium chloride solution, water, saturated sodium hydrogencarbonate solution and saturated aqueous sodium chloride solution, dried over anhydrous Glauber's salt, and the solvent was distilled away under reduced pressure.

The residue was separated and purified by using a silica-gel column chromatography (ethyl acetate:n-hexane=1:5), and by-products having 80°/1.2 mmHg were removed by using a reduced pressure distillation to give the purified title compound (12.1 g, 87.8%).

NMR (CDCl$_3$) δ: 7.36 (d, J=8.31Hz, 2H), 7.15–7.23 (m, 5H), 7.02–7.08 (m, 1H), 5.79 (s, 1H), 3.98–4.18 (m, 4H), 3.96 (s, 2H)

(3) Preparation of 4-(3-chlorophenylmethyl)benzaldehyde

To a solution of 4-(3-chlorophenylmethyl)benzaldehyde ethylene acetal (19.9 g) in tetrahydrofuran (80 ml) was added dropwise 10% hydrochloric acid (25.0 ml). After stirring for 15 minutes under ice-cooling, tetrahydrofuran was removed by using a reduced pressure distillation, and the residue was extracted with ethyl acetate. The organic layer was washed with water, saturated aqueous sodium hydrogencarbonate solution and saturated aqueous sodium chloride solution, dried over anhydrous magnesium sulfate, and the solvent was distilled away to give the title compound (16.72 g) at a quantitative yield.

NMR (CDCl$_3$) δ: 9.99 (s, 1H), 7.81 (d, J=7.83Hz, 2H), 7.34 (d, J=8.1Hz, 2H), 7.17–7.27 (m, 3H), 7.04–7.10 (m, 1H), 4.03 (s, 2H)

(4) Preparation of 3'-chloro-4-hydroxymethyldiphenylmethane

To a solution of 4-(3-Chlorophenylmethyl)benzaldehyde (15.0 g) in ethanol (100 ml) was added sodium borohydride (1.50 g) little by little under ice-cooling with stirring, and the mixture was stirred for 15 minutes under ice-cooling, and stirred for 10 hours at room temperature. Under ice-cooling, to the mixture were added water (50 ml) and 10% hydrochloric acid (150 ml), and the mixture was extracted with ethyl acetate. The organic layer was washed with 10% hydrochloric acid, water, saturated aqueous sodium hydrogencarbonate solution and saturated aqueous sodium chloride solution, dried over anhydrous magnesium sulfate, and the solvent was distilled away to give the title compound (14.0 g, 92.7%).

NMR (CDCl$_3$) δ: 7.24–7.32 (d, J=8.10Hz, 2H), 7.16–7.24 (m, 5 H), 7.05–7.08 (m, 1H), 4.67 (d, J=5.67Hz, 2H), 3.95 (s, 2H), 1.60 (t, J=5.67Hz, 1H)

The compound thus obtained is identical with the title compound in step (3) of Reference Example 28, and it appears that a few difference of NMR is due to difference of concentration.

Pharmaceutical Example is explained below.

| Pharmaceutical Example | |
|---|---|
| 8-(4-benzylphenyl)-4-hydroxy-pyrazolo[1,5-a]-1,3,5-triazine (Example 1) | 100 g |
| Avicel (trademark, Asahi Chemical Industry Co., Ltd.) | 40 g |
| Corn starch | 30 g |
| Magnesium stearate | 2 g |
| TC-5 (trademark, hydroxypropylmethylcellulose availble from Shin-Etsu Chemical Co., Ltd.) | 10 g |
| Polyethylene glycol-6000 | 3 g |
| Castor oil | 40 g |
| Ethanol | 40 g |

After kneading 8-(4-benzylphenyl)-4-hydroxypyrazolo[1,5-a]-1,3,5-triazine, Avicel, corn starch, and magnesium stearate, tablets were prepared by using tableting machine for sugar coated tablet R10 mm. The obtained tablets were coated with film composed of polyethylene glycol 6000, castor oil and ethanol, and the film coated tablets in the composition specified above were manufactured.

The compounds obtained in Examples were evaluated in the following pharmacological studies.

1. Assay of inhibitory activity to binding of $^3$H-mibolerone on rat prostate androgen receptor (1) Preparation of cytosol from rat prostate The rats were killed 24 hours after castration, and the ventral prostate glands were removed, and was gently homogenized, with three volume of buffer solution A (1.5 mM EDTA, 2 mM dithiothreitol, 10 mM molybdate sodium, 10% by volume of glycerol, 10 mM NaF, 25 mM phosphate sodium, pH 7.2) on ice-water bath, in Polytron, and Potter type homogenizer. The obtained homogenate was filtrated through double gauze, and centrifuged at 105,000×g for 60 minutes at 4° C., and the supernatant was obtained as cytoplasm fraction.

(2) Measurement of specific binding of $^3$H-mibolerone to prostate cytoplasm androgen receptor To the cytoplasm fraction obtained in (1) was added $^3$H-mibolerone (87.0 Ci/millimol), so that a final concentration is adjusted to 1 nM, and at the same time, in order to block binding of $^3$H-mibolerone to progestin receptor, triamsinolone acetonide was added to a final concentration of 5 μM, and the final volume was adjusted to 0.4 ml with buffer solution A, and the reaction mixture was incubated for 20 hours at 0° C. After incubation, 0.5 ml of 60% hydroxylapatite slurry (washed and equilibrate with a buffer solution B: 10 mM NaH$_2$PO$_4$, 20 mM tris-hydrochloric acid, pH 7.2) was added, and incubated for 10 minutes at 0° C., the solution was transferred onto a glass fiber filter, and washed five times with 5 ml portions of buffer solution B containing 0.1% (weight/volume) of Triton X-100, to remove free $^3$H-mibolerone. This glass fiber was transferred into vial, and 10 ml of aquasol-2 was added, and the radioactivity was measured, and the total binding amount of $^3$H-mibolerone on prostate cytoplasm androgen receptor was determined.

The nonspecific binding amount was determined similarly by adding an unlabeled 5α-DHT in the reaction solution to a final concentration of 1 μM. The difference between the total binding amount and nonspecific binding amount was determined as the specific binding amount on the androgen receptor.

(3) Inhibitory activity of sample compounds on $^3$H-mibolerone specific binding The various concentrations of compounds obtained in the experiments were added simultaneously with $^3$H-mibolerone to incubate same as in (2), and the specific binding amount of $^3$H-mibolerone on androgen receptor was determined. Comparing this value with the value obtained in (2), the IC$_{50}$ value of inhibitory activity of the compounds on $^3$H-mibolerone specific binding was determined. The results are shown in Tables 2 and 3.

The compounds used in Comparative Examples shown in Tables 2 and 3 are shown below.

Comparative Example 1: Flutamide
Comparative Example 2: Hydroxyflutamide

TABLE 1

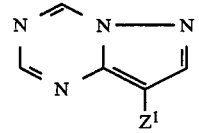

| Comparative Example No. | Z$^1$ |
|---|---|
| 3 | 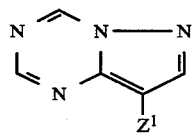 |
| 4 | 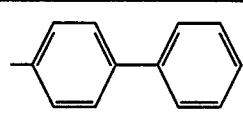 |

TABLE 1-continued

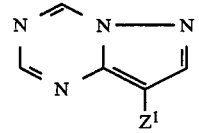

| Comparative Example No. | Z$^1$ |
|---|---|
| 5 | 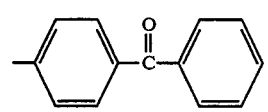 |
| 6 | 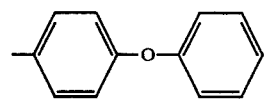 |
| 7 | 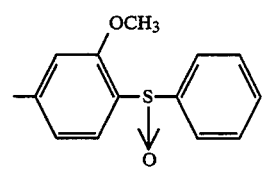 |
| 8 | 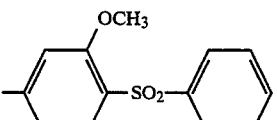 |
| 9 | 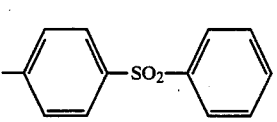 |

The compounds shown in Table 1 are those disclosed in U.S. Pat. No. 4,824,834 except for Comparative Example 6.

TABLE 2

| Test Compound (Example No.) | Inhibitory activity on mibolerone specific binding [IC$_{50}$ (M)] |
|---|---|
| 1 | 2.8 × 10$^{-7}$ |
| 2 | 2.8 × 10$^{-7}$ |
| 3 | 4.0 × 10$^{-7}$ |
| 4 | 7.4 × 10$^{-8}$ |
| 5 | 3.0 × 10$^{-8}$ |
| 6 | 4.0 × 10$^{-7}$ |
| 7 | 6.2 × 10$^{-8}$ |
| 8 | 1.1 × 10$^{-7}$ |
| 9 | 9.5 × 10$^{-8}$ |
| 10 | 1.2 × 10$^{-8}$ |
| 11 | 1.8 × 10$^{-8}$ |
| 12 | 2.3 × 10$^{-8}$ |
| 13 | 1.2 × 10$^{-7}$ |
| 14 | 6.4 × 10$^{-7}$ |
| 15 | 9.9 × 10$^{-8}$ |
| 16 | 3.0 × 10$^{-7}$ |
| 17 | 8.7 × 10$^{-7}$ |
| 19 | 3.9 × 10$^{-8}$ |
| 20 | 2.0 × 10$^{-7}$ |

TABLE 3

| Test compound (Example No.) | Inhibitory activity on mibolerone specific binding [IC$_{50}$ (M)] |
|---|---|

TABLE 3-continued

| Test compound | Inhibitory activity on mibolerone specific binding [IC$_{50}$ (M)] |
|---|---|
| 21 | $1.1 \times 10^{-7}$ |
| 22 | $9.3 \times 10^{-8}$ |
| 23 | $2.6 \times 10^{-8}$ |
| 24 | $2.6 \times 10^{-8}$ |
| 25 | $2.8 \times 10^{-8}$ |
| 26 | $1.3 \times 10^{-8}$ |
| 27 | $8.2 \times 10^{-8}$ |
| 28 | $1.2 \times 10^{-7}$ |
| 29 | $2.0 \times 10^{-8}$ |
| 30 | $2.5 \times 10^{-8}$ |
| 31 | $7.5 \times 10^{-7}$ |
| 32 | $7.7 \times 10^{-7}$ |
| 33 | $1.2 \times 10^{-7}$ |
| 34 | $9.0 \times 10^{-8}$ |
| 35 | $2.2 \times 10^{-7}$ |
| Comparative Example | |
| 1 | $>>>5 \times 10^{-6}$ |
| 2 | $2.0 \times 10^{-6}$ |
| 3 | $>5 \times 10^{-6}$ |
| 4 | $2.0 \times 10^{-6}$ |
| 5 | $4.1 \times 10^{-6}$ |
| 6 | $2.4 \times 10^{-6}$ |
| 7 | $>5 \times 10^{-6}$ |
| 8 | $>5 \times 10^{-6}$ |
| 9 | $>1.9 \times 10^{-6}$ |

2. In vitro drug metabolism in rat liver extract

The resistance of the compound against metabolic degradation by rat liver extract was investigated.

(Method of Experiment)

(1) Animal and liver

The male Wistar rats (weighing about 200 g) were used after fasting for 24 hours. The rat was sacrificed under ether anesthesia, and the livers were removed and were placed onto the ice.

(2) Preparation of enzyme solution for drug metabolism

The liver was minced with scissors under ice-cooling, and homogenized in the presence of 4 volumes of 1.15% KCl-0.1M phosphate buffer (pH 7.4) with a Potter type homogenizer. The homogenates were centrifuged at 9,000×g for 10 minutes at 4° C., and the supernatant filtered through the cheese-cloth was used as an enzyme solution.

(3) Reaction conditions

The constitution of the reaction mixture was shown in below. 0.1M Buffer was sufficiently bubbled in 95% O$_2$-5% CO$_2$ gas before use.

| (Reagnets) | (Amounts) |
|---|---|
| NADP (3.35 mg/ml) | 20 μl |
| Glucose 6-phosphate (60.8 mg.ml) | 20 μl |
| MgCl$_2$.6H$_2$O (101.6 mg/ml) | 20 μl |
| Nicotineamide (9.16 mg/ml) | 20 μl |
| Enzyme solution | 200 μl |
| Test sample (1 μmol/ml) | 5 μl |
| 0.1M Phosphate buffer | 715 μl |

The tested samples were dissolved in dimethyl sulfoxide. MgCl$_2$.6H$_2$O was dissolved in a distilled water, and all other reagents were dissolved in 0.1M phosphate buffer. The reaction was initiated by adding enzyme solution, and shaked at 37° C. with 120 cycles/minutes in Spitz test tubes with stoppers. The reaction was stopped by adding methanol after 5, 15, 30 and 60 minutes.

After termination of the reaction, samples were mixed by using of a Vortex mixer, and centrifuged at 3,000 rpm for 10 minutes. The supernatant was applied to a high-performance liquid chromatography of which conditions are shown in below. A residual amount of the mother compound was determined at certain time intervals, whereby half-life of the compound in the rat liver extract was calculated.

(Conditions for high-performance liquid chromatography)

Column: Chemcosorb 5C18–300 Å 4.6 mm diameter and 150 mm length
Eluent: 55% CH$_3$CN-0.01% TFA
Flow rate: 1 ml/minute
Detection: UV 290 nm
Sensitivity: 0.01 AUFS
Amount of sample: 50 μl
Colume temperature: 50° C.

(Experimental result)

The measurement results are shown in Table 4. For comparison, the results of measurement conducted to the Compounds A1, A2 and A3 disclosed in U.S. Pat. No. 4,824,834 and the Compounds B1 and B2 disclosed in International Publication WO92/06096 are also shown in Table 4.

Substituents in Table 4 correspond with those of the compound expressed by the following chemical formula.

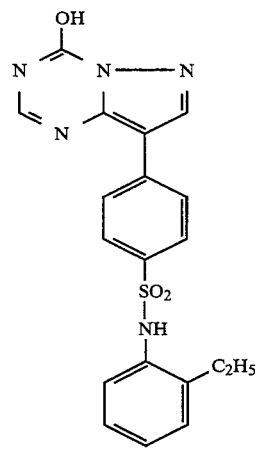

TABLE 4

| Example No. | Sunstituents | | | | Residual amount of test compound | | | | | Half-time period (minute) |
|---|---|---|---|---|---|---|---|---|---|---|
| | A$^0$ | Z$^0$ | R$^1$ | R$^2$ | 0 min. | 5 min. | 15 min. | 30 min. | 60 min. | |
| 1 | N | CH$_2$ | H | H | 100 | 92.2 | 62.4 | 60.2 | 42.9 | 45 |
| 2 | CH | CH$_2$ | H | H | 100 | 81.3 | 86.1 | 84.2 | 80.2 | >60 |
| 4 | N | CH$_2$ | OCH$_3$ | H | 100 | 56.9 | 44.6 | 49.9 | 38.2 | 30 |

TABLE 4-continued

| Example No. | Sunstituents A⁰ | Z⁰ | R¹ | R² | Residual amount of test compound 0 min. | 5 min. | 15 min. | 30 min. | 60 min. | Half-time period (minute) |
|---|---|---|---|---|---|---|---|---|---|---|
| 5 | N | $CH_2$ | $CH_3$ | H | 100 | 93.7 | 89.9 | 82.7 | 83.8 | >60 |
| 10 | N | $CH_2$ | $CH_3$ | 3-$OCH_3$ | 100 | 77.6 | 57.1 | 62.0 | 55.2 | >60 |
| 11 | N | $CH_2$ | $OCH_3$ | 3-$OCH_3$ | 100 | 98.3 | 98.8 | 91.5 | 87.9 | >60 |
| 12 | N | $CH_2$ | $OCH_3$ | 3-$CH_3$ | 100 | 93.0 | 91.8 | 97.4 | 90.8 | >60 |
| 13 | N | $CH_2$ | H | 3-$CH_3$ | 100 | 106.3 | 100.5 | 97.6 | 81.4 | >60 |
| 14 | N | $CH_2$ | H | 2-$CH_3$ | 100 | 82.9 | 77.8 | 82.5 | 55.5 | >60 |
| 15 | N | $CH_2$ | H | 3-$OCH_3$ | 100 | 86.1 | 68.9 | 64.7 | 51.9 | >60 |
| 18 | N | $CH_2$ | H | 4-$OCH_3$ | 100 | 96.5 | 86.2 | 71.6 | 52.4 | >60 |
| 19 | N | $CHCH_3$ | H | H | 100 | 94.4 | 84.7 | 68.3 | 42.4 | 52 |
| 28 | CH | $CH_2$ | H | 3-$OCH_3$ | 100 | 88.5 | 74.3 | 66.0 | 53.4 | >60 |
| A1 | N | S | H | H | 100 | 32.3 | 13.8 | 13.1 | 13.0 | 2.4 |
| A2 | N | S | $CH_3$ | H | 100 | 32.5 | 14.8 | 13.7 | 12.3 | 2.5 |
| A3 | N | S | $OCH_3$ | H | 100 | 38.3 | 18.6 | 19.2 | 16.5 | 3.0 |
| B1 | CH | S | $CH_3$ | H | 100 | 46.5 | 25.6 | 25.1 | 27.0 | 4.6 |
| B2 | CH | S | $OCH_3$ | H | 100 | 54.3 | 32.9 | 31.4 | 24.4 | 6.5 |

3. Oral absorption

The compound obtained in Example 1 was suspended in 0.5% sodium carboxymethyl cellulose, and was administered orally to the Wistar male rat at a dose of 30 mg/ml/kg. After administration, the rat is fixed on a plate with nails and strings.

Then, 20, 60, 120, 240 and 480 post medication, blood sample was collected by jugular puncture respectively. The serum was obtained by centrifuging with a blood serum separating tube (Separapid tube). To 100 μl of the serum thus obtained was added 300 μl of methanol, and the mixture was centrifuged. Next, 50 μl of the supernatant was applied to a high-performance liquid chromatography, and the blood level of the compound was measured. Conditions of the high-performance liquid chromatography are as follows:

Column: CSPAK CHEMCOSORB 300, 4.6 mm diameter and 150 mm length

Eluent: 48% $CH_3CN$-0.01% TFA
Flow rate: 1 ml/minute
Detection: UV 290 nm
Sensitivity: 0.01 AUFS
Colume temperature: 50° C.

As Comparative Example 10, the compound expressed in the following chemical formula disclosed in U.S. Pat. No. 4,824,834 was used, and tested as the same manner as in Example 1. These test results are shown in Table 5.

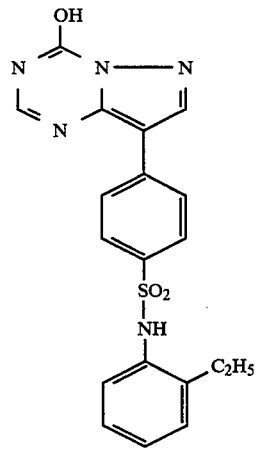

TABLE 5

| Test compound | Blood level (μg/ml) 20 minutes | 1 hours | 2 hours | 4 hours | 8 hours |
|---|---|---|---|---|---|
| Example 1 | 1.593 ± 0.372 | 2.691 ± 0.713 | 1.246 ± 0.632 | 1.419 ± 0.492 | 0.731 ± 0.159 |
| Comparative Example 10 | 0.000 ± 0.000 | 0.000 ± 0.000 | 0.000 ± 0.000 | 0.112 ± 0.102 | 0.031 ± 0.053 |

What is claimed is:

1. A condensed pyrazole derivative of the Formula (1):

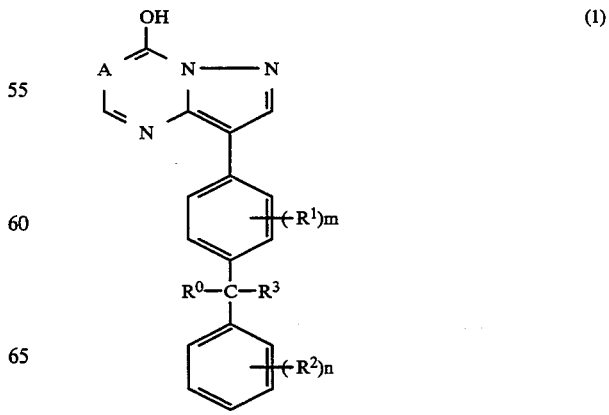

wherein A is N; $R^0$ and $R^3$ are the same or different, and are a hydrogen atom or a lower alkyl group, $R^1$ and $R^2$ are the same or different, and are a hydrogen atom, a lower alkyl group, a lower alkoxy group, a lower alkylthio group, a nitro group or a halogen atom, m is 1 or 2, and n is 1, 2 or 3, provided that, when n is 2 and the two $R^2$ groups are adjacent, the adjacent $R^2$ groups may be connected to form a lower alkylenedixoy group, or its pharmaceutically available salt.

2. A condensed pyrazole derivative or its pharmaceutically available salt according to claim 1, wherein $R^0$ and $R^3$ are the same or different, and are a hydrogen atom or a $C_1$-$C_6$ alkyl group, $R^1$ and $R^2$ are the same or different, and are a hydrogen atom, a $C_1$-$C_6$ alkyl group, a $C_1$-$C_6$ alkoxy group, a $C_1$-$C_6$ alkylthio group, a nitro group or a halogen atom, m is 1 or 2, and n is 1, 2 or 3, provided that, when n is 2 and the two $R^2$ groups are adjacent, the adjacent $R_2$ groups may be connected to form a $C_1$-$C_4$ alkylenedioxy group.

3. A condensed pyrazole derivative or its pharmaceutically available salt according to claim 2, wherein $R^1$ and $R^2$ are the same or different, and are a hydrogen atom, a $C_1$-$C_6$ alkyl group, a $C_1$-$C_6$ alkoxy group or a halogen atom, m is 1, and n is 1 or 2, provided that, when n is 2 and the two $R^2$ groups are adjacent, the adjacent $R^2$ groups may be connected to form a $C_1$-$C_4$ alkylenedioxy group.

4. A condensed pyrazole derivative or its pharmaceutically available salt according to claim 3, wherein $R^2$ is a $C_1$-$C_6$ alkyl group, a $C_1$-$C_6$ alkoxy group or a halogen atom, and n is 1.

5. A condensed pyrazole derivative or its pharmaceutically available salt according to claim 4, wherein $R^1$, $R^0$ and $R^3$ are hydrogen atoms.

6. A condensed pyrazole derivative or its pharmaceutically available salt according to claim 5, wherein $R^2$ is a $C_1$-$C_6$ alkoxy group.

7. A condensed pyrazole derivative or its pharmaceutically available salt according to claim 6, wherein $R^0$ and $R^3$ are a hydrogen atom, and $R^1$ is a $C_1$-$C_6$ alkyl group, a $C_1$-$C_6$ alkoxy group or a halogen atom.

8. 4-Hydroxy-8-[4-(3-methoxyphenylmethyl)phenyl]-pyrazolo-[1,5-a]-1,3,5-triazine, or 8-[4-(3-chlorophenylmethyl)phenyl]-4-hydroxypyrazolo[1,5-a]-1,3,5-triazine.

9. A pharmaceutical composition to be used as an androgen inhibitor comprising a therapeutically effective amount of a condensed pyrazole derivative of the Formula (1):

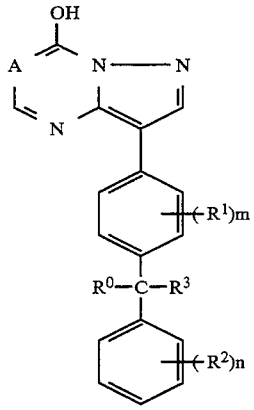

wherein A is N, $R^0$ and $R^3$ are the same or different, and are a hydrogen atom or a lower alkyl group, $R^1$ and $R^2$ are the same or different, and are a hydrogen atom, a lower alkyl group, a lower alkoxy group, a lower alkylthio group, a nitro group or a halogen atom, m is 1 or 2, and n is 1, 2 or 3, provided that, when n is 2 and the two $R^2$ groups are adjacent, the adjacent $R^2$ group may be connected to form a lower alkylenedioxy group), or its pharmaceutically available salt, and a pharmaceutically available carrier.

10. A therapeutic method for inhibiting expression of actions of androgens comprising internal administration or external application of a pharmaceutical preparation containing a condensed pyrazole derivative of the Formula (1) defined in claim 1 or its pharmaceutically available salt.

* * * * *